(12) United States Patent
Noguchi et al.

(10) Patent No.: US 6,300,331 B1
(45) Date of Patent: Oct. 9, 2001

(54) NAPHTHALIMIDOBENZAMIDE DERIVATIVES

(75) Inventors: Kazuharu Noguchi, Iruma; Motoji Wakida, Hidaka; Kenji Suzuki, Hanno; Yuji Yamada, Higashiyamato; Tetsuji Asao, Tokorozawa, all of (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/508,044

(22) PCT Filed: Jul. 2, 1999

(86) PCT No.: PCT/JP99/03574

§ 371 Date: Mar. 3, 2000

§ 102(e) Date: Mar. 3, 2000

(87) PCT Pub. No.: WO00/01672

PCT Pub. Date: Jan. 13, 2000

(30) Foreign Application Priority Data

Jul. 3, 1998 (JP) .................................. 10-189078

(51) Int. Cl.⁷ ...................... A61K 31/473; A61K 31/496; A61K 31/5355; C07D 401/14; C07D 401/12; C07D 221/14

(52) U.S. Cl. ................... 514/253.03; 514/232.8; 514/292; 514/296; 544/126; 544/361; 546/99; 546/87

(58) Field of Search ................... 546/99, 87; 544/126, 544/361; 514/232.8, 253.03, 292, 296

(56) References Cited

U.S. PATENT DOCUMENTS 5,086,059 * 2/1992 Ardecky ................. 514/284

FOREIGN PATENT DOCUMENTS

| 0 125 439 A2 | 11/1984 | (EP) . |
| 91/09850 | 7/1991 | (WO) . |
| 92/17453 | 10/1992 | (WO) . |
| 93/12092 | 6/1993 | (WO) . |

OTHER PUBLICATIONS

Sof'ina et al. National Cancer Institute Monograph 55. NIH Publication No. 80–1933. pp. 76–78, Dec. 1980.*

* cited by examiner

Primary Examiner—Evelyn Mei Huang
(74) Attorney, Agent, or Firm—Sughrue, Mion, Zinn, Macpeak & Seas, PLLC

(57) ABSTRACT

The present invention relates to a naphthalimidobenzamide derivative represented by the following formula (1):

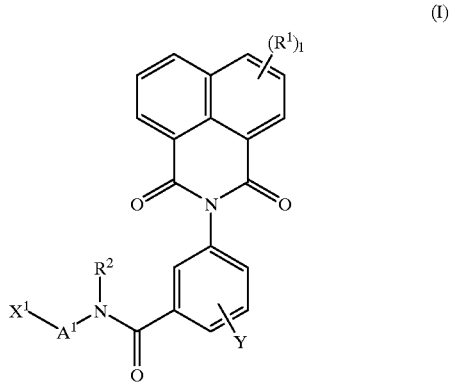

(wherein, $R^1$ represents a hydrogen atom, etc., Y represents a hydrogen atom or —CON($R^4$)—$A^2$—$X^2$, $R^2$ and $R^4$ are the same or different and each independently represents a hydrogen atom, etc., $A^1$ and $A^2$ are the same or different and each independently represents an alkylene group which may be interrupted at least once by —N($R^3$)— ($R^3$ representing a hydrogen atom, etc.) and $X^1$ and $X^2$ are the same or different and each independently represents a (hetero)aryl group which may have a substituent, etc.) or salt thereof; and a pharmaceutical comprising it as an effective ingredient. The compound is useful as an antitumor agent and the like.

12 Claims, No Drawings

NAPHTHALIMIDOBENZAMIDE DERIVATIVES

This application is the national phase of PCT/JP99/03576, filed on Jul. 2, 1999.

TECHNICAL FIELD

The present invention relates to novel naphthalimidobenzamide derivatives which have high affinity with DNA, have useful biological activity and are usable for the treatment of various diseases such as malignant tumor.

1. Background Art

In recent days, genetic information of various organisms including human being has been revealed vigorously. Pharmaceuticals having strong interaction with a specific region of a gene, thereby exhibiting their pharmacological action have increased their utility as a remedy having a high target orientation.

There is a strong demand for the development of a pharmaceutical which has particularly high affinity with DNA and exhibits excellent remedial effects for diseases such as malignant tumor.

2. Disclosure of the Invention

The present inventors have carried out an extensive investigation with a view to attaining the above-described object. As a result, it has been found that a novel naphthalimidobenzamide derivative represented by the below-descried formula (1) has high affinity with DNA, exhibits excellent anti-tumor activity and is therefore useful as a medicament such as a remedy for a malignant tumor or the like, leading to the completion of the present invention.

The present invention provides a naphthalimidobenzamide derivative represented by the following formula (1):

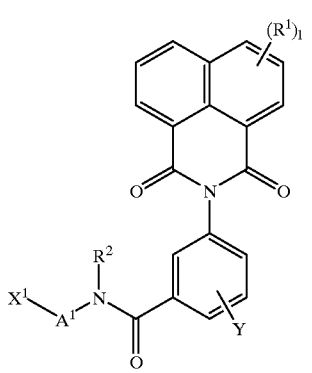

(I)

wherein, $R^1$ represents a hydrogen atom, a nitro group, a hydroxyl group, an amino group, a halogen atom, a cyano group, a carboxyl group, a carbamoyl group, an uleyl group, an alkyl group, a trihalogenoalkyl group, an alkoxy group, an alkylamino group, a dialkylamino group, an acyl group, an alkylcarbamoyl group, a dialkylcarbamoyl group, an acylamino group, an alkylureyl group or an alkoxycarbonylamino group;

$R^2$ represents a hydrogen atom or an alkyl group;

l stands for an integer of 1 to 3;

$A^1$ represents a linear or branched alkylene group which may be interrupted by —N($R^3$)— ($R^3$ representing a hydrogen atom or an alkyl group), —O—, —S—, —C(=O)NH—, —NHC(=O)—, —S(=O)— or —S(=O)$_2$—, $X^1$ represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group (the above-described aryl or heteroaryl group may have a substituent); and Y represents a hydrogen atom or —C(=O)N($R^4$)—$A^2$—$X^2$ ($R^4$ representing a hydrogen atom or an alkyl group and $A^2$ representing a linear or branched alkylene group which may be interrupted by —N($R^5$)— ($R^5$ representing a hydrogen atom or an alkyl group), —O—, —S—, —C(=O)NH—, —NHC(=O)—, —S(=O)— or —S(=O)$_2$—, $X^2$ representing a hydrogen atom, an aryl group, a heterocyclic group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group (the aryl or heteroaryl or heterocyclic group may have a substituent), or $R^4$, $A^2$ and $X^2$ may form, together with a nitrogen atom adjacent thereto, a nitrogen-containing heterocyclic ring which may have a substituent)], or a salt thereof; or a preparation process thereof.

The present invention also provides a pharmaceutical comprising, as an effective ingredient, a compound represented by the above-described formula (1) or salt thereof.

The present invention further provides a pharmaceutical composition comprising a compound represented by the above-described formula (1) or salt thereof and a pharmaceutically acceptable carrier. The present invention further provides the use of a compound represented by the above-described formula (1) or salt thereof as a pharmaceutical.

The present invention further provides a process for treating a malignant tumor, which comprises administering a compound represented by the above-described formula (1) or salt thereof.

Although compounds having a naphthalimidobenzamide skeleton are described in, for example, DE 2446533, DE 2436032, DE 2460390 and DE 2606904 and Japanese Patent Application Laid-Open No. HEI 7-234530, they are evidently different from the compounds of the formula (1) in structure and moreover, the above-described literature does not include any description of their pharmacological action.

BEST MODES FOR CARRYING OUT THE INVENTION

Described specifically, each group defined by $R^1$, $R^2$, $R^3$, $R^4$, $R^5$, $A^1$, $A^2$, $X^1$, $X^2$ and Y in the compounds represented by the above-described formula (1) and another group or symbol described herein are as follows:

In the compounds represented by the above-described formula (1), l pieces of $R^1$s may exist on any position on the naphthalimide group and they may be the same or different. Among them, preferred positions are 3-position, 4-position, 5-position and 6-position. l stands for an integer of 1 to 3, preferably 1 or 2.

$R^1$ represents a hydrogen atom, a nitro group, a hydroxyl group, an amino group, a halogen atom, a cyano group, a carboxyl group, a carbamoyl group, an ureyl group, an alkyl group, a trihalogenoalkyl group, an alkoxy group, an alkylamino group, a dialkylamino group, an acyl group, an alkylcarbamoyl group, a dialkylcarbamoyl group, an acylamino group, an alkylureyl group or an alkoxycarbonylamino group.

Examples of the halogen atom include fluorine, chlorine, bromine and iodine atoms.

As the alkyl group, $C_{1-6}$ alkyl groups are preferred. Specific examples include methyl, ethyl, n-propyl, isopropyl, n-butyl, isobutyl, sec-butyl, tert-butyl, pentyl and hexyl groups.

As the trihalogenoalkyl group, trihalogenomethyl groups are preferred. Specific examples include trifluoromethyl and trichloromethyl groups.

As the alkoxy group, $C_{1-6}$ alkoxy groups are preferred. Specific examples include methoxy, ethoxy, n-propoxy, isopropoxy, n-butoxy, isobutoxy, sec-butoxy, tert-butoxy, pentyloxy and hexyloxy groups.

As the mono- or di-alkylamino group, mono- or di($C_{1-6}$ alkyl)amino groups are preferred. Specific examples include methylamino, dimethylamino, ethylamino, diethylamino, n-propylamino, di-n-propylamino, isopropylamino, diisopropylamino, n-butylamino, di-n-butylamino, isobutylamino, diisobutylamino, sec-butylamino, di-sec-butylamino, tert-butylamino, di-tert-butylamino, pentylamino, dipentylamino, hexylamino and dihexylamino groups.

As the acyl group, $C_{1-6}$ acyl groups are preferred. Specific examples include formyl, acetyl, propionyl, butyryl, valeryl, isovaleryl, hexanoyl and pivaloyl groups.

As the alkylcarbamoyl group, $C_{1-6}$ alkylcarbamoyl groups are preferred. Specific examples include methylcarbamoyl, ethylcarbamoyl, n-propylcarbamoyl, isopropylcarbamoyl, n-butylcarbamoyl, isobutylcarbamoyl, sec-butylcarbamoyl, tert-butylcarbamoyl, pentylcarbamoyl and hexylcarbamoyl groups.

As the dialkylcarbamoyl group, di($C_{1-6}$ alkyl)carbamoyl groups are preferred. Specific examples include dimethylcarbamoyl, diethylcarbamoyl, methylethylcarbamoyl, di-n-propylcarbamoyl, diisopropylcarbamoyl, di-n-butylcarbamoyl, diisobutylcarbamoyl, di-sec-butylcarbamoyl, di-tert-butylcarbamoyl, dipentylcarbamoyl and dihexylcarbamoyl groups.

As the acylamino group, $C_{1-6}$ acylamino groups are preferred. Specific examples include formylamino, acetylamino, propionylamino, butyrylamino, 2-methylpropionylamino, pivaloylamino, pentanoylamino, 3-methylbutyrylamino and hexanoylamino groups.

As the alkylureyl group, $C_{1-6}$ alkylureyl groups are preferred. Specific examples include methylureyl, ethylureyl, n-propylureyl, isopropylureyl, n-butylureyl, isobutylureyl, sec-butylureyl, tert-butylureyl, pentylureyl and hexylureyl groups.

As the alkoxycarbonylamino group, $C_{1-6}$ alkoxycarbonylamino groups are preferred. Specific examples include methoxycarbonylamino, ethoxycarbonylamino, n-propoxycarbonylamino, isopropoxycarbonylamino, n-butoxycarbonylamino, isobutoxycarbonylamino, sec-butoxycarbonylamino, tert-butoxycarbonylamino, pentyloxycarbonylamino and hexyloxycarbonylamino groups.

Among them, preferred as $R^1$ are a hydrogen atom, a nitro group, an amino group, halogen atoms, trihalogenomethyl groups, $C_{1-6}$ alkyl groups and $C_{1-6}$ alkoxy groups, with a hydrogen atom, a nitro group, an amino group, $C_{1-6}$ alkoxy groups and halogen atoms being particularly preferred.

$R^2$, $R^3$, $R^4$ and $R^5$ may be the same or different and each independently represents a hydrogen atom or an alkyl group. As the alkyl group, $C_{1-6}$ alkyl groups, particularly $C_{1-3}$ alkyl groups are preferred. As the $C_{1-6}$ alkyl groups, those exemplified above as $R^1$ can be mentioned. Among them, a hydrogen atom is particularly preferred as each of $R^2$, $R^3$, $R^4$ and $R^5$.

$A^1$ and $A^2$ may be the same or different and each independently represents a linear or branched alkylene group which may be interrupted by —N($R^3$)— [or —N($R^5$)—] ($R^3$ and $R^5$ each has the same meaning as described above), —O—, —S—, —C(=O)NH—, —NHC(=O)—, —S(=O)— or —S(=O)$_2$—. Here, as the alkylene group, $C_{1-10}$ alkylene groups are preferred. Specific examples of $A^1$ or $A^2$ include methylene, ethylene, trimethylene, tetramethylene, pentamethylene, hexamethylene, heptamethylene, 2,2-dimethylpropylene, —(CH$_2$)$_2$—NH—(CH$_2$)$_2$—, —(CH$_2$)$_3$—NH—(CH$_2$)$_2$—, —(CH$_2$)$_3$—NH—(CH$_2$)$_3$—, —(CH$_2$)$_4$—NH—(CH$_2$)$_4$—, —(CH$_2$)$_5$—NH—(CH$_2$)$_5$—, —(CH$_2$)$_2$—N(CH$_3$)—(CH$_2$)$_2$—, —(CH$_2$)$_2$—NH—(CH$_2$)$_2$—NHCH$_2$—, —(CH$_2$)$_3$—N(CH(CH$_3$)$_2$)—(CH$_2$)$_3$—, —(CH$_2$)$_2$—CH(CH$_3$)—NH—(CH$_2$)$_4$—, —(CH$_2$)$_2$—NH—(CH$_2$)$_2$—NH—(CH$_2$)$_2$—, —(CH$_2$)$_2$—O—(CH$_2$)$_2$—, —(CH$_2$)$_2$—S—(CH$_2$)$_2$—, —(CH$_2$)$_2$—C(=O)—NH—(CH$_2$)$_2$—, —(CH$_2$)$_3$—NH—C(=O)—(CH$_2$)$_2$—, —(CH$_2$)$_4$—NH—C(=O)—(CH$_2$)$_4$—, —(CH$_2$)$_2$—S(=O)—(CH$_2$)$_2$— and —(CH$_2$)$_2$—S(=O)$_2$—(CH$_2$)$_2$—. Among them, more preferred are linear or branched $C_{1-10}$ alkylene groups each of which may be interrupted by —N($R^3$)— (or —N($R^5$)—), —O—, —S(=O)$_2$—, —C(=O)NH— or —NHC(=O)—, of which the linear or branched $C_{1-10}$ alkylene groups each of which may be interrupted by —NH—, —O— or —S(=O)$_2$— are particularly preferred and methylene, ethylene, trimethylene, tetramethylene, —(CH$_2$)$_2$—NH—(CH$_2$)$_2$—, —(CH$_2$)$_3$—NH—(CH$_2$)$_2$— and —(CH$_2$)$_3$—NH—(CH$_2$)$_3$— groups are most preferred.

$X^1$ represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group (said aryl or heteroaryl ring may have a substituent). As the above-described aryl ring, $C_{6-18}$ monocylclic to tetracyclic ones are preferred. As the heteroaryl ring, monocyclic to tetracyclic ones having 1 to 5 hetero atoms selected from nitrogen, oxygen and sulfur atoms and 2 to 17 carbon atoms are preferred. The aryl or heteroaryl may hereinafter be called (hetero)aryl. Examples of the aryl or heteroaryl ring include benzene, naphthalene, naphthoquinone, azulene, anthracene, anthraquinone, phenanthrene, phenanthrenequinone, fluoranthene, benzanthracene, acenaphthylene, acenaphthenequinone, chrysene, chrysenquinone, pyrene, furan, pyrrole, thiophene, pyrazole, imidazole, oxazole, thiazole, triazole, thiadiazole, pyridine, pyridazine, pyrimidine, pyrazine, indole, isoindole, indazole, benzofuran, thionaphthene, benzoxazole, benzisoxazole, benzothiazole, benzimidazole, imidazopyridine, imidazopyrimidine, benzotriazole, triazolopyridine, triazolopyrimidine, triazoloquinoline, quinoline, isoquinoline, quinasoline, phthalazine, pteridine, dibenzofuran, iminostilbene, benzoquinoline, benzisoquinoline, benzosinoline, pyridoindole, phenanthridine, phenanthroline, phenazine, phenothiazine, thianthrene, phenoxazine, carbazole, acridine, xanthone, benzacridine, benzonaphthothiophene and quinoxaline.

They are (hetero)aryldicarbonylimino, (hetero)arylamino, (hetero)arylcarbonylamino, (hetero)arylcarbamoyl, (hetero)aryloxy, (hetero)arylthio, (hetero)arylsulfinyl and (hetero)arylsulfonyl groups each having, at any position of the (hetero)aryl group, a dicarbonylimino, amino, carbonylamino, carbamoyl, oxy, thio, sulfinyl or sulfonyl group bound thereto.

Examples of the substituent for the above-exemplified aryl or heteroaryl ring include a nitro group, a hydroxyl group, an amino group, halogen atoms, a cyano group, a carboxyl group, a carbamoyl group, an uleyl group, alkyl groups (preferably, $C_{1-6}$ alkyl), trihalogenoalkyl groups (preferably, trihalogenomethyl), alkoxy groups (preferably, $C_{1-6}$ alkoxy), alkylamino groups (preferably $C_{1-6}$ alkylamino), dialkylamino groups (preferably, di($C_{1-6}$ alkyl)amino), acyl groups (preferably, $C_{1-6}$ acyl), alkylcarbamoyl groups (preferably, $C_{1-6}$ alkylcarbamoyl), alkylaminoalkylcarbamoyl groups (preferably, $C_{1-6}$ alkylamino-$C_{1-6}$ alkylcarbamoyl), dialkylaminoalkylcarbamoyl groups (preferably, di($C_{1-6}$ alkyl)amino-$C_{1-6}$ alkylcarbamoyl), dialkylcarbamoyl groups (preferably, di($C_{1-6}$ alkyl)carbamoyl), acylamino groups (preferably, $C_{1-6}$ acylamino), alkylureyl groups (preferably, $C_{1-6}$ alkylureyl), alkoxycarbonylamino groups (preferably, $C_{1-6}$ alkoxycarbonylamino), (hetero)aryl groups, (hetero)arylamino groups, (hetero)arylcarbonylamino groups, (hetero)arylcarbamoyl groups, (hetero)aryloxy groups and (hetero)arylthio groups. The aryl or heteroaryl ring may have one or more substituents which may be the same or different. The (hetero)aryl groups serving as a substituent are similar to those exemplified above and may be substituted further with a nitro group, a hydroxyl group, an amino group, a halogen atom, a cyano group, a carboxyl group, a carbamoyl group, an ureyl group, an alkyl group (preferably, a $C_{1-6}$ alkyl group), a trihalogenoalkyl group (preferably, a trihalogenomethyl group), an alkoxy group (preferably, a $C_{1-6}$ alkoxy group), an alkylamino group (preferably, a $C_{1-6}$ alkylamino group), a dialkylamino group (preferably, a di($C_{1-6}$ alkyl)amino group), an acyl group (preferably, a $C_{1-6}$ acyl group), an alkylcarbamoyl group (preferably, a $C_{1-6}$ alkylcarbamoyl group), an alkylaminoalkylcarbamoyl group (preferably, a $C_{1-6}$ alkylamino-$C_{1-6}$ alkylcarbamoyl group), a dialkylaminoalkylcarbamoyl group (preferably, a di($C_{1-6}$ alkyl)amino-$C_{1-6}$ alkylcarbamoyl group), a dialkylcarbamoyl group (preferably, a di($C_{1-6}$ alkyl)carbamoyl group), an acylamino group (preferably, a $C_{1-6}$ acylamino group), an alkylureyl group (preferably, a $C_{1-6}$ alkylureyl group), an alkoxycarbonylamino group (preferably, a $C_{1-6}$ alkoxycarbonylamino group), a (hetero)arylcarbonylamino group which may have a substituent or a (hetero)arylcarbamoyl group which may have a substituent. Examples of the substituent for the above-described (hetero)arylcarbonylamino group which may have a substituent or (hetero)arylcarbamoyl group which may have a substituent include a nitro group, a hydroxyl group, an amino group, halogen atoms, a cyano group, a carboxyl group, a carbamoyl group, an ureyl group, alkyl groups (preferably, $C_{1-6}$ alkyl), trihalogenoalkyl groups (preferably, trihalogenomethyl), alkoxy groups (preferably, $C_{1-6}$ alkoxy), alkylamino groups (preferably, $C_{1-6}$ alkylamino), dialkylamino groups (preferably, di($C_{1-6}$ alkyl)amino), acyl groups (preferably, $C_{1-6}$ acyl), alkylcarbamoyl groups (preferably, $C_{1-6}$ alkylcarbamoyl), alkylaminoalkylcarbamoyl groups (preferably, $C_{1-6}$ alkylamino-$C_{1-6}$ alkycarbamoyl), dialkylaminoalkylcarbamoyl groups (preferably, di($C_{1-6}$ alkyl)amino-$C_{1-6}$ alkylcarbamoyl), dialkylcarbamoyl groups (preferably, di($C_{1-6}$ alkyl)carbamoyl), acylamino groups (preferably, $C_{1-6}$ acylamino), alkylureyl groups (preferably, $C_{1-6}$ alkylureyl) and alkoxycarbonylamino groups (preferably, $C_{1-6}$ alkoxycarbonylamino). As examples of the $C_{1-6}$ alkyl, $C_{1-6}$ alkoxy, mono- or di($C_{1-6}$ alkyl)amino, $C_{1-6}$ acyl, $C_{1-6}$ alkylcarbamoyl, di($C_{1-6}$ alkyl)carbamoyl, $C_{1-6}$ acylamino, $C_{1-6}$ alkylureyl and $C_{1-6}$ alkoxycarbonylamino groups, those exemplified above can be mentioned. Examples of the di($C_{1-6}$ alkyl)amino-$C_{1-6}$ alkylcarbamoyl groups include dimethylaminomethylcarbamoyl, dimethylaminoethylcarbamoyl, dimethylamino-n-propylcarbamoyl, dimethylaminoisopropylcarbamoyl, dimethylamino-n-butylcarbamoyl, dimethylamino-sec-butylcarbamoyl, dimethylaminopentylcarbamoyl, dimethylaminohexylcarbamoyl, dipropylamino-n-propylcarbamoyl and dihexylaminoisohexylcarbamoyl groups.

Among them, preferred as $X^1$ are (hetero)aryldicarbonylimino, (hetero)aryl, (hetero)arylcarbonylamino and (hetero)arylcarbamoyl groups which may have a substituent, of which more preferred are those having, as the aryl ring, a $C_{6-18}$ monocyclic to tetracyclic aryl group or having, as the heteroaryl ring, a monocyclic to tetracyclic heteroaryl groups having 1 to 5 hetero atoms selected from nitrogen, oxygen and sulfur atoms and 2 to 17 carbon atoms; and having, as a substituent for the aryl or heteroaryl ring, a substituent selected from halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heteroaryl groups or a substituent selected from monocyclic nitrogen-containing heteroarylcarbamoyl groups having the above-exemplified substituent, monocyclic nitrogen-containing heteroarylcarbonylamino groups having the above-exemplified substituent, monocyclic nitrogen-containing heteroarylcarbamoyl-monocylic nitrogen-containing heteroarylcarbamoyl groups having the above-exemplified substituent and monocyclic nitrogen-containing heteroarylcarbonylamino-monocyclic nitrogen-containing heteroarylcarbonylamino groups having the above-exemplified substituent.

Particularly preferred examples of $X^1$ include naphthalene-2-carbonylamino, naphthalene-2-carbamoyl, anthracene-9-carbonylamino, phthalimide, 1,8-naphthalimide, 3-nitro-1,8-naphthalimide, 4--nitro-1,8-naphthalimide, 4-amino-1,8-naphthalimide, 3-hydroxy-1,8-naphthalimide, 4-hydroxy-1,8-naphthalimide, 3-ethoxy-1,8-naphthaiimide, 4-fluoro-1,8-naphthalimide, 3-chloro-1,8-naphthalimide, 4-chloro-1,8-naphthalimide, 3-bromo-1,8-naphthalimide, 4-bromo-1,8-naphthaimide, 2,3-naphthalimide, pyrido[3,4-b]indol-9-yl, acridineamino, quinoline-3-carbonylamino, quinoline-4-carbonylamino, quinoxaline-2-carbonylamino, 1-methylindole-2-carbonylamino, 4-nitro-1-methylpyrrole-2-carbonylamino, N-[2-[N-(3-dimethylaminopropyl)carbamoyl]-1-methylpyrrol-4-yl]carbamoyl, N-[2-[N-[2-[N-(3-dimethylaminopropyl)carbamoyl]-1-methylpyrrol-4-yl]carbamoyl]-1-methylpyrrol-4-yl]carbamoyl, 4-(4-formamido-1-methylpyrrole-2-carbonylamino)-1-methylpyrrole-2-carbonylamino, 4-[4-(4-formamido-1-methylpyrrole-2-carbonylamino)-1-methylpyrrole-2-carbonylamino]-1-methylpyrrole-2-carbonylamino and N-[2-[N-[2-(N-methylcarbamoyl)-1-methylpyrrol-4-yl]carbamoyl]-1-methylpyrrol-4-yl]carbamoyl groups.

Most preferred examples of $X^1$ include phthalimide, 1,8-naphthalimide, 3-nitro-1,8-naphthalimide, 4-amino-1,8- naphthalimide, 4-chloro-1,8-naphthalimide, 2,3-naphthalimide, pyrido[3,4-b]indol-9-yl, quinoline-3-carbonylamino, quinoline-4-carbonylamino, quinoxaline-2-carbonylamino, 1-methylindole-2-carbonylamino, 4-nitro-1-methylpyrrole-2-carbonylamino, N-[2-[N-(3-dimethylaminopropyl)carbamoyl]-1-methylpyrrol-4-yl] carbamoyl, N-[2-[N-[2-[N-(3-dimethylaminopropyl)carbarnoyl]-1-methylpyrrol-4-yl]carbamoyl]-1-methylpyrrol-4-yl]carbamoyl, 4-(4-formamido-1-methylpyrrole-2-carbonylamino)-1-methylpyrrole-2-carbonylamino, 4-[4-(4-formamido-1-methylpyrrole-2-carbonylamino)-1-methylpyrrole-2-carbonylamino]-1-methylpyrrole-2-carbonylamino and N-[2-[N-[2-(N-methylcarbamoyl)-1-methylpyrrole-4-yl]carbamoyl]-1-methylpyrrol-4-yl]carbamoyl groups.

$X^2$ represents a hydrogen atom, an aryl group, a heterocyclic group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group (the above-described aryl or heteroaryl ring or heterocyclic group may have a substituent), or $X^2$, $R^4$ and $A^2$ may form, together with a nitrogen atom adjacent thereto, a nitrogen-containing heterocyclic ring which may have a substituent.

Here, as the aryl, (hetero)aryldicarbonylimino, (hetero)arylamino, (hetero)arylcarbonylamino, (hetero)arylcarbamoyl, (hetero)aryloxy, (hetero)arylthio, (hetero)arylsulfinyl and (hetero)arylsulfonyl groups (these (hetero)aryl groups may have a substituent), those exemplified as $X^1$ can be mentioned as examples and preferred ones are also similar to those of $X^1$.

As examples of the heterocyclic group represented by $X^2$, monocyclic to tetracyclic, saturated or unsaturated heterocyclic groups having 1 to 5 hetero atoms selected from nitrogen, oxygen and sulfur atoms, and 2 to 17 carbon atoms can be mentioned. Examples of the heterocyclic ring include heteroaryl groups exemplified above as $X^1$ and saturated heterocyclic groups.

Here, examples of the saturated heterocyclic group include aziridino, azetidino, pyrrolidino, tetrahydrofuryl, tetrahydrothienyl, piperidino, piperazino, morpholino, thiomorpholino, S,S-dioxythiomorpholino, tetrahydropyranyl, homopiperidino and homopiperazino groups. As the substituent for these heterocyclic groups, those exemplified above as the substituent for the (hetero) aryl ring in the description of $X^1$ can be mentioned.

As the nitrogen-containing heterocyclic group which is formed by $R^4$, $A^2$ and $X^2$ together with the adjacent nitrogen atom, 4 to 7-membered saturated heterocyclic groups having at least one nitrogen atom and 1 to 4, in total, of hetero atoms selected from oxygen and sulfur atoms are preferred. Specific examples include aziridino, azetidino, pyrrolidino, piperidino, piperazino, morpholino, thiomorpholino, S,S-dioxythiomorpholino, homopiperidino and homopiperazino groups. Examples of the substituent for the nitrogen-containing heterocyclic group include alkyl groups (preferably, $C_{1-6}$ alkyl), aryl groups (preferably, $C_{6-14}$ aryl), aralkyl groups (preferably, $C_{7-15}$ aralkyl), alkylamino groups (preferably, $C_{1-6}$ alkylamino), dialkylamino groups (preferably, di($C_{1-6}$ alkyl)amino), cyclic-alkyl-substituted amino groups (preferably, mono- or di-(cyclic $C_{3-6}$ alkyl)-substituted amino) and saturated nitrogen-containing heterocyclic groups (preferably, azetidino, pyrrolidino, piperidino, morpholino, thiomorpholino, etc.).

Specific examples of the nitrogen-containing heterocyclic group which may have a substituent include pyrrolidino, morpholino, thiomorpholino, 4-methylpiperazinyl, 4-ethylpiperazinyl, 4-propylpiperazinyl, 4-isopropylpiperazinyl, 4-phenylpiperazinyl, 4-benzylpiperazinyl, 4-butylpiperazinyl, 4-azetidinopiperidinyl, 4-pyrrolidinopiperidinyl, 4-methylaminopiperidinyl, 4-ethylaminopiperidinyl, 4-isopropylaminopiperidinyl, 4-butylaminopiperidinyl, 4-dimethylaminopiperidinyl, 4-diethylaminopiperidinyl, 4-diisopropylaminopiperidinyl, 4-dibutylaminopiperidinyl, 4-cyclopropylaminopiperidinyl, 4-cyclobutylaminopiperidinyl, 4-cyclopentylaminopiperidinyl, 4-cyclohexylaminopiperidinyl, 4-dicyclopropylaminopiperidinyl, 4-dicyclobutylaminopiperidinyl, 4-dicyclopentylaminopiperidinyl, 4-dicyclohexylaminopiperidinyl, 4-piperidinopiperidinyl, 4-morpholinopiperidinyl and 4-thiomorpholinopiperidinyl groups.

Examples of Y when $X^2$ represents a hydrogen atom include methylcarbamoyl, ethylcarbamoyl, n-propylcarbamoyl, isopropylcarbamoyl, n-butylcarbamoyl, dimethylcarbamoyl, diethylcarbamoyl, 2-methylaminoethylcarbamoyl, 2-methylaminopropylcarbamoyl, 2-dimethylaminoethylcarbamoyl, 2-diethylaminoethylcarbamoyl, 3-dimethylaminopropylcarbamoyl, 3-diethylaminopropylcarbamoyl, 4-ethoxybutylcarbamoyl, 5-methoxypentylcarbamoyl and 6-ethylaminohexylcarbamoyl groups.

Examples of Y when $X^2$ represents a saturated heterocyclic group which may have a substituent include 3-(pyrrolidin-1-yl)propylcarbamoyl, 2-(pyrrolidin-1-yl) ethylcarbamoyl, 2-(piperidin-1-yl)ethylcarbamoyl, 2-(4-dicyclopropylaminopiperidin-1-yl)ethylcarbamoyl, 2-(4-methylpiperazin-1-yl)ethylcarbamoyl and 2-(azetidin-1-yl) ethylcarbamoyl groups.

As specific examples of the (hetero)aryl, (hetero)aryldicarbonylimino, (hetero)arylamino, (hetero)arylcarbonylamino, (hetero)arylcarbamoyl, (hetero)aryloxy, (hetero)arylthio, (hetero)arylsulfinyl or (hetero)arylsufonyl group which is represented by $R^2$ and may have a substituent, those specifically exemplified above as $X^1$ can be mentioned.

Specific examples of Y when $X^2$, together with $R^4$ and $A^2$, forms a nitrogen-containing heterocyclic ring include pyrrolidin-1-ylcarbonyl, piperidin-1-ylcarbonyl, morpholin-4-ylcarbonyl, 4-(piperidin-1-yl)piperidin-1-ylcarbonyl, 4-methylpiperiazin-1-ylcarbonyl and 4-ethylpiperazin-1-ylcarbonyl groups.

Y may be substituted at any substitutable position on the benzene ring of the formula (1), but meta position relative to the naphthalimide group is preferred.

The naphthalimidobenzamide derivatives according to the present invention can form pharmaceutically acceptable salts thereof. Specific examples include salts with a mineral acid such as hydrochlorides, hydrobromides, sulfates, nitrates and phosphates; and salts with an organic acid such as trifluoroacetates, acetates, propionates, tartrates, fumarates, maleates, malates, citrates, methanesulfonates and paratoluenesulfonates. The naphthalimidobenzamide derivatives of the present invention may be solvates typified by hydrates.

Preferred specific examples of the invention compounds will next be shown in Tables 1 to 14.

TABLE 1
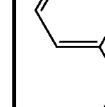
| Compound No. | $X^1$ | $A^1$ | $R^1$ | 1 | $R^2$ | Y |
|---|---|---|---|---|---|---|
| 1 | 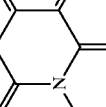 | —(CH$_2$)$_2$—NH—(CH$_2$)$_2$— | H | 1 | H | 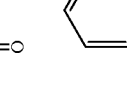 |
| 2 | 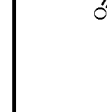 | —(CH$_2$)$_2$—NH—(CH$_2$)$_2$— | H | 1 | H |  |

TABLE 1-continued

| Compound No. | X¹ | A¹ | R¹ | 1 | R² | Y |
|---|---|---|---|---|---|---|
| 3 | (9H-pyrido[3,4-b]indol-9-yl, N-methyl) | —(CH₂)₂—NH—(CH₂)₂— | 3-NO₂— | 1 | H | (9H-pyrido[3,4-b]indol-9-yl)ethyl-NH-C(O)-CH₃ |
| 4 | (6-nitro-1,3-dioxo-1H-benz[de]isoquinolin-2(3H)-yl, N-methyl) | —(CH₂)₂—NH—(CH₂)₂— | 3-NO₂— | 1 | H | (6-nitro-1,3-dioxo-benz[de]isoquinolin-2-yl)ethyl-NH-C(O)-CH₃ |
| 5 | (1,3-dioxoisoindolin-2-yl, N-methyl) | —(CH₂)₂—NH—(CH₂)₂— | 3-NO₂— | 1 | H | (1,3-dioxoisoindolin-2-yl)ethyl-NH-C(O)-CH₃ |

TABLE 2

| Compound No. | X¹ | A¹ | R¹ | 6 | R² | Y |
|---|---|---|---|---|---|---|
| 6 | (N-methyl naphthalimide) | —(CH₂)₂—NH—(CH₂)₂— | 3-NO₂— | 1 | H | (naphthalimide-ethyl-NH-ethyl-NHAc) |
| 7 | (N-methyl naphthalene-dicarboximide) | —(CH₂)₂—NH—(CH₂)₂— | 3-NO₂— | 1 | H | (naphthalene-dicarboximide-ethyl-NH-ethyl-NHAc) |

TABLE 2-continued

| Compound No. | X¹ | A¹ | R¹ | R² | Y |
|---|---|---|---|---|---|
| 8 | (naphthalimide with Cl) | $-(CH_2)_2-NH-(CH_2)_2-$ | 3-NO$_2$— | H | (4-chloro-naphthalimide-ethyl-NH-ethyl-NHAc) |
| 9 | (naphthalimide with O$_2$N) | $-(CH_2)_2-O-(CH_2)_2-$ | 3-C$_2$H$_5$O— | H | (nitro-naphthalimide-ethyl-O-ethyl-NHAc) |

TABLE 2-continued

| Compound No. | X¹ | A¹ | R¹ | R² | Y |
|---|---|---|---|---|---|
| 10 | (4-chloro-1,8-naphthalimide-N-yl) | —(CH$_2$)$_2$—NH—(CH$_2$)$_2$— | H | H | NHC(O)CH$_3$ |

TABLE 3
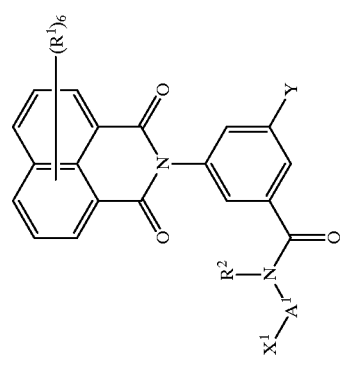
| Compound No. | X¹ | A¹ | R¹ | R² | Y |
|---|---|---|---|---|---|
| 11 | (structure shown) | —(CH₂)₃—NH—(CH₂)₂— (A)<br>—(CH₂)₂—NH—(CH₂)₃— (B) | 3-NO₂— | 1 | H |

TABLE 3-continued

| Compound No. | X¹ | A¹ | R¹ | R² | Y |
|---|---|---|---|---|---|
| 12 | | —(CH₂)₃—NH—(CH₂)₃— | 3-NO₂— | 1 | H |
| 13 | | —(CH₂)₂—NH—(CH₂)₂— | 4-NH₂— | 1 | H |
| 14 | | —(CH₂)₂—NH—(CH₂)₂— | 3-NO₂— | 1 | H |

TABLE 3-continued

| Compound No. | $X^1$ | $A^1$ | $R^1$ | $R^2$ | Y |
|---|---|---|---|---|---|
| 15 | (naphthalimide group) | $-(CH_2)_2-NH-(CH_2)_2-$ | H | 1 | $CH_3-$ (with naphthalimide-ethyl-NH-ethyl-N(CH$_3$)-C(=O)- group) |

TABLE 4

| Compound No. | X¹ | A¹ | R¹ | 1 | R² | Y |
|---|---|---|---|---|---|---|
| 16 | (3-nitro-N-methyl-naphthalimide) | —(CH₂)₂—NH—(CH₂)₂— | 3-NO₂— | 1 | H | (quinoline-4-carboxamide group) |
| 17 | (3-nitro-N-methyl-naphthalimide) | —(CH₂)₂—NH—(CH₂)₂— | 3-NO₂— | 1 | H | (quinoxaline-2-carboxamide group) |

TABLE 4-continued
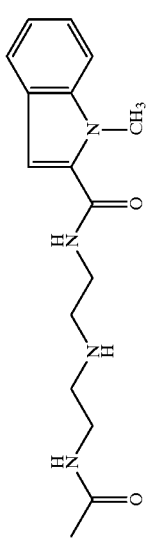
| Compound No. | X¹ | A¹ | R¹ | R² | Y |
|---|---|---|---|---|---|
| 18 | 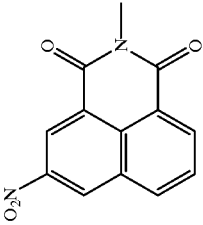 | —(CH$_2$)$_2$—NH—(CH$_2$)$_2$— | 3-NO$_2$— | H | 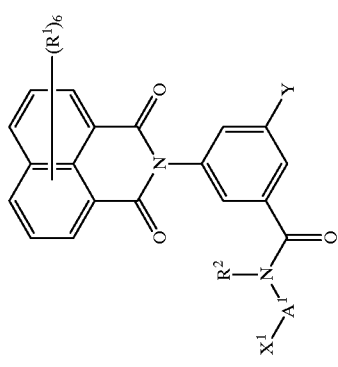 |
| 19 | | —(CH$_2$)$_2$—NH—(CH$_2$)$_2$— | 3-NO$_2$— | H | |

TABLE 4-continued

[Structure: naphthalimide with (R¹)₆ substituents, N-linked to phenyl ring bearing Y and C(=O)N(R²)–A¹–X¹]

| Compound No. | X¹ | A¹ | R¹ | R² | Y |
|---|---|---|---|---|---|
| 20 | [2-hydroxynaphthalen-1-yl-C(=O)NH–] | –(CH₂)₂–NH–(CH₂)₂– | 3-NO₂— | 1 | H |

X¹ = 2-hydroxy-naphthalene-1-carboxamide group; the terminal group on the other end is an acetamido (CH₃C(=O)NH–) moiety connected through the –(CH₂)₂–NH–(CH₂)₂– linker to the amide bearing the 2-hydroxynaphthyl-1-carbonyl group.

TABLE 5
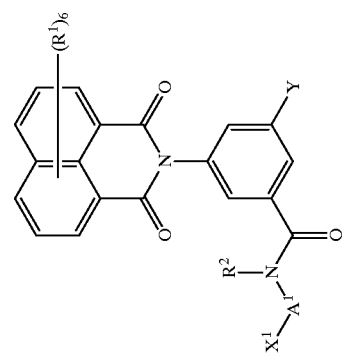
| Compound No. | X¹ | A¹ | R¹ | R² | Y |
|---|---|---|---|---|---|
| 21 | 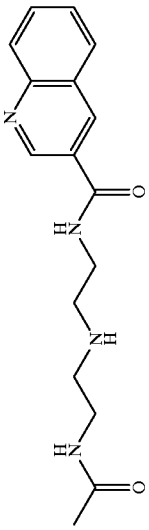 | —(CH₂)₂—NH—(CH₂)₂— | 3-NO₂— | 1 | H |
| 22 | 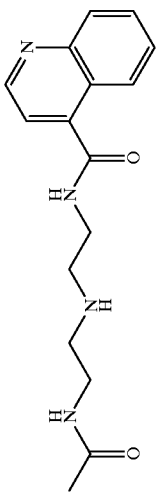 | —(CH₂)₂—NH—(CH₂)₂— | 3-NO₂— | 1 | H |
| 23 | 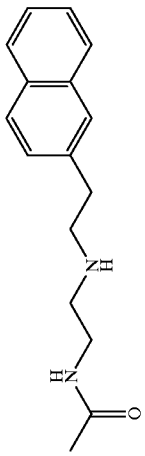 | —(CH₂)₂—NH—(CH₂)₂— | 3-NO₂— | 1 | H |

TABLE 5-continued

| Compound No. | X¹ | A¹ | R¹ | R² | Y |
|---|---|---|---|---|---|
| 24 | (structure: 4-nitro-1-methyl-pyrrole-2-carboxamide, N-methyl-pyrrolidine with CONH) | —(CH₂)₂—NH—(CH₂)₂— | 3-NO₂— | 1 | H | (structure: acetamido-ethyl-NH-ethyl-NH-C(O)-1-methyl-4-nitropyrrole) |
| 25 | (structure: acetamido-1-methyl-pyrrole-2-carboxamido-propyl-N(CH₃)₂) | —CH₂— | H | 1 | H | (structure: acetamido-CH₂-C(O)NH-1-methylpyrrole-C(O)NH-propyl-N(CH₃)₂) |

TABLE 6

| Compound No. | X¹ | A¹ | R¹ | | R² | Y |
|---|---|---|---|---|---|---|
| 26 | [pyrrole-amide with (CH₃)₂N-propyl and acetamido substituents] | —CH₂— | 3-NO₂— | 1 | H | [pyrrole-amide with N(CH₃)₂-propyl and acetamido-glycinamide substituents] |
| 27 | [pyrrole-amide with (CH₃)₂N-propyl and acetamido substituents] | —CH₂— | 4-NO₂— | 1 | H | [pyrrole-amide with N(CH₃)₂-propyl and acetamido-glycinamide substituents] |

TABLE 6-continued

[Structure: naphthalimide-phenyl-carboxamide core with substituents $(R^1)_6$, $X^1$, $A^1$, $R^2$, Y]

| Compound No. | X$^1$ | A$^1$ | R$^1$ | l | R$^2$ | Y |
|---|---|---|---|---|---|---|
| 28 | [N-methylpyrrole-2-carboxamide linked to 3-(dimethylamino)propyl, 4-acetamido] | —(CH$_2$)$_2$— | 3-NO$_2$— | 1 | H | [acetamido-CH$_2$CH$_2$-C(O)NH-(N-methylpyrrole)-C(O)NH-(CH$_2$)$_3$-N(CH$_3$)$_2$] |
| 29 | [N-methylpyrrole-2-carboxamide linked to 3-(dimethylamino)propyl, 4-acetamido] | —(CH$_2$)$_2$— | 4-CH$_3$O— | 1 | H | [acetamido-CH$_2$CH$_2$-C(O)NH-(N-methylpyrrole)-C(O)NH-(CH$_2$)$_3$-N(CH$_3$)$_2$] |

TABLE 6-continued

| Compound No. | X¹ | A¹ | R¹ | | R² | Y |
|---|---|---|---|---|---|---|
| 30 | (pyrrole-amide structure with terminal (CH₃)₂N(CH₂)₃-) | —(CH₂)₃— | 3-NO₂— | 1 | H | (acetamido-butyryl-pyrrole-amide structure with terminal -N(CH₃)₂) |

TABLE 7

| Compound No. | X¹ | A¹ | R¹ | R² | Y |
|---|---|---|---|---|---|
| 31 | (pyrrole-pyrrole with acetamide and (CH₃)₂N-propyl chain) | —(CH₂)₃— | 3-NO₂ | 1 | H | (pyrrole-pyrrole with glutaramide linker and N(CH₃)₂-butyl chain) |
| 32 | (bis-pyrrole with acetamide and (CH₃)₂N-propyl chain) | —CH₂— | 3-NO₂ | 1 | H | (bis-pyrrole with glycinamide linker and N(CH₃)₂-butyl chain) |

TABLE 7-continued

| Compound No. | X¹ | A¹ | R¹ | R² | Y |
|---|---|---|---|---|---|
| 33 | (structure shown) | —(CH₂)₂— | 3-NO₂— 1 | H | (structure shown) |
| 34 | (structure shown) | —(CH₂)₄— | 3-NO₂— 1 | H | (structure shown) |

TABLE 7-continued

| Compound No. | X¹ | A¹ | R¹ | 1 | R² | Y |
|---|---|---|---|---|---|---|
| 35 | HCONH-[pyrrole-CH₃]-C(O)NH-[pyrrole-CH₃]-C(O)NH-CH₃ | —(CH₂)₂—NH—(CH₂)₂— | 3-NO₂— | 1 | H | NHCHO-[pyrrole-CH₃]-C(O)NH-[pyrrole-CH₃]-C(O)NH-(CH₂)₂-NH-(CH₂)₂-NHC(O)CH₃ |

TABLE 8

[Structure: naphthalimide core with (R¹)₆ substituents, N-linked to phenyl bearing Y substituent and C(=O)-N(R²)-A¹-X¹ chain]

| Compound No. | X¹ | Y | A¹ | R¹ | R² |
|---|---|---|---|---|---|
| 36 | HCONH-pyrrole(CH₃)-CONH-pyrrole(CH₃)-CONH-pyrrole(CH₃)-C(O)NHCH₃ | NHCHO-pyrrole(CH₃)-CONH-pyrrole(CH₃)-CONH-pyrrole(CH₃)-CONH-(CH₂)₂-NH-(CH₂)₂-NHC(O)CH₃ | —(CH₂)₂—NH—(CH₂)₂— | 3-NO₂— | 1 | H |
| 37 | 3-nitro-N-methyl-naphthalimide | N(CH₃)₂-(CH₂)₄-NHC(O)-pyrrole(CH₃)-pyrrole(CH₃)-NHC(O)-(CH₂)₃-NHC(O)CH₃ | —(CH₂)₂—NH—(CH₂)₂— | 3-NO₂— | 1 | H |

TABLE 8-continued

| Compound No. | X¹ | A¹ | R¹ | R² | Y |
|---|---|---|---|---|---|
| 38 | 3-nitro-N-methyl-naphthalimide | —(CH₂)₂—NH—(CH₂)₂— | 3-NO₂— | 1 | H | N-methylpyrrole-2-carboxamide linked via 3-aminopropyl-N,N-dimethylamine, with β-alanine acetamide linker |
| 39 | 3-nitro-N-methyl-naphthalimide | —(CH₂)₂—NH—(CH₂)₂— | 3-NO₂— | 1 | H | N-methylpyrrole-2-carboxamide linked via 3-aminopropyl-N,N-dimethylamine, with γ-aminobutyryl acetamide linker |
| 40 | N-methyl-naphthalimide | —(CH₂)₂—NH—(CH₂)₂— | 3-NO₂— | 1 | H | bis(N-methylpyrrole-2-carboxamide) linked via 3-aminopropyl-N,N-dimethylamine, with γ-aminobutyryl acetamide linker |

TABLE 9
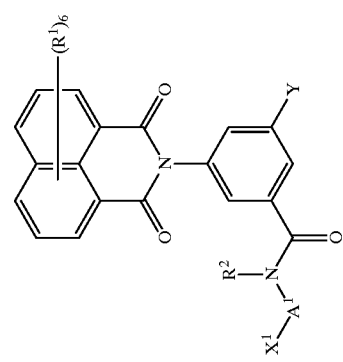
| Compound No. | X¹ | A¹ | R¹ | 1 | R² | Y |
|---|---|---|---|---|---|---|
| 41 | 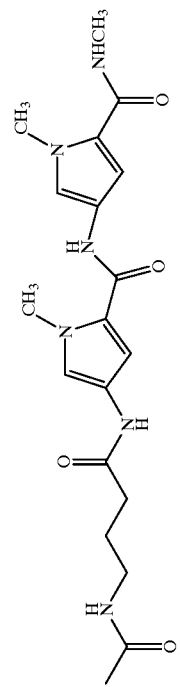 | —(CH$_2$)$_2$—NH—(CH$_2$)$_2$— | 3-NO$_2$— | 1 | H | 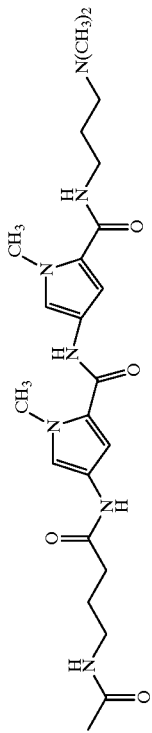 |
| 42 | (same naphthalimide as above) | —(CH$_2$)$_2$—NH—(CH$_2$)$_2$— | 3-NH$_2$— | 1 | H | (second Y structure) |

TABLE 9-continued

| Compound No. | X¹ | A¹ | R¹ | 1 | R² | Y |
|---|---|---|---|---|---|---|
| 43 | [6-nitro-1,3-dioxo-benzo[de]isoquinolin-2-yl, N-methyl] | —(CH₂)₂—NH—(CH₂)₂— | 3-NO₂— | 1 | H | [N-formyl-1-methylpyrrole-2-carboxamido-1-methylpyrrole-2-carboxamido-ethyl-NH-acetyl chain] |
| 44 | [6-nitro-1,3-dioxo-benzo[de]isoquinolin-2-yl, N-methyl] | —(CH₂)₂—NH—(CH₂)₂— | 3-NO₂— | 1 | H | H |

TABLE 9-continued
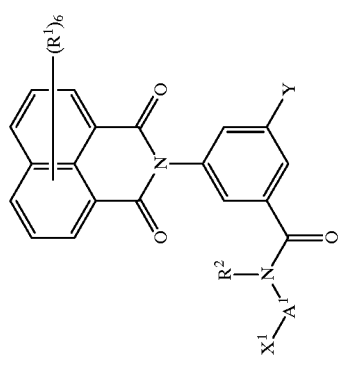
| Compound No. | X¹ | A¹ | R¹ | 1 | R² | Y |
|---|---|---|---|---|---|---|
| 45 | (structure) | —(CH₂)₃—NH—(CH₂)₂— (A) —(CH₂)₂—NH—(CH₂)₃— (B) | 3-NO₂— | 1 | H | H |

TABLE 10

| Compound No. | X¹ | A¹ | R¹ | l | R² | Y |
|---|---|---|---|---|---|---|
| 46 | 6-chloro-2-methyl-benzo[de]isoquinoline-1,3-dione | —(CH$_2$)$_2$—N(CH$_3$)—(CH$_2$)$_2$— | H | 1 | H | H |
| 47 | 6-nitro-2-methyl-benzo[de]isoquinoline-1,3-dione | —(CH$_2$)$_2$—NH—(CH$_2$)$_2$— | 3-NO$_2$— | 1 | H | —CONH—(CH$_2$)$_3$—N(CH$_3$)$_2$ |
| 48 | 6-nitro-2-methyl-benzo[de]isoquinoline-1,3-dione | —(CH$_2$)$_2$—NH—(CH$_2$)$_2$— | 3-NO$_2$— | 1 | H | —CONH—(CH$_2$)$_2$—N(CH$_3$)$_2$ |
| 49 | 6-nitro-2-methyl-benzo[de]isoquinoline-1,3-dione | —(CH$_2$)$_2$—NH—(CH$_2$)$_2$— | 3-NO$_2$— | 1 | H | —CONHCH$_3$ |
| 50 | 6-nitro-2-methyl-benzo[de]isoquinoline-1,3-dione | —(CH$_2$)$_2$—NH—(CH$_2$)$_2$— | H | 1 | H | —CONHCH$_3$ |

TABLE 11
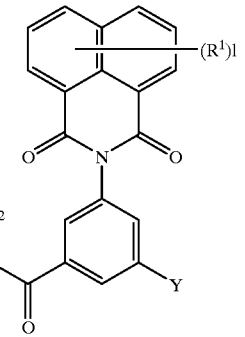
| Compound No. | X¹ | A¹ | R¹ | l | R² | Y |
|---|---|---|---|---|---|---|
| 51 | 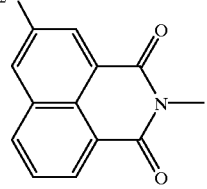 | —(CH$_2$)$_3$—NH—(CH$_2$)$_3$— | H | 1 | H | H |
| 52 | 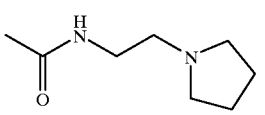 | —(CH$_2$)$_2$—NH—(CH$_2$)$_2$— | 3-NO$_2$— | 1 | H | 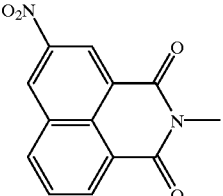 |
| 53 | 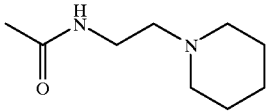 | —(CH$_2$)$_2$—NH—(CH$_2$)$_2$— | 3-NO$_2$— | 1 | H | 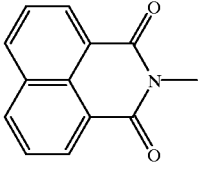 |
| 54 | 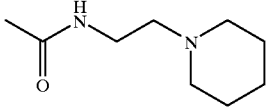 | —(CH$_2$)$_2$—NH—(CH$_2$)$_2$— | 3-NO$_2$— | 1 | H | 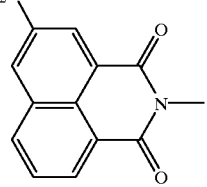 |
| 55 | 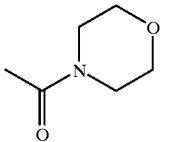 | —(CH$_2$)$_2$—NH—(CH$_2$)$_2$— | 3-NO$_2$— | 1 | H |  |

TABLE 12
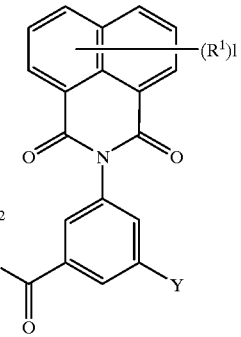
| Compound No. | X¹ | A¹ | R¹ | l | R² | Y |
|---|---|---|---|---|---|---|
| 56 | 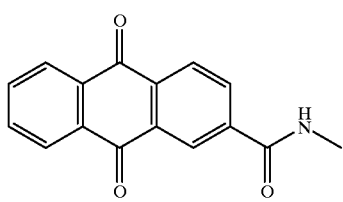 | —(CH$_2$)$_2$—NH—(CH$_2$)$_2$— | 3-NO$_2$— | 1 | H | 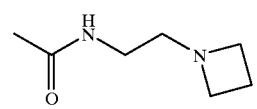 |
| 57 | 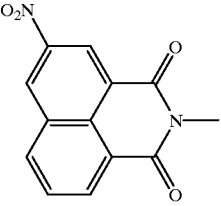 | —(CH$_2$)$_2$—NH—(CH$_2$)$_2$— | 3-NO$_2$— | 1 | H | 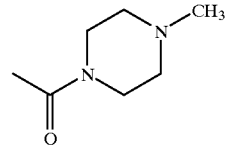 |
| 58 | 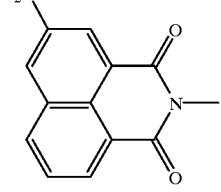 | —(CH$_2$)$_2$—NH—(CH$_2$)$_2$— | H | 1 | H | 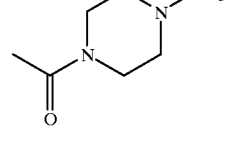 |
| 59 | 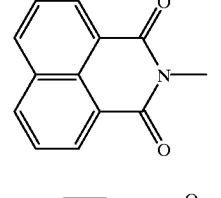 | —(CH$_2$)$_2$—NH—(CH$_2$)$_2$— | H | 1 | H | 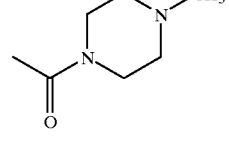 |
| 60 | 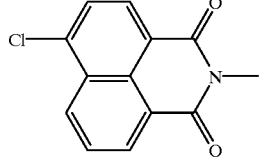 | —(CH$_2$)$_2$—NH—(CH$_2$)$_2$— | 3-NO$_2$— | 1 | H | 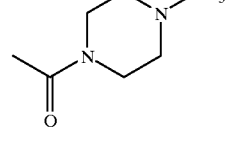 |

TABLE 13

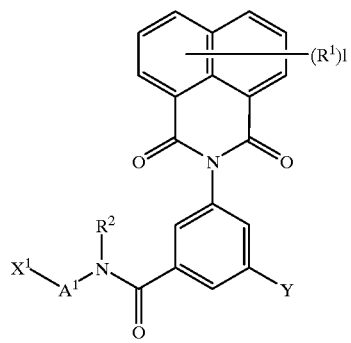

| Compound No. | X¹ | A¹ | R¹ | l | R² | Y |
|---|---|---|---|---|---|---|
| 61 | N-methyl naphthalimide | —(CH₂)₂—SO₂—(CH₂)₂— | 3-NO₂— | 1 | H | acetamido-ethyl-piperidinyl-dicyclopropylamine |
| 62 | N-methyl naphthalimide | —(CH₂)₂—NH—(CH₂)₂— | 3-NO₂— | 1 | H | acetyl-4-ethylpiperazine |
| 63 | 6-chloro-N-methyl naphthalimide | —(CH₂)₂—NH—(CH₂)₂— | 3-NO₂— | 1 | H | acetyl-4-ethylpiperazine |
| 64 | 6-nitro-N-methyl naphthalimide | —(CH₂)₂—NH—(CH₂)₂— | 3-NO₂— | 1 | H | acetyl-4-piperidinylpiperidine |
| 65 | 6-nitro-N-methyl naphthalimide | —(CH₂)₂—NH—(CH₂)₃— (A)<br>—(CH₂)₃—NH—(CH₂)₂— (B) | 3-NO₂— | 1 | H | acetyl-4-methylpiperazine |

TABLE 14

![Structure with R¹, R², X¹, A¹, Y substituents on naphthalimide-benzamide scaffold]

| Compound No. | X¹ | A¹ | R¹ | l | R² | Y |
|---|---|---|---|---|---|---|
| 66 | H-C(=O)-NH—[N-methyl pyrrole-2-CONH-] | —(CH₂)₂—NH—(CH₂)₂— | 3-NO₂— | 1 | H | —CONH—(CH₂)₄—N(CH₃)₂ |
| 67 | [N-methyl-naphthalimide] | —(CH₂)₂—NH—(CH₂)₂—NHCH₂— | H | 1 | H | H |
| 68 | [N-methyl-naphthalimide] | —(CH₂)₂—NH—(CH₂)₂—NHCH₂— | 3-NO₂— | 1 | H | —CON(CH₃)₂ |

The invention compounds represented by the formula (1) can be prepared, for example, by the processes as described below.

(A) when Y represents a hydrogen atom:

(A-1)

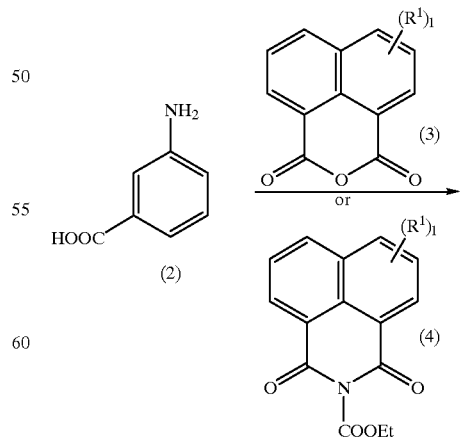

(Step 1)

-continued
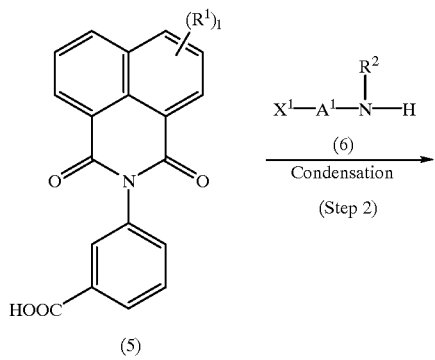
(5)
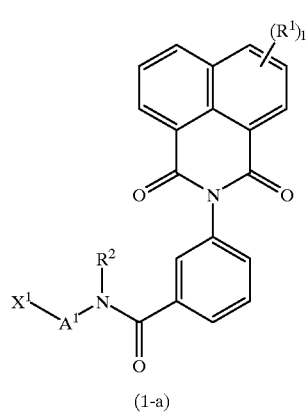
(1-a)
(wherein, $R^1$, $R^2$, l, $A^1$ and $X^1$ have the same meanings as described above, $Z^1$ represents a group forming $X^1$ as $NHCOZ^1$ and $Z^2$ represents a group forming $X^1$ as
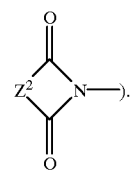
).
(B) When Y represents —C(=O)N($R^4$)—$A^2$—$X^2$ and —C(=O)—N($R^2$)—$A^1$—$X^1$ and —C(=O)—N($R^4$)—$A^2$—$X^2$ are the same
(B-1)
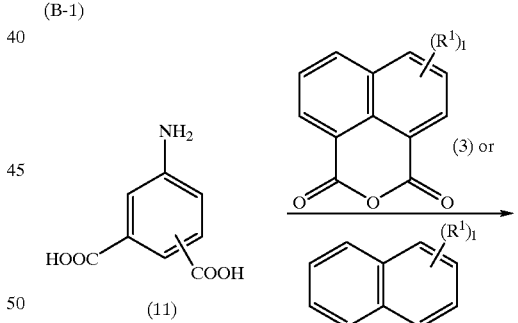
(wherein, $R^1$, $R^2$, l, $A^1$ and $X^1$ have the same meanings as described above).
(A-2)
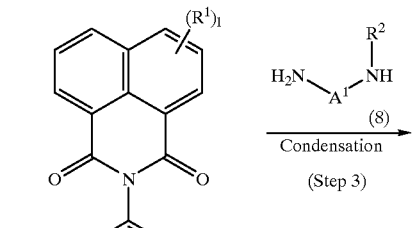
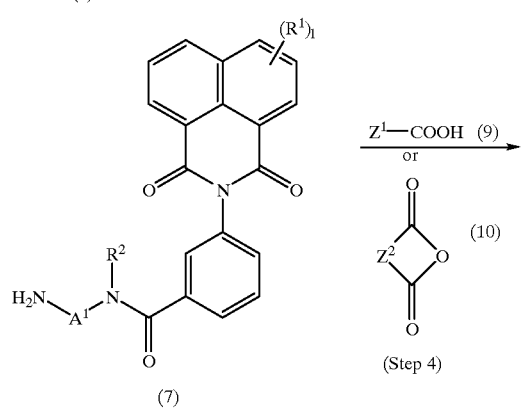

-continued
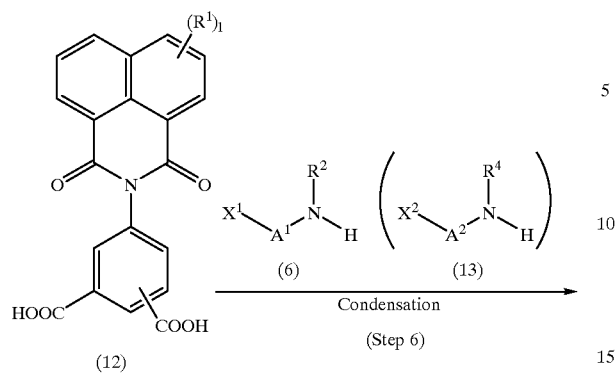
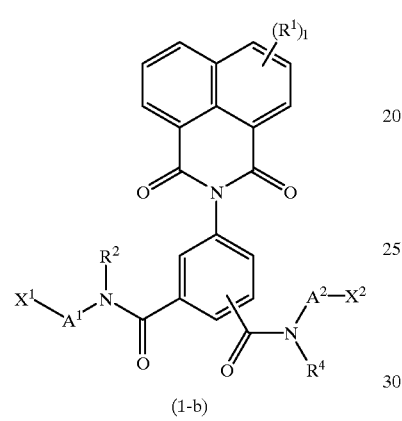
(wherein, $R^1$, $R^2$, l, $R^4$, $A^1$, $A^2$, $X^1$ and $X^2$ have the same meanings as described above).
(B-2)
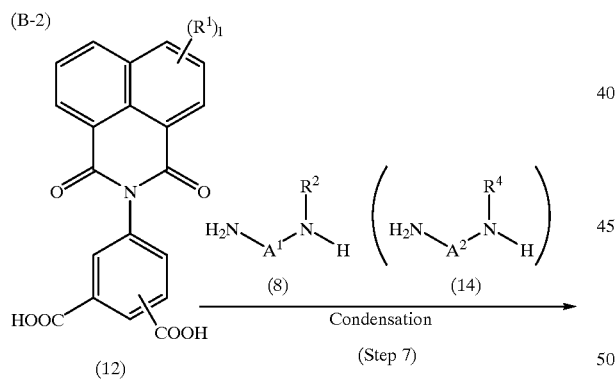
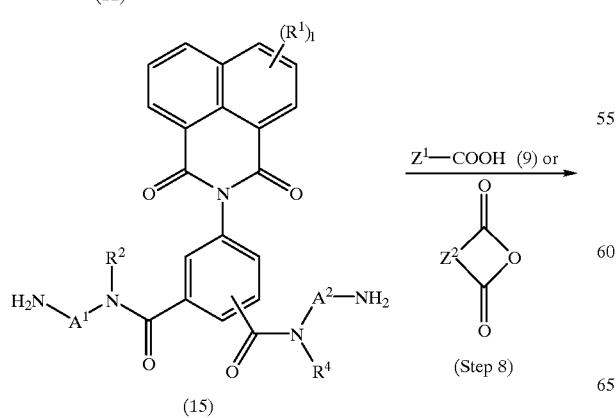
-continued
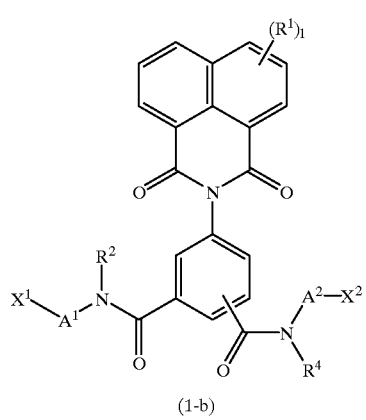
(wherein, $R^1$, $R^2$, l, $R^4$, $A^{1,}$ $A^2$, $X^1$, $X^2$, $Z^1$ and $Z^2$ have the same meanings as described above).
(C) When Y represents —C(=O)N($R^4$)—$A^2$—$X^2$ and —C(=O)—N($R^2$)—$A^1$—$X^1$ and —C(=O)—N($R^4$)—$A^2$—$X^2$ are not the same
(C-1)
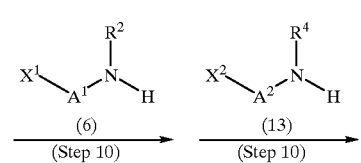
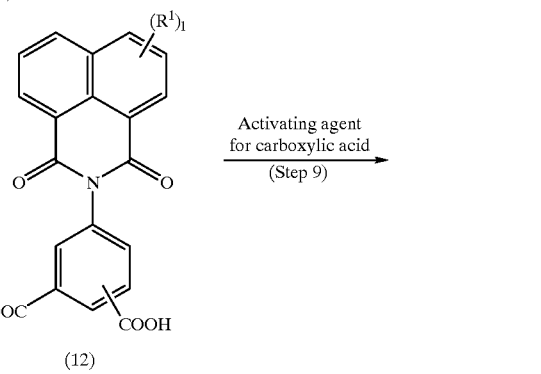

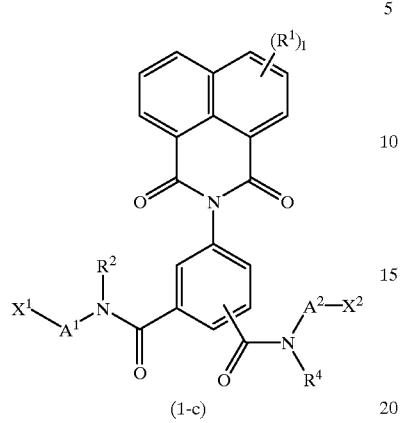

(1-c)

(wherein, $R^1$, $R^2$, l, $R^4$, $A^1$, $A^2$, $X^1$ and $X^2$ have the same meanings as described above and —C(=O)—D represents an activated carboxylic acid residue.)

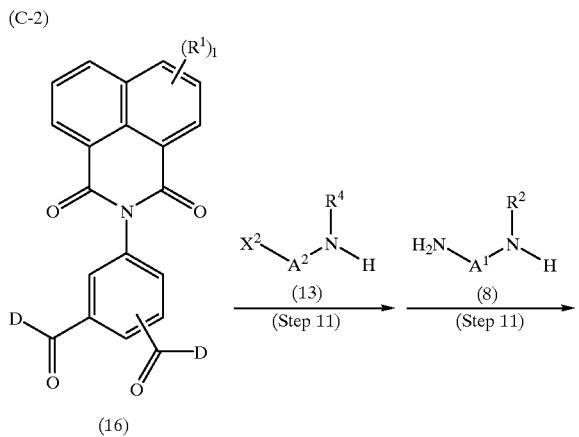

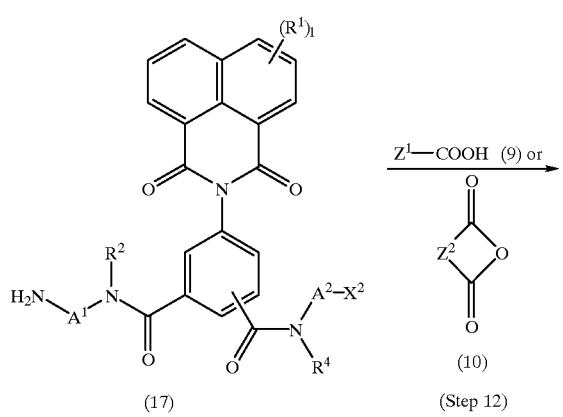

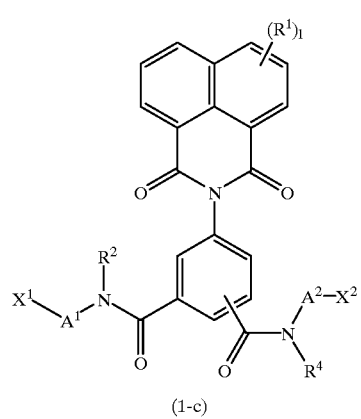

(1-c)

(wherein, $R^1$, $R^2$, l, $R^4$, $A^1$, $A^2$, $X^1$, $X^2$, —C(=C)—D, $Z^1$ and $Z^2$ have the same meanings as described above).

(Step 1)

An aminobenzenecarboxylic acid represented by the formula (2) is reacted with a compound represented by the formula (3) or (4) or an equivalent thereof, whereby a benzenecarboxylic acid derivative represented by the formula (5) can be obtained. This reaction is preferably conducted in a proper solvent. No particular limitation is imposed on the solvent insofar as it is inert to the reaction and examples include dichloromethane, chloroform, ethyl acetate, tetrahydrofuran, dioxane, diethyl ether, benzene, toluene, N,N-dimethylformamide, N,N-dimethylacetamide, dimethylsulfoxide and water. They may be used either singly or in combination. Upon reaction, a base may be used as needed. Examples of the base include organic amines such as trimethylamine, triethylamine, tripropylamine, diisopropylethylamine, N-methylmorpholine, N,N-dimethylaniline, pyridine, N,N-dimethylaminopyridine, lutidine and collidine and inorganic bases such as sodium bicarbonate, sodium carbonate and potassium carbonate. No particular limitation is imposed on the amount of the base insofar as it does not adversely affect the reaction. The base is preferably added in an amount 1 to 100 moles, particularly 1 to 10 moles, relative to 1 mole of the aminobenzenecarboxylic acid (2). The reaction is preferably carried out at 0 to 200° C., particularly, at 25 to 150° C. for 0.1 to 100 hours, particularly, for 0.5 to 20 hours.

(Step 2)

The resulting benzenecarboxylic acid (5) is condensed with a compound represented by the formula (6), whereby the corresponding naphthalimidobenzamide derivative represented by the formula (1-a) can be obtained. This reaction can be carried out in a known manner, generally, by activating a carboxylic acid by an activating agent and adding the compound (6) to the resulting activated carboxylic acid in a proper solvent to react them. Usable examples of the activating agent for a carboxylic acid include thionyl chloride, oxalyl chloride, phosphorus oxychloride, N,N- dicyclohexylcarbodiimide, 1-ethyl-3-(3-dimethylaminopropyl)carbodiimide hydrochloride, N,N'-carbonyldiimidazole, 2-chloro-1,3-dimethylimidazole chloride, pivaloyl chloride and trifluoroacetic anhydride. The compound (6) is usually added subsequent to the activation of the carboxylic acid, but it may be added simultaneously with the carboxylic acid and activating agent for the carboxylic acid. The activating agent for a carboxylic acid is preferably added in an amount of 1 to 100 moles, particularly 2 to 10 moles, relative to 1 mole of the benzenecarboxylic acid derivative (5). The compound (6) is preferably added in an amount of 1 to 100 moles, particularly 2 to 10 moles, relative to 1 mole of the benzene carboxylic acid derivative (5). Examples of the solvent usable in the present reaction include dichloromethane, chloroform, ethyl acetate, tetrahydrofuran, dioxane, diethyl ether, benzene, toluene, N,N-dimethylformamide, N,N-dimethylacetamide and dimethylsulfoxide. They may be used either singly or in combination. Upon reaction, a base may be used as needed. Examples of the base include organic amines such as trimethylamine, triethylamine, tripropylamine, diisopropylethylamine, N-methylmorpholine, N,N-dimethylaniline, pyridine, N,N-dimethylaminopyridine, lutidine and collidine and inorganic bases such as sodium bicarbonate, sodium carbonate and potassium carbonate. No particular limitation is imposed on the amount of the base insofar as it does not adversely affect the reaction. The base is preferably added in an amount 1 to 100 moles, particularly 1 to 20 moles, relative to 1 mole of the benzenecarboxylic acid derivative (5). The reaction is preferably carried out at 0 to 100° C., particularly, at 0 to 40° C. for hours similar to those of Step 1.

(Step 3)

The benzenecarboxylic acid derivative (5) is condensed with a compound represented by the formula (8), whereby the corresponding amino compound represented by the formula (7) can be obtained. This reaction can be carried out in a similar manner to the above-described Step 2. The compound (8) is preferably employed in an excess amount, particularly 5 to 50 times the mole. The amino compound (7) prepared in this reaction can be isolated and purified as needed, but can also be provided for the subsequent step without purification.

(Step 4)

The amino compound (7) is reacted with a carboxylic acid or a dicarboxylic anhydride represented by the formula (9) or (10) or equivalent thereof, whereby the corresponding naphthalimidobenzamide derivative (1-a) can be obtained. In this reaction, an activating agent for the carboxylic acid is added if necessary. The activating agent for the carboxylic acid, reaction solvent and base employed for this reaction are similar to those used in Step 2. The compound (9) or (10) is preferably added in an amount of 1 to 100 moles, particularly 1 to 10 moles, relative to 1 mole of the amino compound (7). The reaction temperature and time are similar to those of Step 1.

(Step 5)

Aminobenzenedicarboxylic acid represented by the formula (11) is reacted with a compound represented by the formula (3) or (4) or an equivalent thereof, whereby the corresponding benzenedicarboxylic acid derivative represented by the formula (12) can be obtained. This reaction can be carried out in a similar manner under similar condition to those of Step 1.

(Step 6)

The benzenedicarboxylic acid derivative (12) is condensed with a compound represented by the formula (6) or (13) [(6) and (13) are the same], whereby the corresponding naphthalimidobenzamide derivative represented by the formula (1-b) can be obtained. This reaction is carried out in a similar manner to Step 2.

(Step 7)

The benzenedicarboxylic acid derivative (12) is condensed with a compound of the formula (8) or (14) [(8) and (14) are the same], whereby the corresponding diamino compound represented by the formula (15) can be obtained. This reaction can be effected in a similar manner to Step 6, but it is preferred to use the compound (8) or (14) in an excess amount, particularly 5 to 50 times the mole.

(Step 8)

The diamino compound (15) is reacted with a carboxylic acid or a dicarboxylic anhydride represented by the formula (9) or (10) or equivalent thereof, whereby the corresponding naphthalimidobenzamide derivative (1-b) can be obtained. When the carboxylic acid (9) is used in this reaction, it is preferred to use an activating agent for the carboxylic acid as in Step 2. The reaction conditions are similar to those of Step 2. When the dicarboxylic acid anhydride (10) or equivalent thereof is employed in this reaction, on the other hand, the activating agent for the carboxylic acid is used if necessary. The activating agent for a carboxylic acid, reaction solvent and base employed in this reaction are similar to those of Step 2. The amount of the carboxylic acid (9) or dicarboxylic anhydride (10) is preferably added in an amount of 1 to 100 moles, particularly 2 to 20 moles relative to 1 mole of the diamino compound (15). The reaction temperature and time are similar to those of Step 1.

(Step 9)

The benzenedicarboxylic acid derivative (12) is reacted with a carboxylic-acid activating agent for a carboxylic acid, whereby the corresponding active ester compound represented by the formula (16) can be obtained. As examples of the carboxylic-acid activating agent, those exemplified in Step 2 can be mentioned. The carboxylic-acid activating agent is preferably added in an amount of 1 to 100 moles, particularly 2 to 10 moles relative to 1 mole of the benzenedicarboxylic acid derivative (12). As examples of the solvent usable in this reaction, those exemplified in Step 2 can be mentioned. They may be used either singly or in combination. Upon reaction, a base may be used as needed. Examples of the base include organic amines such as trimethylamine, triethylamine, tripropylamine, diisopropylethylamine, N-methylmorpholine, N,N-dimethylaniline, pyridine, lutidine and collidine and inorganic bases such as sodium bicarbonate and sodium carbonate. Although no particular limitation is imposed on the amount of the base insofar as it does not adversely affect the reaction, it is preferred to add it in an amount of 1 to 100 moles, particularly 2 to 10 moles relative to 1 mole of the benzenedicarboxylic acid derivative (12). The reaction temperature is similar to that of Step 2, while the reaction time is similar to that of Step 1. The active ester compound (16) prepared in this reaction can be isolated and purified as needed, but can also be provided for the subsequent step without purification.

(Step 10)

The active ester compound (16) is reacted with the compound (6), followed by reaction with the compound (13), whereby the corresponding naphthalimidobenzamide derivative (1-c) can be obtained. This reaction is preferably carried out in a proper solvent. No particular limitation is imposed on the solvent insofar as it is inert to the reaction. Those exemplified in Step 2 can be mentioned as examples of the solvent. They may be used either singly or in combination. Upon reaction, a base may be used as needed. As the base, those exemplified in Step 2 can be mentioned as examples. Although no particular limitation is imposed on the amount of the base insofar as it does not adversely affect the reaction, the amount is preferably 1 to 100 moles, particularly 1 to 10 moles, relative to 1 mole of the active ester compound (16). Relative to 1 mole of the active ester compound (16), the compound (6) is preferably added in an amount of 0.5 to 5 moles, particularly 1 to 2 moles and the compound (13) is preferably added in an amount of 1 to 50 moles, particularly 1 to 10 moles. The reaction temperature is similar to that in Step 2. The reaction times after the addition of the compound (6) and the compound (13) are each preferably 0.1 to 100 hours, particularly 0.5 to 5 hours.
(Step 11)

The active ester compound (16) is reacted with the compound (13) and then with the compound (8), whereby the corresponding compound of the formula (17) can be obtained. This reaction is preferably conducted in a proper solvent. No particular limitation is imposed on the solvent insofar as it is inert to the reaction. As examples of the solvent, those exemplified above in Step 2 can be mentioned. They may be used either singly or in combination. Upon reaction, a base may be added as needed. As examples of the base, those exemplified above in Step 2 can be mentioned. Although no particular limitation is imposed on the amount of the base insofar as it does no adversely affect the reaction, the base is preferably added in an amount of 1 to 100 moles, particularly 1 to 10 moles per mole of the active ester compound (16) employed. Relative to 1 mole of the active ester compound (16), the compound (13) is preferably added in an amount of 0.5 to 5 moles, particularly 1 to 2 moles, while the compound (8) is preferably added in an amount of 2 to 100 moles, particularly 5 to 50 moles. The reaction temperature is similar to that in Step 2. The reaction times after the addition of the compound (13) and the compound (8) are each preferably 0.1 to 100 hours, particularly 0.5 to 5 hours. The compound (17) synthesized in this reaction can be isolated and purified as needed, but can also be provided for the subsequent step without purification.
(Step 12)

The compound (17) is reacted with the carboxylic acid (9) or dicarboxylic anhydride (10), whereby the corresponding naphthalimidobenzamide derivative (1-c) can be obtained. When the carboxylic acid (9) is employed in this reaction, it is preferred to add a carboxylic-acid activating agent as in Step 2. When the dicarboxylic anhydride (10) or equivalent thereof is employed in this reaction, on the other hand, the carboxylic-acid activating agent is used if necessary. The activating agent, reaction solvent and base employed in this reaction are similar to those of Step 2. The carboxylic acid (9) or dicarboxylic anhydride (10) is preferably added in an amount of 1 to 50 moles, particularly 1 to 10 moles relative to 1 mole of the compound (17). The reaction temperature and reaction time are similar to those of Step 2.

The naphthalimidobenzamide derivatives (1) of the present invention or intermediates thus obtained can be converted into salts, particularly pharmaceutically acceptable salts, in a known manner.

These compounds can be isolated and purified by known separating and purifying means, such as concentration, solvent extraction, filtration, recrystallization or various chromatographies.

The naphthalimidobenzamide derivatives (1) or salts thereof according to the present invention are compounds synthesized to have a high affinity with DNA and base sequence selectivity. As a result of various investigations, it has been confirmed that the compounds of the present invention each has a high affinity with DNA based on the results of various tests including a test using ethidium bromide displacement assay or the like. It has also been confirmed that they have stronger affinities with respective base sequence regions. For example, the compound of Example 4 has strong interaction with a region abundant in guanine and cytosine, while the compound of Example 30 has strong interaction with a region abundant in adenine and thymine.

A compound having interaction with DNA exhibits its biological activity in the following two manners.

One is a manner of inhibiting the action of an enzyme on DNA. Examples include functional inhibition of topoisomerase, helicase, DNA repair enzyme or DNA polymerase. The compound of the present invention is confirmed to inhibit the activity of topoisomerase.

The other one is a manner of inhibiting the binding of a transcription-related protein to DNA, thereby exhibiting biological activity. In general, a transcription-related protein has selective interaction with a specific region or a specific base sequence in DNA, thereby adjusting transcription and then controlling the production of a specific protein. It is therefore presumed that a compound which binds to a specific region or a specific base sequence can selectively control the synthesis of a limited protein through inhibition of protein-DNA binding. Judging from that diseases including malignant tumor are induced by the abnormal exhibition amount of a specific protein, the compounds of the present invention which are bound to DNA with base-sequence selectivity and high affinity are usable as a remedy for many diseases with high selectivity. Examples of such diseases include malignant tumors, immune.allergic diseases, circulatory diseases, respiratory diseases, digestive diseases, hepatic.biliary diseases, musculoskeletal.connective-tissue diseases, endocrine diseases, neuropathy, psychiatric diseases, urinary.genital diseases, obstetric and gynecologic diseases and skin diseases.

The compounds of the present invention can be used as a pharmaceutical for various diseases, more preferably, an antitumor agent, particularly preferably an anti-malignant tumor agent. Examples of the malignant tumor include head and neck cancer, esophageal carcinoma, gastric cancer, colon cancer, rectum cancer, liver cancer, gallbladder.bile duct cancer, pancreatic cancer, lung cancer, breast cancer, ovarian cancer, bladder cancer, prostatic cancer, osteosarcoma.soft tissue sarcoma, malignant lymphoma, leukemia, cervical cancer, skin carcinoma and brain tumor.

The compounds of the present invention exhibited excellent antitumor effects in a test using a nude mouse to which human cancer cell strains had been subcutaneously transplanted. For example, the compound of Example 46 exhibited inhibitory effects against tumor proliferation by 96.2%, 59.8%, 71.8% and 79.5% in systems to which human skin cancer strains LOX, human pancreatic cancer strains PAN6, human breast cancer strains MX1 and human gastric cancer strains AZ521 had been transplanted, respectively.

Upon use of each of the compounds of the present invention as a pharmaceutical, it is mixed with a pharmaceutically acceptable carrier as needed, depending on what purpose it is applied, that is, prevention or remedy and then administered through various administration routes as an oral agent, injection, suppository, ointment, plaster or the like.

For the formulation of an orally-dosable solid preparation, the invention compound may be added with an excipient and optionally with a binder, disintegrator, lubricant, colorant and/or taste corrigent.smell corrigent and the resulting mixture can then be formed into tablets, coated tablets, granules, powder or capsules in a conventional manner. As such additives, those commonly employed in this field can be used. Examples of the excipient include lactose, sucrose, sodium chloride, glucose, starch, calcium carbonate, kaolin, fine crystalline cellulose and silicic acid; those of the binder include water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; those of the disintegrator include dried starch, sodium alginate, agar powder, sodium bicarbonate, calcium carbonate, sodium laurylsulfate, stearic monoglyceride and lactose; those of the lubricant include purified talc, stearates, sodium borate and polyethylene glycol; those of the colorant include titanium oxide and iron oxide; and those of the taste.smell corrigent include sucrose, bitter orange peel, citric acid and tartaric acid.

For the formulation of an orally-dosable liquid preparation, the invention compound may be added with a taste corrigent, buffer, stabilizer, smell corrigent and/or the like and then the resulting mixture can be formed into mixtures for internal use, syrups or elixirs in a conventional manner. The taste.smell corrigents exemplified above in the orally dosable solid preparation can also be used for liquid preparations. Examples of the buffer include sodium citrate and those of the stabilizer include tragacanth, acacia and gelatin.

For the formulation of an injection, the invention compound may be added with a pH adjuster, buffer, stabilizer, tonicity agent, local anesthetic and/or the like and then the resulting mixture can be formed into a subcutaneous injection, intramuscular injection or intravenous injection in a conventional manner. Illustrative pH adjusters and buffers include sodium citrate, sodium acetate and sodium phosphate. Examples of the stabilizer include sodium pyrosulfite, EDTA, thioglycolic acid and thiolactic acid. Exemplary local anesthetics include procaine hydrochloride and lidocaine hydrochloride. Examples of the tonicity agent include sodium chloride and glucose.

For the formulation of suppositories, the invention compound may be added with a known pharmaceutically-acceptable carrier such as polyethylene glycol, lanolin, cacao butter or fatty triglyceride and optionally with a surfactant such as polyoxyethylenesorbitan fatty acid ester, followed by formation of the resulting mixture into suppositories in a conventional manner.

For the formulation of an ointment, the invention compound may be added with a base, a stabilizer, a humectant, preservative and/or the like, which are generally employed for an ointment, as needed and they are mixed and formed into an ointment in a conventional manner. Examples of the base include liquid paraffin, white petrolatum, white beeswax, octyldodecyl alcohol and paraffin; and those of the preservative include methyl paraoxybenzoate, ethyl paraoxybenzoate and propyl paraoxybenzoate.

For the formulation of a plaster, the above-described ointment, cream, gel or paste may be coated on a usually-employed backing material. Suitable examples of the backing material include woven fabrics of cotton, rayon or chemical fibers, nonwoven fabrics and films or foamed sheets of soft polyvinyl chloride, polyethylene or polyurethane.

The amount of the invention compound to be incorporated in each of the above-described dosage forms varies depending on the conditions of the patient or the dosage form. In general, it is desired to incorporate the invention compound in an amount of about 1 to 1000 mg, particularly 2 to 500 mg, in an orally-dosable preparation, about 0.1 to 500 mg, particularly 0.2 to 300 mg in an injection and about 5 to 1000 mg, particularly 10 to 500 mg, in a suppository. The daily dose of the pharmaceutical in the above dosage form varies depending on the conditions, body weight, age and sex of the patient and cannot be determined in any wholesale manner. In general, the daily dose may be about 0.1–5000 mg, preferably, about 1 to 1000 mg per adult. It is desired to conduct administration once or in 2 to 4 portions a day.

EXAMPLES

The present invention will hereinafter be described more specifically by Examples. It is, however, to be borne in mind that the present invention is by no means limited to or by them.

Referential Example 1

Synthesis of 5-(1,8-naphthalimido)isophthalic acid

To a mixture of 40 ml of dimethylsulfoxide and 10 ml of pyridine were added 3.62 g (20 mmol) of 5-aminoisophthalic acid and 3.96 g (20 mmol) of 1,8-naphthalic anhydride. The resulting mixture was stirred at 100° C. for 14 hours. After cooling to room temperature, the reaction mixture was added with 100 ml of ethyl acetate and crystals so precipitated were collected by filtration. The crystals were washed with ethyl acetate and then dried, whereby 4.23 g (58.5%) of the title compound was obtained. The physical properties of the resulting compound are as follows.

$^1$H-NMR(DMSO-$d_6$-$D_2O$) δ: 7.92(2H,t,J=7.7 Hz), 8.25 (2H,d,J=1.7 Hz), 8.50–8.58(5H,m).

Referential Example 2

Synthesis of 5-(1,8-naphthalimido)isophthaloyl diimidazole

To a suspension of 3.12 g (8.64 mmol) of the isophthalic acid derivative in dimethyl sulfoxide (43.2 ml), which had been prepared in the process as described in Referential Example 1, was added 3.08 g (19.0 mmol) of N,N'-carbonyldiimidazole, followed by stirring at 50° C. for 30 minutes. The reaction mixture was diluted with 50 ml of tetrahydrofuran and allowed to stand overnight. The crystals thus precipitated were collected by filtration under reduced pressure and washed with tetrahydrofuran, whereby 1.20 g (26.0%) of the title compound was obtained. The physical properties of the resulting compound are as follows:

$^1$H-NMR(DMSO-$d_6$-$D_2O$) δ: 7.20(2H,brs), 7.80(2H,brs), 7.93(2H,t,J=7.8 Hz), 8.31–8.37(5H,m), 8.52–8.58(4H,m).

Referential Example 3

Synthesis of N-[2-[(2-aminoethyl)amino]ethyl]-3-nitro-1,8-naphthalimide dihydrochloride In ethanol (200 ml) was suspended 24.3 g (0.1 mol) of 3-nitro-1,8-naphthalic anhydride, followed by the dropwise addition to a solution of 103 g (1.0 mol) of diethylene triamine in ethanol (100 ml) under ice cooling. The mixture was stirred at room temperature for 30 minutes. Under ice cooling, concentrated hydrochloric acid (250 ml) was added dropwise, followed by stirring at room temperature for 1 hour. The precipitate thus formed was collected by filtration and suspended in 600 ml of water. The resulting suspension was heated under reflux for 30 minutes. After cooling to room temperature, the resulting crystals were collected by filtration under reduced pressure, washed with water and then dried, whereby 24.2 g (60.3%) of the title compound was obtained. The physical properties of the resulting compound are as follows:

$^1$H-NMR(DMSO-d$_6$-D$_2$O) δ: 3.34–3.41(4H,m), 3.47(2H, t,J=5.8 Hz), 4.53(2H,t,J=5.8 Hz), 8.04(1H,dd,J=7.6,8.3 Hz), 8.64(1H,d,J=8.3 Hz), 8.77(1H,d,J=7.3 Hz), 9.21(1H,d,J=2.4 Hz), 9.36(1H,d,J=2.2 Hz).

Referential Example 4

Synthesis of 1,3-bis[N-[2-[(2-aminoethyl)amino] ethyl]carbamoyl]-5-(3-nitro-1,8-naphthalimido) benzene tetrahydrochloride To a suspension of 4.06 g (10.0 mmol) of 5-(3-nitro-1,8-naphthalimido)isophthalic acid in N,N-dimethylacetamide (20 ml) was added 3.24 g (20.0 mmol) of N,N'-carbonyldiimidazole. The resulting mixture was stirred at 50° C. for 30 minutes. The reaction mixture was added dropwise to a solution of 10.3 g (100 mmol) of diethylenetriamine in N,N-dimethylacetamide (20 ml) under ice cooling. After stirring at 0° C. for 15 minutes, the reaction mixture was added with 6N hydrochloric acid (60 ml) under cooling. The reaction mixture was washed several times with chloroform. The water layer was purified by reversed phase column chromatography (CHP-20P/mobile phase; water). The eluate containing the target compound was concentrated and then, lyophilized, whereby 4.92 g (68.1%) was obtained. The physical properties of the resulting compound are as follows:

$^1$H-NMR(DMSO-d$_6$-D$_2$O) δ: 3.18–3.30(12H,m), 3.63–3.69(4H,m), 8.07–8.13(3H,m), 8.69(1H,dd,J=1.0,7.3 Hz), 8.82–8.86(2H,m), 8.96(1H,d,J=2.2 Hz), 9.03–9.08(2H, m), 9.53(1H,d,J=2.2 Hz).

IR(KBr)cm$^{-1}$: 1714, 1670, 1598, 1541, 1421, 1342, 1248

Referential Example 5

Synthesis of 3-[4-[4-[4-(benzyloxycarbonylamino) butylamido]-1-methylpyrrole-2-carbonylamino]-1-methylpyrrole-2-carbonylamino] dimethylaminopropane In a mixed solvent of methanol (20 ml) and tetrahydrofuran (5 ml) was dissolved 1.51 g (4.0 mmol) of 3-[1-methyl-4-(1-methyl-4-nitropyrrole-2-carbonylamino) pyrrole-2-carbonylamino]dimethylaminopropane described in "Heterocycles, 27, 1945–1952(1988)". The resulting solution was subjected to catalytic reduction using platinum oxide as a catalyst at room temperature for 2 hours under a hydrogen atmosphere of about 3 atmospheric pressure. After completion of the reaction, the catalyst was filtered off and the residue was concentrated under reduced pressure. The residue thus obtained was dissolved in N,N-dimethylformamide (5 ml). At room temperature, the resulting solution was added dropwise to a solution obtained by stirring, at 5° C. for 30 minutes, 1.19 g (5.0 mmol) of 4-(benzyloxycarbonylamino)butyric acid and 0.81 g (5.0 mmol) of N,N'-carbonyldiimidazole in tetrahydrofuran (10 ml). The resulting mixture was stirred overnight at room temperature. The reaction mixture was diluted with ethyl acetate, washed with water and saturated saline and then dried over sodium sulfate. The solution was concentrated under reduced pressure. The crude product thus obtained was recrystallized from ethyl acetate (10 ml)-hexane (1 ml), whereby 830 mg (36.7%) of the title compound was obtained. The physical properties of the resulting compound are as follows:

Melting point: 160 to 163° C.

$^1$H-NMR(DMSO-d$_6$-D$_2$) δ: 1.58–1.76(4H,m), 2.15(6H, s), 2.20–2.25(4H,m), 3.00–3.08(2H,m), 3.15–3.22(2H,m), 3.79(3H,s), 3.82(3H,s), 5.01(2H,s), 6.81(1H,d,J=2.0 Hz), 6.85(1H,d,J=1.7 Hz), 7.15(1H,d,J=1.7 Hz), 7.18(1H,d,J=2.0 Hz), 7.26–7.40(6H,m), 8.06(1H,t,J=5.7 Hz), 9.80(1H,brs), 9.85(1H,brs).

In a similar manner, the following compounds were obtained.

Referential Example 6

3-(4-Phthalimidoacetamido-1-methylpyrrole-2-carbonylamino)dimethylaminopropane

The physical properties of this compound are as follows:

$^1$H-NMR(DMSO-d$_6$-D$_2$O) δ: 1.55–1.63(2H,m), 2.14(6H, s), 2.19–2.24(2H,m), 3.13–3.19(2H,m), 3.76(3H,s), 4.36 (2H,s), 6.67(1H,d,J=1.7 Hz), 7.05(1H,brs), 7.86–8.06(5H, m), 10.14(1H,brs).

Referential Example 7

3-(3-Phthalimidopropionamido-1-methylpyrrole-2-carbonylamino)dimethylaminopropane The physical properties of this compound are as follows:

$^1$H-NMR(DMSO-d$_6$-D$_2$O) δ: 1.53–1.60(4H,m), 2.11(6H, s), 2.18–2.21(2H,t,J=7 Hz), 2.60(2H,t,J=7 Hz), 3.15(2H,q, J=7 Hz), 3.74(3H,s), 3.84(2H,t,J=7 Hz), 6.58(1H,d,J=1.7 Hz), 7.04(1H,d,J=1.7 Hz), 7.80–7.88(6H,m), 8.03(1H,t,J= 5.5 Hz), 9.87(1H,brs).

Referential Example 8

3-[4-[4-(Benzyloxycarbonylamino)butyramido]-1-methylpyrrole-2-carbonylamino] dimethylaminopropane The physical properties of this compound are as follows:

Melting point: 118 to 119° C.

$^1$H-NMR(DMSO-d$_6$-D$_2$O) δ: 1.53–1.71(4H,m), 2.10(6H, s), 2.18–2.23(4H,m), 2.97–3.03(2H,m), 3.12–3.18(2H,m), 3.74(3H,s), 4.98(2H,s), 6.59(1H,d,J=1.7 Hz), 7.18(1H,d,J= 2.0 Hz), 7.24–7.38(6H,m), 8.05(1H,t,J=5.7 Hz), 9.74(1H, brs).

Referential Example 9

3-[4-[4-[(Benzyloxycarbonylamino)acetamido]-1-methylpyrrole-2-carbonylamino]-1-methylpyrrole-2-carbonylamino]dimethylaminopropane The physical properties of this compound are as follows:

$^1$H-NMR(DMSO-d$_6$-D$_2$O) δ: 1.57–1.62(2H,m), 2.13(6H, s), 2.23–2.25(2H,m), 3.14–3.20(2H,m), 3.73(2H,d,J=6 Hz), 3.78(3H,s), 3.82(3H,s), 5.04(2H,s), 6.80(1H,d,J=1.9 Hz), 6.88(1H,d,J=1.7 Hz), 7.14(1H,d,J=1.7 Hz), 7.17(1H,d,J=1.7 Hz), 7.20–7.40(6H,m), 7.51(1H,t,J=5.7 Hz), 8.05(1H,t,J= 5.7 Hz), 9.85(1H,brs), 9.87(1H,brs).

Referential Example 10

3-[4-[4-[3-(Benzyloxycarbonylamino) propionamido]-1-methylpyrrole-2-carbonylamino]-1-methylpyrrole-2-carbonylamino] dimethylaminopropane The physical properties of this compound are as follows:

Melting point: 197 to 198° C.

$^1$H-NMR(DMSO-d$_6$-D$_2$O) δ: 1.72–1.80(2H,m), 2.33(6H, s), 2.50–2.55(4H,m), 3.40–3.56(4H,m), 3.89(6H,s), 5.08 (2H,s), 6.52(1H,brs), 6.57(1H,brs), 7.05–7.35(7H,m), 7.63 (1H,brs), 7.68(1H,brs), 7.90(1H,brs), 7.98(1H,brs).

Referential Example 11

3-[4-[4-[5-(Benzyloxycarbonylamino)
pentanoamido]-1-methylpyrrole-2-carbonylamino]-
1-methylpyrrole-2-carbonylamino]
dimethylaminopropane The physical properties of this compound are as follows:
Melting point: 172 to 175° C.
$^1$H-NMR(DMSO-d$_6$-D$_2$O) δ: 1.39–1.62(6H,m), 2.13(6H, s), 2.19–2.26(4H,m), 2.97–3.02(2H,m), 3.14–3.20(2H,m), 3.78(3H,s), 3.80(3H,s), 4.99(2H,s), 6.79(1H,d,J=2.0 Hz), 6.83(1H,d,J=1.7 Hz), 7.13(1H,d,J=1.7 Hz), 7.16(1H,d,J=2.0 Hz), 7.23–7.38(6H,m), 8.05(1H,t,J=5.7 Hz), 9.76(1H,brs), 9.83(1H,brs).

Referential Example 12

Synthesis of 1-[N-[2-[(2-aminoethyl)amino]ethyl]
carbamoyl]-3-(3-nitro-1,8-naphthalimido)-5-[N-[2-
[[2-(3-nitro-1,8-naphthalimido))ethyl]amino]ethyl]
carbamoyl]benzene trihydrochloride To a suspension of 10.0 g (13.8 mmol) of the compound obtained in Referential Example 4 in N,N-dimethylformamide (20 ml) were added triethylamine (14 ml) and then 1.22 g (5.0 mmol) of 3-nitro-1,8-naphthalic anhydride at room temperature. The resulting mixture was reacted at 60° C. for 1 hour. After concentration of the reaction mixture to remove excess triethylamine, the resulting suspension was added with 1N hydrochloric acid, followed by purification through reversed phase column chromatography (CHP-20P/mobile phase; water:acetonitrile= 85:15). The eluate containing the target compound was concentrated and then lyophilized, whereby 2.20 g (17.5%) of the title compound was obtained. The physical properties of the resulting compound are as follows:
$^1$H-NMR(DMSO-d$_6$-D$_2$O) δ: 3.10–3.26(8H,m), 3.34–3.42(2H,m), 3.54–3.67(4H,m), 4.36–4.46(2H,m), 7.96–8.04(2H,m), 8.07–8.14(2H,m), 8.62–8.73(4H,m), 8.85 (1H,d,J=8.3 Hz), 8.95(1H,d,J=2.2 Hz), 8.96(1H,d,J=2.2 Hz), 9.40(1H,d,J=2.2 Hz), 9.55(1H,d,J=2.2 Hz).
IR(KBr)cm$^{-1}$: 1713, 1669, 1599, 1540, 1510, 1421, 1342, 1247

Referential Example 13

Synthesis of 1-[N-[2-[(2-aminoethyl)amino]ethyl]
carbamoyl]-3-[N-[3-[N-[2-[N-[2-[N-(3-
dimethylaminopropyl)carbamoyl]-1-methylpyrrol-4-
yl]carbamoyl]-1-methylpyrrol-4-yl]carbamoyl]
propyl]carbamoyl]-5-(3-nitro-1,8-naphthalimido)
benzene trihydrochloride In methanol (30 ml) was dissolved 1.13 g (2.0 mmol) of the compound obtained above in Referential Example 5. The resulting solution was subjected to catalytic reduction at room temperature for 4 hours in the presence of palladium carbon as a catalyst under a hydrogen atmosphere of about 4 atmospheric pressure. After completion of the reaction, the catalyst was filtered off and the solution was concentrated under reduced pressure. The resulting residue was dissolved in N,N-dimethylformamide (3 ml), followed by the dropwise addition to a solution of unpurified 5-(3-nitro-1,8-naphthalimido)isophthaloyl diimidazole (2.4 mmol), which had been obtained in accordance with the process described in Referential Example 2, in N,N-dimethylformamide (5 ml) at room temperature. The reaction mixture was stirred at room temperature for 15 minutes, followed by the addition to a solution of 2.06 g (20.0 mmol) of diethylene triamine in N,N-dimethylformamide (5 ml) at room temperature. The mixture was stirred for further 15 minutes at room temperature. After cooling, 6N hydrochloric acid (12 ml) was added to the mixture and the mixture was purified by reversed phase column chromatography (CHP-20P/mobile phase; water:acetonitrile=95:5). The eluate containing the target compound was concentrated and lyophilized, whereby 862 mg (44.5%) of the title compound was obtained. The physical properties of the resulting compound are as follows:
$^1$H-NMR(DMSO-d$_6$-D$_2$O) δ: 1.84–1.90(4H,s), 2.33–2.36 (2H,s), 2.78(6H,s), 3.05–3.40(12H,m), 3.64–3.70(2H,m), 3.82(6H,s), 6.86(1H,d,J=14.9 Hz), 7.13(1H,s), 8.05–8.14 (2H,m), 8.60–8.84(4H,m), 9.00(1H,s), 9.52(1H,s), 9.85(1H, s), 9.94(1H,s)
IR(KBr)cm$^{-1}$: 1668, 1664, 1652, 1649, 1598, 1592, 1540, 1436

Referential Example 14

Synthesis of 9-[2-[2-aminoethyl(triphenylmethyl)
amino]ethyl]-9H-pyrido[3,4-b]indole To a solution of 506 mg (3.01 mmol) of norharman in N,N-dimethylformamide (15 ml) was added 132 mg (3.3 mmol) of sodium hydride in small portions under ice cooling, followed by stirring at room temperature for 30 minutes. To the reaction mixture was added 3.84 g (10 mmol) of bis(2-chloroethyl)(triphenylmethyl)amine and the mixture was reacted at 110° C. for 3 hours. Then, 650 mg (10 mmol) of sodium azide was added, followed by reaction at 100° C. for 2 hours. After cooling to room temperature, the resulting suspension was diluted with toluene and then washed with water and saturated saline. The toluene layer was dried over sodium sulfate and then concentrated under reduced pressure. The residue was added with tetrahydrofuran (3 ml) and water (1 ml) to dissolve the former in the latter. To the resulting solution was added 787 mg (3.0 mmol) of triphenylphosphine and the mixture was reacted at 50° C. for 2 hours. Generation of a gas was observed for a while after the initiation of the reaction and it lasted for about 1.5 hours. After completion of the reaction, the reaction mixture was concentrated, followed by purification through chromatography on a silica gel column (mobile phase; chloroform:methanol:aqueous ammonia=90:9.7:0.3 (v/v)), whereby 306 mg (20.5%) of the title compound was obtained. The physical properties of the resulting compound are as follows:
$^1$H-NMR(DMSO-d$_6$-D$_2$O) δ: 2.50–2.60(2H,m), 2.80–2.88(2H,m), 3.14–3.20(2H,m), 4.60–4.66(2H,m), 7.15–7.57(14H,m), 7.90(1H,dd,J=1.0,5.1 Hz), 8.09(1H,d,J= 7.8 Hz), 8.39(1H,d,5.1 Hz), 8.60(1H,d,J=1.0 Hz).

Referential Example 15

Synthesis of 3-(3-nitro-1,8-naphthalimido)benzoic
acid

To a mixture of dimethylsulfoxide (40 ml) and pyridine (10 ml) were added 3.02 g (22 mmol) of 3-aminobenzoic acid and 4.86 g (20 mmol) of 3-nitro-1,8-naphthalic anhydride. The resulting mixture was stirred at 100° C. for 2 hours. After cooling to room temperature, the reaction mixture was added with 200 ml of ethyl acetate and the crystals so precipitated were collected by filtration. The crystals were washed with ethyl acetate and then dried, whereby 6.06 g (83.6%) of the title compound was obtained. The physical properties of the resulting compound are as follows:

$^1$H-NMR(DMSO-d$_6$-D$_2$O) δ: 7.69(2H,dd,J=4.4,3.7 Hz), 8.03–8.12(3H,m), 8.69(1H,d,J=7.3 Hz), 8.83(1H,d,J=8.3 Hz), 8.96(1H,s), 9.54(1H,s), 13.16(1H,brs).

Referential Example 16

Synthesis of a mixture of 1-[N-[2-[(3-aminopropyl)amino]ethyl]carbamoyl]-3-(3-nitro-1,8-naphthalimido)benzene hydrochloride and 1-[N-[3-[(2-aminoethyl)amino]propyl]carbamoyl]-3-(3-nitro-1,8-naphthalimido)benzene hydrochloride To a suspension of 1.09 g (3.0 mmol) of the compound obtained above in Referential Example 15 in N,N-dimethylformamide (3 ml) was added 0.487 g (3.0 mmol) of N,N'-carbonyldiimidazole and the resulting mixture was stirred at 50° C. for 30 minutes. The reaction mixture was added to a solution of 1.05 g (9.0 mmol) of N-(2-aminoethyl)-1,3-propanediamine in N,N-dimethylformamide (3 ml), followed by stirring at room temperature for 30 to minutes. To the reaction mixture was added 6N hydrochloric acid (10 ml) under ice cooling and the mixture was purified by reversed phase column chromatography (CHP-20P/mobile phase; water:acetonitrile= 95:5). The eluate containing the target compound was concentrated and then lyophilized, whereby 380 mg (23.7%) of the title compound was obtained. The physical properties of the resulting compound are as follows:

$^1$H-NMR(DMSO-d$_6$-D$_2$O) δ: 1.89–1.93(2H,m), 2.99–3.05(2H,m), 3.11–3.16(4H,m), 3.38–3.41(2H,m), 7.61–7.71(2H,m), 7.88–8.00(2H,m), 8.11(1H,t,J=7.8 Hz), 8.72(1H,d,J=7.4 Hz), 8.83(1H,d,J=8.3 Hz), 9.00(1H,s), 9.52 (1H,s).

Referential Example 17

Synthesis of 1-[N-[2-[(2-aminoethyl)amino]ethyl]carbamoyl]-3-methylcabamoyl-5-(3-nitro-1,8-naphthalimido)benzene hydrochloride To a suspension of 2.03 g (5.0 mmol) of the compound obtained above in Referential Example 16 in N,N-dimethylformamide (10 ml) was added 1.62 g (10.0 mmol) of N,N'-carbonyldiimidazole and the resulting mixture was stirred at 50° C. for 30 minutes. To the resulting solution, was added 2.5 ml (5.0 mmol) of a 2M solution of methylamine in tetrahydrofuran was added under ice cooling, followed by stirring at room temperature for 15 minutes. The reaction mixture was added to a solution of 2.58 g (25.0 mmol) of diethylenetriamine in N,N-dimethylformamide (10 ml) under ice cooling. The resulting mixture was stirred at room temperature for 15 minutes. To the reaction mixture was added 15 ml of 6N hydrochloric acid, followed by purification through reversed phase column chromatography (CHP-20P/mobile phase; water:acetonitrile=90:10). The eluate containing the target compound was concentrated and lyophilized, whereby 850 mg (29.4%) of the title compound was obtained. The physical properties of the resulting compound are as follows:

$^1$H-NMR(DMSO-d$_6$-D$_2$O) δ: 2.80 and 2.82(total 3H, each s), 3.08–3.20(6H,m), 8.01–8.12(3H,m), 8.55–8.90(5H,m), 9.52(1H,d,J=2.2 Hz).

IR(KBr)cm$^{-1}$: 1715, 1672, 1596, 1541, 1420, 1368

In a similar manner, the compounds of Referential Examples 18 to 25 were obtained.

Referential Example 18

1-[N-[2-[(2-Aminoethyl)amino]ethyl]carbamoyl]-3-(3-nitro-1,8-naphthalimido)-5-[N-(2-pyrrolidinoethyl)carbamoyl]benzene hydrochloride The physical properties of the resulting compound are as follows:

$^1$H-NMR(DMSO-d$_6$-D$_2$O) δ: 1.70–2.15(4H,m), 3.00–3.40(10H,m), 3.60–3.75(6H,m), 8.07–8.20(3H,m), 8.60(1H,s), 8.73–8.85(2H,m), 9.03(1H,s), 9.52(1H,s).

IR(KBr)cm$^{-1}$: 1715, 1671, 1598, 1541, 1421, 1342

Referential Example 19

1-[N-[2-[(2-Aminoethyl)amino]ethyl]carbamoyl]-3-(3-nitro-1,8-naphthalimido)-5-[N-(2-piperidinoethyl)carbamoyl]benzene hydrochloride The physical properties of the resulting compound are as follows:

$^1$H-NMR(DMSO-d6-D$_2$O) δ: 1.65–1.90(6H,m), 2.90–3.00(2H,m), 3.15–3.75(14H,m), 8.12(1H,s), 8.70–9.15 (6H,m), 9.56(1H,s).

IR(KBr)cm$^{-1}$: 1715, 1671, 1598, 1541, 1421, 1342

Referential Example 20

1-[N-[2-[(2-Aminoethyl)amino]ethyl]carbamoyl]-3-morpholinocarbonyl-5-(3-nitro-1,8-naphthalimido)benzene hydrochloride The physical properties of the resulting compound are as follows:

$^1$H-NMR(DMSO-d$_6$-D$_2$O) δ: 3.15–3.26(8H,m), 3.56–3.69(8H,m), 7.71(1H,t,J=1.5 Hz), 8.04(1H,t,J=1.5 Hz), 8.06–8.12(2H,m), 8.69(1H,d,J=6.6 Hz), 8.83(1H,t,J= 6.6 Hz), 8.96(1H,d,J=2.2 Hz), 9.53(1H,d,J=2.2 Hz).

IR(KBr)cm$^{-1}$: 1716, 1675, 1633, 1597, 1541, 1424, 1367

Referential Example 21

1-[N-[2-[(2-Aminoethyl)amino]ethyl]carbamoyl]-3-(4-methylpiperazino)carbonyl-5-(3-nitro-1,8-naphthalimido)benzene hydrochloride The physical properties of the resulting compound are as follows:

$^1$H-NMR(DMSO-d$_6$-D$_2$O) δ: 2.68(3H,s), 3.00–3.22(10H, m), 3.53–3.61(2H,m), 7.73(1H,brs), 8.00(1H,brs), 8.08(2H, t,J=7.9 Hz), 8.69(2H,t,J=7.3 Hz), 8.79(2H,t,J=8.1 Hz), 8.97 (1H,d,J=2.2 Hz), 9.48(1H,d,J=2.2 Hz).

Referential Example 22

1-[N-[2-[(2-Aminoethyl)amino]ethyl]carbamoyl]-3-(4-methylpiperazino)carbonyl-5-(1,8-naphthalimido)benzene hydrochloride The physical properties of the resulting compound are as follows:

$^1$H-NMR(DMSO-d$_6$-D$_2$O) δ: 2.49(3H,s), 3.07–3.26(12H, m), 3.55–3.63(4H,m), 7.85(2H,t,J=7.7 Hz), 8.00(2H,brs), 8.43–8.48(4H,m), 8.57(1H,brs).

Referential Example 23

1-[N-[2-[(2-Aminoethyl)amino]ethyl]carbamoyl]-3-(4-ethylpiperazino)carbonyl-5-(3-nitro-1,8-naphthalimido)benzene hydrochloride The physical properties of the resulting compound are as follows:

$^1$H-NMR(DMSO-d$_6$-D$_2$O) δ: 1.25–1.30(3H,m), 3.05–3.25(12H,m), 3.35–3.45(2H,m), 3.60–3.68(2H,m), 4.35–4.42(2H,m), 7.79(1H,s), 8.08–8.20(3H,m), 8.70–9.05 (3H,m), 9.53–9.58(1H,m).

IR(KBr)cm$^{-1}$: 1711, 1670, 1598, 1539, 1422, 1340, 1247

Referential Example 24

1-[N-[2-[(2-Aminoethyl)amino]ethyl]carbamoyl]-3-(3-nitro-1,8-naphthalimido)-5-(4-piperidinopiperidino)carbonylbenzene hydrochloride The physical properties of the resulting compound are as follows:

$^1$H-NMR(DMSO-d$_6$-D$_2$O) δ: 1.60–2.30(10H,m), 2.75–3.80(16H,m), 4.66(1H,brs), 7.74(1H,s), 8.05–8.15(3H, m), 8.70–9.00(3H,m), 9.56(1H,s).

IR(KBr)cm$^{-1}$: 1716, 1675, 1630, 1598, 1540, 1456, 1421, 1341

Referential Example 25

A mixture of 1-[N-[2-[(3-aminopropyl)amino]ethyl] carbamoyl]-3-(4-methylpiperazino)carbonyl-5-(3-nitro-1,8-naphthalimido)benzene hydrochloride and 1-[N-[3-[(2-aminoethyl)amino]propyl]carbamoyl]-3-(4-methylpiperazino)carbonyl-5-(3-nitro-1,8-naphthalimido)benzene hydrochloride The physical properties of the resulting compound are as follows:

$^1$H-NMR(DMSO-d$_6$-D$_2$O) δ: 1.82–1.94(2H,m), 2.77(1H, brs), 2.82–3.62(16H,m), 7.72–7.76(1H,m), 7.99–8.11(3H, m), 8.69(1H,d,J=7.3 Hz), 8.80(1H,d,J=8.3 Hz), 8.97(1H,d, J=2.2 Hz), 9.49(1H,d,J=2.4 Hz).

Example 1

Synthesis of 1,3-bis[N-[2-[[2-(1,8-naphthalimido) ethyl]amino]ethyl]carbamoyl]-5-(1,8-naphthalimido) benzene dimethanesulfonate (Compound No. 1)

To a suspension of 361 mg (1.0 mmol) of 5-(1,8-naphthalimido)isophthalic acid in N,N-dimethylformamide (2 ml) was added 324 mg (2.0 mmol) of N,N'-carbonyldiimidazole. The resulting mixture was stirred at 50° C. for 30 minutes. After cooling to room temperature, the reaction mixture was added to a suspension, which had been obtained by mixing 891 mg (2.5 mmol) of N-[2-[(2-aminoethyl)amino]ethyl]-1,8-naphthalimide dihydrochloride obtained in a similar manner to Referential Example 3 and triethylamine (0.7 ml) in N,N-dimethylformamide (2 ml), at room temperature, followed by stirring at room temperature for 30 minutes. The reaction mixture was purified by chromatography on a silica gel column (mobile phase; chloroform:methanol:aqueous ammonia= 85:14.55:0.45). The eluate was concentrated and the residue was dissolved in N,N-dimethylformamide (2 ml). To the resulting solution was added 288 mg (3.0 mmol) of methanesulfonic acid, followed by mixing. Methanol (about 30 ml) was added and the resulting mixture was stirred. The powder thus obtained was collected by filtration under reduced pressure, whereby 530 mg (48.9%) of the title compound was obtained. The physical properties of the resulting compound are as follows:

$^1$H-NMR(DMSO-d$_6$-D$_2$O) δ: 2.30 (6H,s), 3.15–3.22(4H, m), 3.30–3.38(4H,m), 3.52–3.60(4H,m), 4.34–4.40(4H,m), 7.82(4H,t,J=7.8 Hz), 7.90–7.98(4H,m), 8.38(4H,d,J=7.6 Hz), 8.47(4H,d,J=7.5 Hz), 8.53(2H,d,J=6.3 Hz), 8.57(2H,d, J=8.3 Hz).

IR(KBr)cm$^{-1}$: 1702, 1660, 1626, 1589, 1376, 1351, 1239, 1198

Example 2

Synthesis of 1,3-bis[N-[2-[[2-(3-nitro-1,8-naphthalimido)ethyl]amino]ethyl]carbamoyl]-5(1,8-naphthalimido)benzene dimethanesulfonate (Compound No. 2)

In accordance with the process as described above in Example 1, 324 mg (13.8%) of the title compound was obtained from 723 mg (2.0 mmol) of 5-(1,8-naphthalimido) isophthalic acid and 1782 mg (5.0 mmol) of N-[2-(2-aminoethylamino)ethyl]-3-nitro-1,8-naphthalimide dihydrochloride. The physical properties of the resulting compound are as follows:

$^1$H-NMR(DMSO-d$_6$-D$_2$O) δ: 2.30(6H,s), 3.16–3.22(4H, m), 3.33–3.40(4H,m), 3.53–3.60(4H,m), 4.34–4.42(4H,m), 7.92–8.05(6H,m), 8.39(1H,brs), 8.52(2H,d,J=7.1 Hz), 8.58 (2H,d,J=8.3 Hz), 8.66(2H,d,J=7.3 Hz), 8.71(2H,d,J=8.3 Hz), 8.95(2H,d,J=1.5 Hz), 9.41(2H,d,J=1.9 Hz).

IR(KBr)cm$^1$: 1709, 1667, 1598, 1540, 1436, 1374, 1348, 1241, 1203, 1046

Example 3

Synthesis of 1,3-bis[N-[2-[[2-(pyrido[3,4-b]indol-9-yl)ethyl]amino]ethyl]carbamoyl]-1-(3-nitro-1,8-naphthalimido)benzene tetratrifluoroacetate (Compound No. 3)

To a suspension of 124 mg (0.305 mmol) of 5-(3-nitro-1,8-naphthalimido)isophthalic acid in dimethyl sulfoxide (1 ml) was added 99 mg (0.610 mmol) of N,N'-carbonyldiimidazole. Until the solid was completely dissolved and emission of a gas stopped, the resulting mixture was gradually heated by a heat gun. After completion of the heating, the reaction mixture was cooled to room temperature. The reaction mixture was then added to a solution of 303 mg (0.610 mmol) of the compound obtained in Referential Example 14 in a solution of dimethyl sulfoxide (1 ml)-dichloromethane (2 ml) at room temperature, followed by stirring overnight at room temperature. The reaction mixture was diluted with dichloromethane and then washed with water and saturated saline. The organic layer was dried over sodium sulfate and concentrated under reduced pressure. The residue was purified by chromatography on a silica gel column (mobile phase; chloroform:methanol=98:2), whereby 336 mg (80.8%) of 1,3-bis[N-[2-[[2-(pyrido[3,4-b]indol-9-yl)ethyl](triphenylmethyl)amino]ethyl] carbamoyl]-1-(3-nitro-1,8-naphthalimido)benzene was obtained.

Melting point: 207 to 210° C.

In anisole (0.5 ml) was suspended 300 mg (0.22 mmol) of the resulting triphenylmethyl compound. Trifluoroacetic acid (2 ml) was added to the resulting suspension, followed by stirring at room temperature for 30 minutes. After completion of the reaction, the reaction mixture was concentrated and the residue was dissolved in ethanol (5 ml). The solution was diluted with diisopropyl ether (10 ml). The precipitate thus obtained was collected by filtration, washed with diisopropyl ether and then dried, whereby 229 mg (78.0%) of the title compound was obtained. The physical properties of the resulting compound are as follows:

$^1$H-NMR(DMSO-d$_6$-D$_2$O) δ: 3.19–3.27(4H,m), 4.86–4.94(4H,m), 7.47(2H,t,J=7.6 Hz), 7.90–7.95(2H,m), 8.07(2H,d,J=1.5 Hz), 8.16(1H,t,J=7.8 Hz), 8.46–9.06(12H, m), 9.36(2H,brs), 9.61(1H,d,J=2.2 Hz).

IR(KBr)cm$^{-1}$: 3072, 2812, 2804, 1675, 1643, 1600, 1542, 1507, 1461, 1422, 1342, 1247, 1204, 1133

Example 4

Synthesis of 1,3-bis[N-[2-[[2-(3-nitro-1,8-naphthalimido)ethyl]amino]ethyl]carbamoyl]-5-(3-nitro-1,8-naphthalimido)benzene dihydrochloride (Compound No. 4)

In accordance with the process as described above in Example 1, 642 mg (50.8%) of the title compound, which was in the form not converted into a salt yet, was prepared from 500 mg (1.23 mmol) of 5-(3-nitro-1,8-naphthalimido) isophthalic acid and 891 mg (2.5 mmol) of the compound obtained in Referential Example 3.

The compound thus obtained was dissolved in N,N-dimethylformamide (2 ml). The resulting solution was treated with concentrated hydrochloric acid (0.5 ml), followed by dilution with methanol. The title compound was isolated as a dihydrochloride by filtering the diluted reaction mixture to collect the precipitate. The physical properties of the resulting compound are as follows:

$^1$H-NMR(DMSO-d$_6$-D$_2$O) δ: 2.92–3.00(4H,m), 3.05–3.12(4H,m), 3.43–3.50(4H,m), 4.20–4.30(4H,m), 7.95–7.99(3H,m), 8.10–8.13(1H,m), 8.27(1H,s), 8.36(1H,s), 8.59(2H,d,J=7.3 Hz), 8.65(2H,d,J=8.6 Hz), 8.70(1H,d,J=7.1 Hz), 8.84(1H,d,J=8.3 Hz), 8.89(2H,s), 8.98(1H,s), 9.35(2H, s), 9.54(1H,s).

IR(KBr)cm$^{-1}$: 3431, 1711, 1669, 1599, 1540, 1511, 1455, 1435, 1422, 1369, 1344, 1247

Example 5

Synthesis of 1,3-bis[N-[2-[[2-(pthalimido)ethyl]amino]ethyl]carbamoyl]-5-(3-nitro-1,8-naphthalimido)benzene dihydrochloride (Compound No. 5)

In dimethyl sulfoxide (2 ml), 361 mg (0.5 mmol) of the compound obtained in Referential Example 4 and 219 mg (1.0 mmol) of N-ethoxycarbonyl phthalimide were mixed. To the resulting suspension was added triethylamine (0.5 ml), followed by stirring at room temperature for 30 minutes. The reaction mixture was separated and purified by chromatography on a silica gel column. The fractions eluted from chloroform:methanol=80:20 (v/v) were collected and concentrated. The residue was dissolved in a mixture of 0.2N hydrochloric acid (10 ml) and methanol (20 ml), followed by concentration. To the residue was added 5 ml of water and the mixture was lyophilized, whereby 185 mg (40.7%) of the title compound was obtained. The physical properties of the resulting compound are as follows:

$^1$H-NMR(DMSO-d$_6$-D$_2$O) δ: 2.90–2.97(4H,m), 3.42–3.50(4H,m), 3.72–3.80(4H,m), 7.74–7.82(8H,m), 8.02 (2H,d,J=1.5 Hz), 8.09(1H,t,J=7.6 Hz), 8.69(1H,d,J=7.3 Hz), 8.96(1H,d,J=1.6 Hz), 9.52(1H,d,J=1.8 Hz).

IR(KBr)cm$^{-1}$: 3390, 1715, 1674, 1598, 1542, 1421, 1399, 1369, 1342, 1247

Example 6

Synthesis of 1,3-bis[N-[2-[[2-(1,8-naphthalimido) ethyl]amino]ethyl]carbamoyl]-5-(3-nitro-1,8-naphthalimido)benzene and dihydrochloride thereof (Compound No. 6)

Triethylamine (0.7 ml) was added to a suspension of 361 mg (0.5 mmol) of the compound obtained in Referential Example 4 and 198 mg (1.0 mmol) of 1,8-naphthalic anhydride in N,N-dimethylformamide (4 ml), followed by reaction at 100° C. for 2 hours. After completion of the reaction, the reaction mixture was purified by chromatography on a silica gel column (mobile phase; chloroform:methanol:aqueous ammonia=90:9.7:0.3), whereby 206 mg (44.0%) of the title compound was obtained.

To N,N-dimethylformamide (4 ml) was dissolved 196 mg (0.21 mmol) of the free amine compound thus obtained, followed by the addition of 1N hydrochloric acid (1 ml). After the resulting mixture was made uniform, methanol (40 ml) was added to the resulting uniform solution and the resulting mixture was stirred. The precipitate was collected by filtration under reduced pressure, washed with methanol and then dried, whereby 140 mg (66.3% from the amine compound) of the target dihydrochloride was obtained. The physical properties of the resulting compound are as follows:

$^1$H-NMR(DMSO-d$_6$-D$_2$O) δ: 3.14–3.24(4H,m), 3.31–3.39(4H,m), 3.52–3.61(4H,m), 4.37(4H,t,J=5.5 Hz), 7.81(4H,t,J=7.7 Hz), 8.02(2H,s), 8.12(1H,t,J=7.8 Hz), 8.39 (4H,d,J=8.3 Hz), 8.44(4H,d,J=7.1 Hz), 8.67–8.72(2H,m), 8.86(1H,d,J=8.3 Hz), 8.50–9.30(3H,m), 9.55(1H,d,J=2.2 Hz).

IR(KBr)cm$^{-1}$: 3420, 1700, 1659, 1627, 1591, 1556, 1540, 1440, 1419, 1344, 1241

Example 7

Synthesis of 1,3-bis[N-[2-[[2-(2,3-naphthalimido) ethyl]amino]ethyl]carbamoyl]-5-(3-nitro-1,8-naphthalimido)benzene dihydrochloride (Compound No. 7)

In accordance with the process as described above in Example 6, 120 mg (23.8%) of the title compound was obtained from 361 mg (0.5 mmol) of the compound obtained in Referential Example 4 and 198 mg (1.0 mmol) of 2,3-naphthalic anhydride. The physical properties of the resulting compound are as follows:

$^1$H-NMR(DMSO-d$_6$-D$_2$O) δ: 3.15–3.23(4H,m), 3.28–3.37(4H,m), 3.53–3.62(4H,m), 3.94–4.02(4H,m), 7.70–7.75(4H,m), 8.07(2H,d,J=1.5 Hz), 8.10(1H,t,J=7.8 Hz), 8.47(4H,s), 8.67–8.73(2H,m), 8.85(1H,d,J=7.6 Hz), 8.95(1H,d,J=1.2 Hz), 9.54(1H,d,J=1.2 Hz).

IR(KBr)cm$^{-1}$: 3422, 1767, 1714, 1676, 1600, 1541, 1516, 1446, 1425, 1386, 1343

Example 8

Synthesis of 1,3-bis[N-[2-[[2-(4-chloro-1,8-naphthalimido)ethyl]amino]ethyl]carbamoyl]-5-(3-nitro-1,8-naphthalimido)benzene dihydrochloride (Compound No. 8)

In accordance with the process as described above in Example 6, 500 mg (46.4%) of the title compound was obtained from 723 mg (1.0 mmol) of the compound obtained in Referential Example 4 and 465 mg (2.0 mmol) of 4-chloro-1,8-naphthalic anhydride. The physical properties of the resulting compound are as follows:

$^1$H-NMR(DMSO-d$_6$-D$_2$O) δ: 3.17–3.25(4H,m), 3.36–3.45(4H,m), 3.55–3.61(4H,m), 4.35–4.40(4H,m), 7.93–8.02(6H,m), 8.14(1H,t,J=7.7 Hz), 8.38(2H,d,J=8.1 Hz), 8.53(2H,s), 8.55(2H,s), 8.73(1H,d,J=7.3 Hz), 8.86–9.00(3H,m), 9.56(1H,d,J=2.2 Hz).

Example 9

Synthesis of 1,3-bis[N-[2-[[2-(4-chloro-1,8-naphthalimido)ethyl]amino]ethyl]carbamoyl]-5-(1,8-naphthalimido)benzene dihydrochloride (Compound No. 10)

In accordance with the process as described above in Example 6, 652 mg (63.1%) of the title compound was obtained from 723 mg (1.0 mmol) of 1,3-bis[N-[2-[(2-aminoethyl)amino]ethyl]carbamoyl]-5(1,8-naphthalimido)benzene tetrahydrochloride synthesized in a similar manner to Referential Example 4 and 465 mg (2.0 mmol) of 4-chloro-1,8-naphthalic anhydride. The physical properties of the resulting compound are as follows:

$^1$H-NMR(DMSO-$d_6$-$D_2O$) δ: 3.18–3.23(4H,m), 3.35–3.40(4H,m), 3.55–3.62(4H,m), 4.35–4.38(4H,m), 7.91–8.01(7H,m), 8.40–8.42(2H,m), 8.52–8.61(8H,m), 8.90–8.95(2H,m).

IR(KBr)cm$^{-1}$: 3426, 3067, 1704, 1663, 1589, 1544, 1353, 1240

Example 10

Synthesis of a mixture (Compound No. 11) of 1,3-bis[N-[3-[[2-(3-nitro-1,8-naphthalimido)ethyl]amino]propyl]carbamoyl]-5-(3-nitro-1,8-naphthalimido)benzene, 1,3-bis[N-[2-[[3-(3-nitro-1,8-naphthalimido)propyl]amino]ethyl]carbamoyl]-5-(3-nitro-1,8-naphthalimido)benzene and 1-(3-nitro-1,8-naphthalimido)-3-[N-[3-[[2-(3-nitro-1,8-naphthalimido)ethyl]amino]propyl]carbamoyl]-5-[N-[2-[[3-(3-nitro-1,8-naphthalimido)propyl]amino]ethyl]carbamoyl]benzene dihydrochloride In accordance with the process as described above in Example 6, 316 mg (56.0%) of the title compound was obtained from 375 mg (0.50 mmol) of a mixture of 1,3-bis[N-[3-[(2-aminoethyl)amino]propyl]carbamoyl]-5-(3-nitro-1,8-naphthalimido)benzene, 1,3-bis[N-[2-[(3-aminopropyl)amino]ethyl]carbamoyl]-5-(3-nitro-1,8-naphthalimido)benzene and 1-(3-nitro-1,8-naphthalimido)-3-[N-[3-[(2-aminoethyl)amino]propyl]carbamoyl]-5-[N-[2-[(3-aminopropyl)amino]ethyl]carbamoyl]benzene tetrahydrochloride and 465 mg (2.0 mmol) of 3-nitro-1,8-naphthalic anhydride. The physical properties of the resulting compound are as follows:

$^1$H-NMR(DMSO-$d_6$-$D_2O$) δ: 1.78–2.10(4H,m), 2.98–3.37(12H,m), 4.06–4.38(4H,m), 7.94–8.07(5H,m), 8.46–8.90(11H,m), 9.32–9.47(3H,m).

IR(KBr)cm$^{-1}$: 3423, 1711, 1669, 1598, 1540, 1513, 1423, 1341, 1246

Example 11

Synthesis of 1,3-bis[N-[3-[[3-(3-nitro-1,8-naphthalimido)propyl]amino]propyl]carbamoyl]-5-(3-nitro-1,8-naphthalimido)benzene dihydrochloride (Compound No. 12)

In accordance with the process as described above in Example 6, 70 mg (6.1%) of the title compound was obtained from 779 mg (1.0 mmol) of -1,3-bis[N-[3-[(3-aminopropyl)amino]propyl]carbamoyl]-5-(3-nitro-1,8-naphthalimido)benzene tetrahydrochloride synthesized in a similar manner to Referential Example 4 and 465 mg (2.0 mmol) of 3-nitro-1,8-naphthalic anhydride. The physical properties of the resulting compound are as follows:

$^1$H-NMR(DMSO-$d_6$-$D_2O$) δ: 1.86–1.90(4H,m), 2.01–2.05(4H,m), 2.97–3.07(8H,m), 3.35–3.39(4H,m), 4.11–4.15(4H,m), 8.00–8.10(4H,m), 8.50(1H,s), 8.63–8.67 (3H,m), 8.72(2H,d,J=8.6 Hz), 8.80(1H,d,J=8.3 Hz), 8.90–8.92(4H,m), 9.40(2H,s), 9.49(1H,s).

IR(KBr)cm$^{-1}$: 3418, 1709, 1666, 1598, 1541, 1437, 1422, 1246

Example 12

Synthesis of 1-(4-amino-1,8-naphthalimido)-3,5-bis[N-[2-[[2-(4-amino-1,8-naphthalimido)ethyl]amino]ethyl]carbamoyl]benzene dihydrochloride (Compound No. 13)

In a mixture of N,N-dimethylformamide (5 ml) and tetrahydrofuran (20 ml) was dissolved 83 mg (0.075 mmol) of 1,3-bis[N-[2-[[2-(4-nitro-1,8-naphthalimido)ethyl]amino]ethyl]carbamoyl]-5-(4-nitro-1,8-naphthalimido)benzene dihydrochloride synthesized in accordance with the process as described above in Example 1, followed by catalytic reduction at room temperature for 30 minutes in the presence of palladium carbon (500 mg) as a catalyst under a hydrogen atmosphere of about 4 atmospheric pressure. After completion of the reaction, the catalyst was filtered off and the residue was concentrated under reduced pressure. To the residue was added a mixture of diluted hydrochloric acid and acetone and the mixture was concentrated after stirring. Water was added to the residue, followed by lyophilization, whereby 40 mg (52.8%) of the title compound was obtained. The physical properties of the resulting compound are as follows:

IR(KBr)cm$^{-1}$: 1686, 1647, 1584, 1534, 1366, 1247

Example 13

Synthesis of 1-(3-nitro-1,8-naphthalimido)-3-[N-[2-[[2-(3-nitro-1,8-naphthalimido)ethyl]amino]ethyl]carbamoyl]-5-[N-[2-[[2-(quinoline-3-carbonylamino)ethyl]amino]ethyl]carbamoyl]benzene trihydrochloride (Compound No. 14)

To a solution of 52.0 mg (0.3 mmol) of 3-quinolinecarboxylic acid in N,N-dimethylformamide (1 ml) was added 48.6 mg (0.3 mmol) of N,N'-carbonyldiimidazole. The resulting mixture was stirred at 50° C. for 30 minutes. The reaction mixture was added at room temperature to a suspension, which had been obtained by mixing 273 mg (0.3 mmol) of the compound obtained in Referential Example 12 and triethylamine (0.5 ml) in N,N-dimethylformamide (2 ml) and then distilling off the excess triethylamine under reduced pressure. After stirring at room temperature for 15 minutes, the reaction mixture was purified by chromatography on a silica gel column (mobile phase; chloroform:methanol:aqueous ammonia=80:19.4:0.6). The eluate containing the target compound was concentrated and the residue was dissolved in N,N-dimethylformamide (2 ml). To the resulting solution was added 6N hydrochloric acid (0.5 ml). After concentrating the solution to about half of its initial amount, methanol (20 ml) and then ethyl acetate (20 ml) were added and the precipitate thus formed was collected by filtration, whereby 168 mg (52.5%) of the title compound was obtained. The physical properties of the resulting compound are as follows:

$^1$H-NMR(DMSO-$d_6$-$D_2O$) δ: 3.20–3.27(6H,m), 3.33–3.40(2H,m), 4.36–4.42(2H,m), 7.69(1H,t,J=7.4 Hz), 7.86(1H,t,J=7.7 Hz), 7.96–8.13(6H,m), 8.60–8.70(4H,m), 8.84(1H,d,J=8.3 Hz), 8.90–9.30(4H,m), 9.34(1H,brs), 9.36 (1H,d,J=2.2 Hz), 9.53(1H,d,J=2.2 Hz).

IR(KBr)cm$^{-1}$: 3396, 1713, 1669, 1598, 1540, 1434, 1421, 1369, 1342, 1247

Example 14

Synthesis of 1-(3-nitro-1,8-naphthalimido)-3-[N-[2-[[2-(3-nitro-1,8-naphthalimido)ethyl]amino]ethyl]carbamoyl]-5-[N-[2-[[2-(quinoline-4-carbonylamino)ethyl]amino]ethyl]carbamoyl]benzene trihydrochloride (Compound No. 16)

In accordance with the process as described above in Example 13, 145 mg (45.3%) of the title compound was obtained from 52.0 mg (0.3 mmol) of 4-quinolinecarboxylic acid and 273 mg (0.3 mmol) of the compound obtained in Referential Example 12. The physical properties of the resulting compound are as follows:

¹H-NMR(DMSO-d₆-D₂O) δ: 3.18–3.30(6H,m), 3.30–3.45(2H,m), 3.65–3.75(2H,m), 4.35–4.43(2H,m), 7.68 (1H,t,J=7.6 Hz), 7.80(1H,t,J=4.6 Hz), 7.84(1H,t,J=7.7 Hz), 7.96–8.13(5H,m), 8.22(1H,d,J=8.5 Hz), 8.84(1H,d,J=8.3 Hz), 8.93(1H,d,J=2.2 Hz), 8.95(1H,d,J=2.2 Hz), 9.38(1H,d, J=2.2 Hz), 9.54(1H,d,J=2.2 Hz).

IR(KBr)cm⁻¹: 3423, 1712, 1669, 1599, 1540, 1511, 1434, 1421, 1370, 1343, 1247

Example 15

Synthesis of 1-(3-nitro-1,8-naphthalimido)-3-[N-[2-[[2-(3-nitro-1,8-naphthalimido)ethyl]amino]ethyl] carbamoyl]-5-[N-[2-[[2-(quinoxaline-2-carbonylamino)ethyl]amino]ethyl]carbamoyl] benzene trihydrochloride (Compound No. 17)

In accordance with the process as described above in Example 13, 135 mg (42.2%) of the title compound was obtained from 52.2 mg (0.3 mmol) of 2-quinoxalinecarboxylic acid and 273 mg (0.3 mmol) of the compound obtained in Referential Example 12. The physical properties of the resulting compound are as follows:

¹H-NMR(DMSO-d₆-D₂O) δ: 3.15–3.27(6H,m), 3.33–3.40(2H,m), 3.53–3.63(4H,m), 3.65–3.73(2H,m), 4.35–4.42(2H,m), 7.90–8.18(9H,m), 8.58–8.65(2H,m), 8.68 (1H,d,J=7.6 Hz), 8.85(1H,d,J=8.3 Hz), 8.93(1H,d,J=2.2 Hz), 8.97(1H,d,J=2.2 Hz), 9.38(1H,d,J=2.2 Hz), 9.55(1H,d, J=2.2 Hz).

IR(KBr)cm⁻¹: 3402, 3072, 1713, 1672, 1598, 1540, 1422, 1341, 1247

Example 16

Synthesis of 1-(3-nitro-1,8-naphthalimido)-3-[N-[2-[[2-(3-nitro-1,8-naphthalimido)ethyl]amino]ethyl] carbamoyl]-5-[N-[2-[[2-(1-methylindole-2-carbonylamino)ethyl]amino]ethyl]carbamoyl] benzene dihydrochloride (Compound No. 18)

In accordance with the process as described above in Example 13, 39 mg (12.6%) of the title compound was obtained from 52.6 mg (0.3 mmol) of 1-methylindolecarboxylic acid and 273 mg (0.3 mmol) of the compound obtained in Referential Example 12. The physical properties of the resulting compound are as follows:

¹H-NMR(DMSO-d₆-D₂O) δ: 3.15–3.25(6H,m), 3.33–3.40(2H,m), 3.89(3H,s), 4.35–4.42(2H,m), 7.02(1H,t, J=7.5 Hz), 7.09(1H,brs), 7.20(1H,t,J=7.7 Hz), 7.42(1H,d,J= 8.3 Hz), 7.56(1H,d,J=8.1 Hz), 7.96–8.14(4H,m), 8.61–8.72 (5H,m), 8.85(1H,d,J=8.5 Hz), 8.93(1H,d,J=2.2 Hz), 8.96 (1H,d,J=2.2 Hz), 9.37(1H,d,J=2.2 Hz), 9.54(1H,d,J=2.2 Hz).

IR(KBr)cm⁻¹: 3421, 3075, 1712, 1670, 1598, 1541, 1460, 1422, 1342, 1247

Example 17

Synthesis of 1-[N-[2-[[2-(2,3-naphthalimido)ethyl] amino]ethyl]carbamoyl]-3-(3-nitro-1,8-naphthalimido)-5-[N-[2-[[2-(3-nitro-1,8-naphthalimido)ethyl]amino]ethyl]carbamoyl] benzene dihydrochloride (Compound No. 19)

To a suspension of 273 mg (0.3 mmol) obtained in Referential Example 12 in N,N-dimethylformamide (3 ml) were added triethylamine (0.5 ml) and then 59.5 mg (0.3 mmol) of 2,3-naphthalenedicarboxylic anhydride. The resulting mixture was reacted at 100° C. for 1 hour. After completion of the reaction, the reaction mixture was cooled to room temperature and purified by chromatography on a silica gel column (mobile phase; chloroform:methanol:aqueous ammonia=90:9.7:0.3). The eluate containing the target compound was concentrated and the residue was dissolved in N,N-dimethylformamide (2 ml). The resulting solution was added to 6N hydrochloric acid (0.5 ml). After the solution was concentrated to half of its original amount, methanol (20 ml) and then diisopropyl ether (20 ml) were added. The precipitate thus formed was collected by filtration, whereby 129 mg (40.8%) of the title compound was obtained. The physical properties of the resulting compound are as follows:

¹H-NMR(DMSO-d₆-D₂O) δ: 3.12(4H,m), 3.25–3.38(4H, m), 3.50–3.60(4H,m), 3.92–3.98(2H,m), 4.34–4.40(2H,m), 7.67–7.72(2H,m), 7.91–8.02(3H,m), 8.10(1H,t,J=7.8 Hz), 8.14–8.20(2H,m), 8.42(2H,s), 8.50–8.53(1H,m), 8.62(2H,t, J=8.1 Hz), 8.68(1H,d,J=7.3 Hz), 8.83(1HI,d,J=8.5 Hz), 8.91 (1H,d,J=2.2 Hz), 8.95(1H,d,J=2.2 Hz), 9.31(1H,d,J=2.2 Hz), 9.51(1H,d,J=2.2 Hz).

IR(KBr)cm⁻¹: 3426, 3074, 1766, 1712, 1671, 1598, 1540, 1516, 1425, 1342, 1247

Example 18

Synthesis of 1,3-bis[N-[2-[[2-(quinoline-3-carbonylamino)ethyl]amino]ethyl]carbamoyl]-5-(3-nitro-1,8-naphthalimido)benzene tetrahydrochloride (Compound No. 21)

To a solution of 173 mg (1.0 mmol) of 3-quinolinecarboxylic acid in dimethyl sulfide (1 ml), 162 mg (1.0 mmol) of N,N'-carbonyldiimidazole was added and the resulting mixture was stirred at 60° C. for 30 minutes. On the side, to a suspension of 361 mg (0.5 mmol) of the compound obtained in Referential Example 4 in N,N-dimethylformamide (2 ml) was added triethylamine (0.5 ml), followed by stirring at room temperature for 5 minutes. Two reaction mixtures thus obtained were mixed and the resulting suspension was stirred at room temperature for 1 hour. To the reaction mixture was added a 1N hydrochloric acid solution (5 ml). The mixture was purified by reversed phase column chromatography (CHP-20P/mobile phase; water:acetonitrile=90:10). The eluate containing the target compound was concentrated to about 20 ml, followed by lyophilization, whereby 208 mg (43.3%) of the title compound was obtained. The physical properties of the resulting compound are as follows:

¹H-NMR(DMSO-d₆-D₂O) δ: 3.20–3.30(8H,m), 3.64–3.73(8H,m), 7.65(2H,t,J=7.6 Hz), 7.81(2H,t,J=7.6 Hz), 7.99–8.13(7H,m), 8.68(1H,d,J=7.3 Hz), 8.83–8.88(2H, m), 8.90(2H,d,J=2.0 Hz), 8.95(1H,d,J=2.2 Hz), 9.16–9.21 (2H,m), 9.33(2H,d,J=2.2 Hz), 9.55(1H,d,J=2.4 Hz).

IR(KBr)cm⁻¹: 3423, 1716, 1654, 1599, 1542, 1421, 1342, 1306, 1249

Example 19

Synthesis of 1,3-bis[N-[2-[[2-(quinoline-4-carbonylamino) ethyl]amino]ethyl]carbamoyl]-5-(3-nitro-1,8-naphthalimido)benzene tetrahydrochloride (Compound No. 22)

In accordance with the process as described above in Example 18, 226 mg (47.1%) of the title compound was obtained from 173 mg (1.0 mmol) of 4-quinolinecarboxylic acid and 361 mg (0.5 mmol) of the compound obtained in Referential Example 4. The physical properties of the resulting compound are as follows:

$^1$H-NMR(DMSO-d$_6$-D$_2$O) δ: 3.20–3.32 (8H,m), 3.63–3.75(8H,m), 7.63(2H,t,J=7.6 Hz), 7.71(2H,d,J=4.4 Hz), 7.78(2H,t,J=7.1 Hz), 8.03(2H,d,J=8.5 Hz), 8.08–8.14 (3H,m), 8.22(2H,d,J=8.3 Hz), 8.69(1H,d,J=7.3 Hz), 8.82–8.87(2H,m), 8.93–8.97(3H,m), 9.03–9.15(4H,m), 9.55 (1H,d, J=2.2 Hz).

IR(KBr)cm$^{-1}$: 3427, 1716, 1671, 1653, 1597, 1557, 1541, 1508, 1458, 1421, 1341

Example 20

Synthesis of 1,3-bis[N-[2-[[2-(4-nitro-1-methylpyrrole-2-carbonylamino)ethyl]amino]ethyl] carbamoyl]-5-(3-nitro-1,8-naphthalimido)benzene dihydrochloride (Compound No. 24)

To a solution of 361 mg (0.5 mmol) obtained in Referential Example 4 in N,N-dimethylformamide (3 ml) was added triethylamine (0.7 ml) and the mixture was stirred at room temperature for 2 minutes. The resulting suspension was added with 271 mg (1.0 mmol) of 4-nitro-1-methyl-2-(trichloromethyl)pyrrole, followed by stirring at room temperature for 30 minutes. The reaction mixture was then concentrated under reduced pressure. To the residue was added a 1N hydrochloric acid solution (4 ml) to dissolve the former in the latter and the resulting solution was purified by reversed phase column chromatography (CHP-20P/mobile phase; water:acetonitrile=90:10). The eluate containing the target compound was concentrated to about 20 ml, followed by lyophilization, whereby 212 mg (44.5%) was obtained. The physical properties of the resulting compound are as follows:

$^1$H-NMR(DMSO-d$_6$-D$_2$O) δ: 3.13–3.27(8H,m), 3.87(6H, m), 7.46(2H,d,J=2.2 Hz), 8.05–8.16(5H,m), 8.72(1H,d,J=7.3 Hz), 8.86(1H,d,J=7.6 Hz), 9.00(1H,d,J=2.2 Hz), 9.56 (1H,d,J=2.2 Hz).

IR(KBr)cm$^{-1}$: 3413, 1664, 1545, 1529, 1507, 1421, 1341, 1313

Example 21

Synthesis of 1,3-bis[N-[N-[2-[N-(3-dimethylaminopropyl)carbamoyl]-1-methylpyrrol-4-yl]carbamoylmethyl]carbamoyl]-5-(1,8-naphthalimide)benzene dihydrochloride (Compound No. 25)

To a solution of 411 mg (1.0 mmol) of t he compound obtained in Referential Example 6 in dimethyl sulfoxide (2 ml) was added methylhydrazine (0.7 ml) and the mixture was reacted at 90° C. for 2 hours. After completion of the reaction, the reaction mixture was distilled to remove excess methylhydrazine under reduced pressure. To the residue was added a solution of 231 mg (0.5 mmol) of the compound obtained in Referential Example 2 in dimethyl sulfoxide (1 ml), followed by reaction at 50° C. for 2 hours. To the reaction mixture were added ethyl acetate and 1N hydrochloric acid (5 ml) and the resulting mixture was vigorously stirred. After the water layer was separated, it was washed with ethyl acetate and purified by reversed phase column chromatography (CHP-20P/mobile phase; water:acetonitrile=90:10). The eluate containing the target compound was concentrated to about 20 ml, followed by lyophilization, whereby 295 mg (61.4%) was obtained. The physical properties of the resulting compound are as follows:

$^1$H-NMR(DMSO-d$_6$-D$_2$O) δ: 1.78–1.88(4H,m), 2.70 (12H,s), 2.96–3.03(2H,m), 3.22(2H,q,J=6.0 Hz), 3.79(6H, s), 4.04(4H,d,J=6.0 Hz), 6.77(2H,d,J=1.7 Hz), 7.14(2H,d,J= 1.7 Hz), 7.85–7.98(4H,m), 8.11(2H,d,J=1.5 Hz), 8.14–8.25 (2H,m), 8.53–8.62(5H,m), 9.01–9.06(2H,m), 10.01(1H,s).

Example 22

Synthesis of 1,3-bis[N-[N-[2-[N-(3-dimethylaminopropyl)carbamoyl]-1-methylpyrrol-4-yl]carbamoylmethyl]carbamoyl]-5-(3-nitro-1,8-naphthalimido)benzene dihydrochloride (Compound No. 26)

In accordance with the process as described above in Example 21, 275 mg (54.7%) of the title compound was obtained from 411 mg (1.0 mmol) of the compound obtained in Referential Example 6 and 231 mg (0.5 mmol) of 5-(3-nitro-1,8-naphthalimido)isophthaloyl diimidazole synthesized in a similar manner to Referential Example 2. The physical properties of the resulting compound are as follows:

$^1$H-NMR(DMSO-d$_6$-D$_2$O) δ: 1.78–1.88(4H,m), 2.71 (12H,m), 2.97–3.04(4H,m), 3.18–3.25(4H,m), 3.78(6H,s), 4.04(4H,d,J=5.4 Hz), 6.76(2H,d,J=1.7 Hz), 7.12(2H,d,J=1.7 Hz), 8.09–8.19(5H,m), 8.61(1H,s), 8.71(1H,d,J=7.3 Hz), 8.86(1H,d,J=8.3 Hz), 8.98(1H,d,J=2.2 Hz), 9.00–9.60(2H, m), 9.57(1H,d,J=2.2 Hz), 10.00(2H,s).

IR(KBr)cm$^{-1}$: 3436, 1713, 1669, 1650, 1597, 1534, 1469, 1438, 1411, 1343, 1283

Example 23

Synthesis of 1,3-bis[N-[N-[2-[N-(3-dimethylaminopropyl)carbamoyl]-1-methylpyrrol-4-yl]carbamoylmethyl]carbamoyl]-5-(4-nitro-1,8-naphthalimido)benzene dihydrochloride (Compound No. 27)

In accordance with the process as described above in Example 21, 280 mg (55.7%) of the title compound was obtained from 411 mg (1.0 mmol) of the compound obtained in Referential Example 6 and 231 mg (0.5 mmol) of 5-(4-nitro-1,8-naphthalimido)isophthaloyl diimidazole synthesized in a similar manner to Referential Example 6. The physical properties of the resulting compound are as follows:

$^1$H-NMR(DMSO-d$_6$-D$_2$O) δ: 1.77–1.87(4H,m), 2.70 (12H,m), 2.96–3.03(4H,m), 3.18–3.25(4H,m), 3.78(6H,s), 4.04(4H,d,J=5.9 Hz), 6.75(2H,d,J=1.7 Hz), 7.12(2H,d,J=1.7 Hz), 8.10–8.22(5H,m), 8.59–8.69(4H,m), 9.01–9.05(2H,m), 10.00(2H,s).

IR(KBr)cm$^{-1}$: 3421, 1715, 1669, 1649, 1589, 1531, 1467, 1439, 1406, 1369, 1350

Example 24

Synthesis of 1,3-bis[N-[2-[N-[2-[N-(3-dimethylaminopropyl)carbamoyl]-1-methylpyrrol-4-yl]carbamoyl]ethyl]carbamoyl]-5-(3-nitro-1,8-naphthalimido)benzene dihydrochloride (Compound No. 28)

In accordance with the process as described above in Example 21, 489 mg (47.3%) of the title compound was obtained from 422 mg (1.0 mmol) of the compound obtained in Referential Example 7 and 231 mg (0.5 mmol) of 5-(3-nitro-1,8-naphthalimido)isophthaloyl diimidazole synthesized in a similar manner to Referential Example 7. The physical properties of the resulting compound are as follows:

$^1$H-NMR(DMSO-d$_6$-D$_2$O) δ: 1.75–1.84(4H,m), 2.68 (12H,m), 2.95–3.02(4H,m), 3.14–3.21(4H,m), 3.48–3.57 (4H,m), 3.72(6H,s), 6.67(2H,s), 7.08(2H,s), 7.98–8.16(6H, m), 8.47(1H,brs), 8.66(1H,d,J=7.3 Hz), 8.75–8.85(3H,m), 8.92(1H,brs), 9.52(1H,brs), 9.91(2H,brs)

IR(KBr)cm$^{-1}$: 3422, 1713, 1668, 1648, 1597, 1538, 1466, 1440, 1419, 1407, 1366

Example 25

Synthesis of 1,3-bis[N-[3-[N-[2-[N-[2-[N-(3-dimethylaminopropyl)carbamoyl]-1-methylpyrrol-4-yl]carbamoyl]-1-methylpyrrol-4-yl]carbamoyl] propyl]carbamoyl]-5-(3-nitro-1,8-naphthalimido) benzene dihydrochloride (Compound No. 30)

In methanol (20 ml) was dissolved 622 mg (1.1 mmol) of the compound obtained in Referential Example 5, followed by catalytic reduction at room temperature for 2 hours in the presence of palladium carbon as a catalyst under a hydrogen atmosphere of about 3 atmospheric pressure. After completion of the reaction, the catalyst was filtered off and the residue was concentrated under reduced pressure. The residue was dissolved in N,N-dimethylformamide (2 ml). To the resulting solution was added dropwise a solution of unpurified 5-(3-nitro-1,8-naphthalimido)isophthaloyl diimidazole (0.5 mmol), which had been obtained in a similar manner to Referential Example 2, in N,N-dimethylformamide (2 ml) at room temperature. The reaction mixture was stirred at room temperature overnight. After concentration of the reaction mixture, 1N hydrochloric acid (5 ml) and then water (20 ml) were added to the residue and the mixture was purified by reversed phase column chromatography (CHP-20P/mobile phase; water:acetonitrile=85:15). The eluate containing the target compound was concentrated, followed by lyophilization, whereby 180 mg (12.5%) of the title compound was obtained. The physical properties of the resulting compound are as follows:

$^1$H-NMR(DMSO-d$_6$-D$_2$O) δ: 1.78–1.90(8H,m), 2.27–2.35(4H,m), 2.75(12H,s), 3.00–3.07(4H,m), 3.18–3.25 (4H,m), 3.29–3.37(4H,m), 3.77(12H,s), 6.83(2H,d,J=2.0 Hz), 6.87(2H,d,J=2.0 Hz), 7.12(4H,d,J=1.5 Hz), 8.02(2H,d, J=1.5 Hz), 8.06–8.17(2H,m), 8.48(1H,brs), 8.69(1H,d,J=7.8 Hz), 8.75–8.84(3H,m), 8.96(1H,d,J=2.2 Hz), 9.51(1H,d,J= 2.2 Hz), 9.83(2H,brs), 9.88(2H,brs).

IR(KBr)cm$^{-1}$: 3425, 1668, 1653, 1647, 1638, 1591, 1558, 1541

Example 26

Synthesis of 1,3-bis[N-[3-[N-[2-[N-(3-dimethylaminopropyl)carbamoyl]-1-methylpyrrol-4-yl]carbamoyl]propyl]carbamoyl]-5-(3-nitro-1,8-naphthalimido)benzene dihydrochloride (Compound No. 31)

In accordance with the process as described above in Example 25, 335 mg (28.7%) of the title compound was obtained from 488 mg (1.1 mmol) of the compound obtained in Referential Example 8 and 5-(3-nitro-1,8-naphthalimido) isophthaloyl diimidazole (0.5 mmol). The physical properties of the resulting compound are as follows:

$^1$H-NMR(DMSO-d$_6$-D$_2$O) δ: 1.75–1.88(8H,m), 2.25–2.34(4H,m), 2.73(12H,s), 2.97–3.04(4H,m), 3.16–3.23 (4H,m), 3.27–3.36(4H,m), 3.73(6H,s) 6.69(2H,d,J=1.5 Hz), 7.01(2H,d,J=1.5 Hz), 8.01(2H,brs), 8.03–8.08(3H,m), 8.48 (1H,brs), 8.67–8.85(4H,), 8.97(1H,d,J=2.2 Hz), 9.52(1H,d, J=2.2 Hz), 9.86(2H,brs).

IR(KBr)cm$^{-1}$: 1668, 1652, 1647, 1598, 1540, 1341

Example 27

Synthesis of 1,3-bis[N-[N-[2-[N-[2-[N-(3-dimethylaminopropyl)carbamoyl]-1-methylpyrrol-4-yl]carbamoyl]-1-methylpyrrol-4-yl] carbamoylmethyl]carbamoyl]-5-(3-nitro-1,8-naphthalimido)benzene dihydrochloride (Compound No. 32)

In accordance with the process as described above in Example 25, 260 mg (18.9%) of the title compound was obtained from 591 mg (1.1 mmol) of the compound obtained in Referential Example 9 and 5-(3-nitro-1,8-naphthalimido) isophthaloyl diimidazole (0.5 mmol). The physical properties of the resulting compound are as follows:

$^1$H-NMR(DMSO-d$_6$-D$_2$O) δ: 1.72–1.85(4H,m), 2.71 (12H,s), 2.95–3.04(4H,m), 3.13–3.22(4H,m), 3.73(6H,s), 3.76(6H, s), 3.96–4.05(4H,brs), 6.83–6.87(4H,m), 7.08–7.14(4H,m), 8.03–8.10(3H,m), 8.54(1H,brs), 8.67(1H, d,J=7.3 Hz), 8.79(1H,d,J=8.5 Hz), 8.94(1H,d,J=2.2 Hz), 9.49(1H,d,J=2.2 Hz).

IR (KBr)cm$^{-1}$: 3412, 1669, 1647, 1590, 1540, 1467, 1437, 1406, 1343

Example 28

Synthesis of 1,3-bis[N-[2-[N-[2-[N-[2-[N-(3-dimethylaminopropyl)carbamoyl]-1-methylpyrrol-4-yl]carbamoyl]-1-methylpyrrol-4-yl]carbamoyl]ethyl] carbamoyl]-5-(3-nitro-1,8-naphthalimido)benzene dihydrochloride (Compound No. 33)

In accordance with the process as described above in Example 25, 81 mg (5.8%) of the title compound was obtained from 607 mg (1.1 mmol) of the compound obtained in Referential Example 10 and 5-(3-nitro-1,8-naphthalimido)isophthaloyl diimidazole (0.5 mmol). The physical properties of the resulting compound are as follows:

1.79–1.89(4H,m), 2.55–2.64(4H,m), 3.02–3.10(4H,m), 3.20–3.30(4H,m), 3.80(12H,s), 6.86(2H,d,J=1.7 Hz), 6.90 (2H,d,J=2.0 Hz), 7.16(2H,d,J=1.7 Hz), 7.17(2H,d,J=1.7 Hz), 8.03(2H,d,J=1.5 Hz), 8.08–8.19(2H,m), 8.45(1H,brs), 8.71 (1H,d,J=6.3 Hz), 8.75–8.88(3H,m), 8.98(1H,d,J=2.4 Hz), 9.53(1H,d,J=2.2 Hz).

IR(KBr)cm$^{-1}$: 1670, 1662, 1654, 1648, 1637, 1541, 1535

Example 29

Synthesis of 1,3-bis[N-[4-[N-[2-[N-[2-[N-(3-dimethylaminopropyl)carbamoyl]-1-methylpyrrol-4-yl]carbamoyl]-1-methylpyrrol-4-yl]carbamoyl]butyl] carbamoyl]-5-(3-nitro-1,8-naphthalimido)benzene dihydrochloride (Compound No. 34)

In accordance with the process as described above in Example 25, 53 mg (5.9%) of the title compound was obtained from 389 mg (0.67 mmol) of the compound obtained in Referential Example 11 and 5-(3-nitro-1,8-naphthalimido)isophthaloyl diimidazole (0.5 mmol) . The physical properties of the resulting compound are as follows:

¹H-NMR(DMSO-d6-D₂O) δ: 1.50–1.65(8H,m), 1.78–1.97(4H,m), 2.21–2.30(4H,m), 2.75(12H,s), 3.00–3.08 (4H,m), 3.18–3.35(8H,m), 3.77(12H,s), 6.83(2H,d,J=1.7 Hz), 6.88(2H,d,J=1.7 Hz), 7.12(2H,d,J=1.7 Hz), 7.13(2H,d, J=1.7 Hz), 8.00(2H,d,J=1.5 Hz), 8.08(1H,m), 8.43(1H,brs), 8.68(1H,d,J=6.3 Hz), 8.81(1H,d,J=7.8 Hz), 8.96(1H,d,J=2.2 Hz), 9.51(1H,d,J=2.2 Hz).

IR(KBr)cm⁻¹: 3413, 1645, 1591, 1540, 1436

Example 30

Synthesis of 1,3-bis[N-[2-[[2-[4-(4-formamido-1-methylpyrrole-2- carbonylamino)-1-methylpyrrole-2-carbonylamino]ethyl]amino]ethyl]carbamoyl]-5-(3-nitro-1,8-naphthalimido)benzene dihydrochloride (Compound No. 35)

To a solution of 290 mg (1 mmol) of 4-(4-formamido-1-methylpyrrole-2- carbonylamino)-1-methylpyrrole-2-carboxylic acid synthesized in accordance with the process as described in "J. Pharm. Sci. 78, 910–917 (1988)" in N,N-dimethylformamide (4 ml) were added 149 mg (1.1 mmol) of 1-hydroxybenzotriazole hydroxybenzotriazole and 227 mg (1.1 mmol) of N,N'-dicyclohexylcarbodiimide, followed by reaction at 50° C. for 2 hours (reaction mixture 1). On the side, to a solution of 322 mg (0.46 mmol) of the compound obtained in Referential Example 4 in N,N-dimethylformamide (2 ml) was added triethylamine (0.7 ml) and the mixture was stirred at room temperature for short time. To the resulting suspension was added the above-described reaction mixture 1, followed by stirring at room temperature for 1 hour. Ethyl acetate and 1N hydrochloric acid (5 ml) were added to the reaction mixture. The resulting mixture was stirred vigorously. The water layer was then separated and purified by reversed phase column chromatography (CHP-20P/mobile phase; water:acetonitrile= 90:10). The eluate containing the target compound was concentrated to about 20 ml, followed by lyophilization, whereby 78 mg (6.5%) of the title compound was obtained. The physical properties of the resulting compound are as follows:

¹H-NMR(DMSO-d₆-D₂O) δ: 3.07–3.15(4H,m), 3.15–3.23(4H,m), 3.43–3.50(4H,m), 3.71(6H,s), 3.76(6H,s), 6.82(2H,d,J=2.0 Hz), 6.91(2H,d,J=1.7 Hz), 7.08(2H,d,J=1.7 Hz), 7.13(2H,d,J=2.0 Hz), 8.03–8.10(5H,m), 8.59(1H,brs), 8.68(1H,d,J=7.1 Hz), 8.79(1H,d,J=8.5 Hz), 8.94(1H,d,J=2.2 Hz), 9.47(1H,d,J=2.2 Hz).

IR(KBr)cm⁻¹: 1659, 1590, 1540, 1436, 1405, 1341

Example 31

Synthesis of 1,3-bis[N-[2-[[2-[4-[4-(4-formamido-1-methylpyrrole-2-carbonylamino)-1-methylpyrrole-2-carbonylamino]-1-methylpyrrole-2-carbonylamino] ethyl]amino]ethyl]carbamoyl]-5-(3-nitro-1,8-naphthalimido)benzene dihydrochloride (Compound No. 36)

In accordance with the process as described above in Example 30, 48 mg (6.7%) of the title compound was obtained from 206 mg (0.50 mmol) of 4-[4-(4-formamido-1-methylpyrrole-2-carbonylamino)-1-methylpyrrole-2-carbonylamino]-1-methylpyrrole-2-carboxylic acid obtained in accordance with the process as described above in Referential Example 4 and 161 mg (0.23 mmol) of the compound obtained in Referential Example 4. The physical properties of the resulting compound are as follows:

¹H-NMR(DMSO-d₆-D₂O) δ: 3.05–3.27(8H,m), 3.73(6H, s), 3.79(6H,s), 3.81(6H,s), 6.89(2H,d,J=1.9 Hz), 6.93(2H,d, J=1.7 Hz), 6.99(2H,d,J=1.9 Hz), 7.12(2H,d,J=1.7 Hz), 7.16 (2H,d,J=1.7 Hz), 7.17(2H,d,J=1.7 Hz), 8.59(1H,brs), 8.68 (1H,d,J=6.3 Hz), 8.81(1H,d,J=7.7 Hz), 8.95(1H,d,J=2.2 Hz), 9.50(1H,d,J=2.2 Hz).

IR(KBr)cm⁻¹: 3410, 1653, 1589, 1540, 1436, 1405

Example 32

Synthesis of 1-[N-[3-[N-[2-[N-[2-[N-(3-dimethylaminopropyl)carbamoyl]-1-methylpyrrol-4-yl]carbamoyl]-1-methylpyrrol-4-yl]carbamoyl] propyl]carbamoyl]-3-(3-nitro-1,8-naphthalimido)-5-[N-[2-[[2-(3-nitro-1,8-naphthalimido)ethyl]amino] ethyl]carbamoyl]benzene dihydrochloride (Compound No. 37)

To a suspension of 1014 mg (1.0 mmol) of the compound obtained in Referential Example 13 in N,N-dimethylformamide (3 ml) were added triethylamine (1.4 ml) and 243 mg (1.0 mmol) of 3-nitro-1,8-naphthalic anhydride. The resulting mixture was stirred at 80° C. for 30 minutes. After cooling, the reaction mixture was added with 1N hydrochloric acid (6 ml) and then water (10 ml). The resulting suspension was purified by reversed phase column chromatography (CHP-20P/mobile phase; water:acetonitrile=85:15). The eluate containing the target compound was concentrated to about 30 ml, followed by lyophilization, whereby 220 mg (18.3%) of the title compound was obtained. The physical properties of the resulting compound are as follows:

¹H-NMR(DMSO-d₆-D₂O) δ: 1.80–1.88(4H,s), 2.28–2.35 (4H,s), 2.76(6H,s), 3.00–3.10(2H,m), 3.24–3.38(4H,m), 3.60–3.64(2H,m), 3.78–3.82(8H,m), 4.38–4.42(2H,m), 6.85–6.90(2H,m), 7.13(2H,s), 8.00–8.14(3H,m), 8.61–8.98 (6H,m), 9.45(1H,s), 9.58(1H,s), 9.85(1H,d,J=8.8 Hz).

IR(KBr)cm⁻¹: 3429, 1712, 1668, 1600, 1540, 1436, 1421, 1369, 1343, 1248

Example 33

Synthesis of 1-[N-[2-[N-[2-[N-(3-dimethylaminopropyl)carbamoyl]-1-methylpyrrol-4-yl]carbamoyl]ethyl]carbamoyl]-3-(3-nitro-1,8-naphthalimido)-5-[N-[2-[[2-(3-nitro-1,8-naphthalimido)ethyl]amino]ethyl]carbamoyl] benzene dihydrochloride (Compound No. 38)

In accordance with the process as described above in Example 32, 355 mg (66.5%) of the title compound was obtained from 439 mg (0.50 mmol) of 1-[N-[2-[(2-aminoethyl)amino]ethyl]carbamoyl]-3-[N-[2-[N-[2-[N-(3-dimethylaminopropyl)carbamoyl]-1-methylpyrrol-4-yl] carbamoyl]ethyl]carbamoyl]-5-(3-nitro-1,8-naphthalimido) benzene trihydrochloride obtained in a similar manner to Referential Example 13 and 122 mg (0.5 mmol) of 3-nitro-1,8-naphthalic anhydride. The physical properties of the resulting compound are as follows:

¹H-NMR (DMSO-d₆-D₂O) δ: 1.77–1.88(2H,m), 2.74(6H, s), 3.00–3.06(2H,m), 3.15–3.25(4H,m), 3.35–3.41(2H,m), 3.55–3.67(2H,m), 3.74(3H,s), 4.36–4.42(2H,m), 6.68(1H,d, J=1.7 Hz), 7.08(1H,d,J=1.7 Hz), 7.93–8.18(5H,m), 8.50–9.00(8H,m), 9.39(1H,d,J=1.4 Hz), 9.55(1H,d,J=1.8 Hz), 9.90(1H,brs).

IR(KBr)cm⁻¹: 3405, 1714, 1669, 1599, 1540, 1513, 1420, 1341, 1246

Example 34

Synthesis of 1-[N-[3-[N-[2-[N-(3-dimethylaminopropyl)carbamoyl]-1-methylpyrrol-4-yl]carbamoyl]propyl]carbamoyl]-3-(3-nitro-1,8-naphthalimido)-5-[N-[2-[[2-(3-nitro-1,8-naphthalimido)ethyl]amino]ethyl]carbamoyl] benzene dihydrochloride (Compound No. 39)

In accordance with the process as described above in Example 32, 140 mg (40.5%) of the title compound was obtained from 285 mg (0.32 mmol) of 1-[N-[2-[(2-aminoethyl)amino]ethyl]carbamoyl]-3-[N-[3-[N-[2-[N-(3-dimethylaminopropyl)carbamoyl]-1-methylpyrrol-4-yl]carbamoyl]propyl]carbamoyl]-5-(3-nitro-1,8-naphthalimido)benzene trihydrochloride synthesized in a similar manner to Referential Example 13 and 77.8 mg (0.32 mmol) of 3-nitro-1,8-naphthalic anhydride. The physical properties of the resulting compound are as follows:

$^1$H-NMR(DMSO-d$_6$-D$_2$O) δ: 1.80–1.88(2H,m), 2.25–2.35(2H,s), 2.76(6H,s), 3.00–3.40(10H,m), 3.75(3H, s), 4.38–4.42(2H,m), 6.70(1H,s), 7.08(1H,s), 7.91(1H,s), 8.02–8.16(3H,m), 8.43(1H,s), 8.66–8.73(2H,m), 8.87(1H,d, J=7.8 Hz), 8.98(2H,dd,J=2.2,7.3 Hz), 9.38(1H,s), 9.57(1H, s), 9.84(1H,s).

IR(KBr)cm$^{-1}$: 3421, 1713, 1669, 1600, 1540, 1438, 1421, 1369, 1342, 1247

Example 35

Synthesis of 1-[N-[3-[N-[2-[N-[2-[N-(3-dimethylaminopropyl)carbamoyl]-1-methylpyrrol-4-yl]carbamoyl]-1-methylpyrrol-4-yl]carbamoyl] propyl]carbamoyl]-3-[N-[2-[[2-(1,8-naphthalimido) ethyl]amino]ethyl]carbamoyl]-5-(3-nitro-1,8-naphthalimido)benzene dihydrochloride (Compound No. 40)

In accordance with the process as described above in Example 32, 224 mg (48.4%) of the title compound was obtained from 388 mg (0.40 mmol) of the compound obtained in Referential Example 13 and 79 mg (0.4 mmol) of 1,8-naphthalic anhydride. The physical properties of the resulting compound are as follows:

$^1$H-NMR(DMSO-d-D$_2$O) δ: 1.80–1.90(4H,m), 2.28–2.36 (2H,m), 2.77(6H,s), 3.03–3.10(2H,m), 3.19–3.41(8H,m), 4.37–4.43(2H,m), 6.86(1H,d,J=1.5 Hz), 6.90(1H,d,J=1.7 Hz), 7.14(2H,d,J=1.5 Hz), 7.84(2H,t,J=7.8 Hz), 7.98(1H, brs), 8.07(1H,brs), 8.13(1H,t,J=7.8 Hz), 8.40(2H,d,J=7.6 Hz), 8.48(2H,d,J=7.3 Hz), 8.53(1H,brs), 8.78(1H,d,J=7.3 Hz), 8.86(1H,d,J=8.5 Hz), 9.00(1H,d,J=2.2 Hz), 9.55(1H,d, J=2.2 Hz).

IR(KBr)cm$^{-1}$: 3430, 1713, 1700, 1657, 1591, 1540, 1438, 1343

Example 36

Synthesis of 1-[N-[3-[N-[2-[N-[2-[N-methylcarbamoyl)-1-methylpyrrol-4-yl]carbamoyl]-1-methylpyrrol-4-yl]carbamoyl]propyl]carbamoyl]-3-(3-nitro-1,8-naphthalimido)-5-[N-[2-[[2-(3-nitro-1,8-naphthalimido)ethyl]amino]ethyl]carbamoyl] benzene hydrochloride (Compound No. 41)

To a suspension of 272 mg (0.30 mmol) of 1-[N-[2-[(2-aminoethyl)amino]ethyl]carbamoyl]-3-[N-[3-[N-[2-(N-methylcarbamoyl)-1-methylpyrrol-4-yl]carbamoyl]propyl] carbamoyl]-5-(3-nitro-1,8-naphthalimido)benzene dihydrochloride, which had been synthesized in a similar manner to Referential Example 13, in N,N-dimethylformamide (3 ml) were added triethylamine (0.6 ml) and 73 mg (0.30 mmol) of 3-nitro-1,8-naphthalic anhydride, followed by stirring at 80° C. for 30 minutes. After cooling, the reaction mixture was purified by chromatography on a silica gel column (mobile phase; chloroform:methanol=80:20). The eluate containing the target compound was concentrated and the residue was dissolved in N,N-dimethylformamide (2 ml). To the resulting solution was added 6N hydrochloric acid (0.5 ml). After the solution was concentrated to about half of its original amount, methanol (20 ml) was added to the residue. The precipitate thus formed was collected by filtration, whereby 76 mg (23.1%) of the title compound was obtained. The physical properties of the resulting compound are as follows:

$^1$H-NMR(DMSO-d$_6$-D$_2$O) δ: 1.80–1.92(2H,m), 2.30–2.40(2H,m), 2.70(6H,s), 3.20–3.66(6H,m), 3.75(6H,s), 4.38–4.42(2H,m), 6.68–6.77(2H,m), 7.10(2H,d,J=5.1 Hz), 7.79–8.35(4H,m), 8.57–9.00(6H,m), 9.24(1H,s), 9.51(1H,s), 9.89(1H,s).

IR(KBr)cm$^{-1}$: 3399, 1711, 1668, 1596, 1541, 1435, 1342, 1249

Example 37

Synthesis of 1-(3-amino-1,8-naphthalimido)-3-[N-[3-[N-[2-[N-[2-[N-(3-dimethylaminopropyl) carbamoyl]-1-methylpyrrol-4-yl]carbamoyl]-1-methylpyrrol-4-yl]carbamoyl]propyl]carbamoyl]-5-[N-[2-[[2-(3-nitro-1,8-naphthalimido)ethyl]amino] ethyl]carbamoyl]benzene dihydrochloride (Compound No. 42)

In water (50 ml) was dissolved 152 mg (0.15 mmol) of the compound obtained in Referential Example 13, followed by catalytic reduction at room temperature for 2 hours in the presence of platinum oxide (300 mg) as a catalyst under a hydrogen atmosphere of about 3 atmospheric pressure. After completion of the reaction, the catalyst was filtered off and the residue was lyophilized. The powder thus obtained was suspended in N,N-dimethylformamide (5 ml). Triethylamine (0.3 ml) and 36.5 mg (0.15 mmol) of 3-nitro-1,8-naphthalic anhydride were added to the resulting suspension and the mixture was stirred at 80° C. for 30 minutes. After cooling, the reaction mixture was added successively with 1N hydrochloric acid (1 ml) and water (2 ml). The resulting suspension was purified by reversed phase column chromatography (CHP-20P/mobile phase; water acetonitrile=60:40). The eluate containing the target compound was concentrated to about 30 ml and the residue was lyophilized, whereby 43 mg (23.7%) of the title compound was obtained. The physical properties of the resulting compound are as follows:

$^1$H-NMR(DMSO-d$_6$-D$_2$O) δ: 1.60–1.64(2H,m), 1.75–1.85(2H,m), 2.20–2.4(10H,m), 2.75–3.34(10H,m), 3.69(6H,s), 4.11(2H,brs), 6.69(2H,brs), 7.05(2H,brs), 7.32 (1H,brs), 7.60–7.68(1H,m), 7.83–7.89(4H,m), 8.01–8.06 (2H,m), 8.20–8.23(1H,brs), 8.43–8.55(2H,brs), 8.79(1H, brs), 9.18(1H,brs).

IR(KBr)cm$^{-1}$: 3404, 1704, 1660, 1595, 1541, 1441, 1348, 1255

Example 38

Synthesis of 1-[N-[2-[[2-[4-(4-formamido-1-methylpyrrole-2-carboxyamido)-1-methylpyrrole-2-carboxamido]ethyl]amino]ethyl]carbamoyl]-3-(3-nitro-1,8-naphthalimido)-5-[N-[2-[[2-(3-nitro-1,8-naphthalimido)ethyl]amino]ethyl]carbamoyl] benzene dihydrochloride (Compound No. 43)

To a solution of 290 mg (1 mmol) of 4-(4-formamido-1-methylpyrrole-2-carboxyamido)-1-methylpyrrole-2-carboxylic acid in N,N-dimethylformamide (3 ml) were added 149 mg (1.1 mmol) of 1-hydroxybenzotriazole and 227 mg (1.1 mmol) of N,N'-dicyclohexylcarbodiimide, followed by reaction at 50° C. for 1 hour (reaction mixture 1). On the side, triethylamine (2.0 ml) was added to a solution of 1445 mg (2.0 mmol) of the compound obtained in Referential Example 4 in N,N-dimethylformamide (4 ml) and the mixture was stirred at room temperature for 2 minutes. The reaction mixture 1 was added to the resulting suspension, followed by stirring at room temperature for 30 minutes. Under reduced pressure, excess triethylamine was distilled off. To the residue was added 1N hydrochloric acid (6 ml) and the mixture was purified by reversed phase column chromatography (CHP-20P/mobile phase; water:acetonitrile=90:10). The eluate containing the target compound was concentrated to about 50 ml, followed by lyophilization. The residue was suspended in N,N-dimethylformamide (3 ml). Triethylamine (0.5 ml) and 70.3 mg (0.15 mmol) of 3-nitro-1,8-naphthalic anhydride were added to the resulting suspension and the mixture was stirred at 80° C. for 1 hour. After cooling, the excess triethylamine was distilled off and 1N hydrochloric acid (4 ml) was added to the residue. The resulting suspension was purified by reversed phase column chromatography (CHP-20P/mobile phase; water:acetonitrile=75:25). The eluate containing the target compound was concentrated to about 30 ml, followed by lyophilization, whereby 113 mg (9.9%) of the title compound was obtained. The physical properties of the resulting compound are as follows:

$^1$H-NMR(DMSO-d$_6$-D$_2$O) δ: 3.10–3.25(6H,m), 3.33–3.42(2H,m), 3.74(3H,s), 3.79(3H,s), 4.37–4.44(2H,m), 6.85(1H,d,J=2.0 Hz), 6.93(1H,d,J=1.7 Hz), 7.10(1H,d,J=2.0 Hz), 7.14(1H,d,J=2.0 Hz), 7.97–8.22(7H,m), 8.58–8.74(4H, m), 8.86(1H,d,J=8.3 Hz), 9.40(1H,d,J=2.2 Hz), 9.55(1H,d, J=2.2 Hz).

Example 39

Synthesis of 1-(3-nitro-1,8-naphthalimido )-3-[N-[2-[[2-(3-nitro-1,8-naphthalimido)ethyl]amino]ethyl] carbamoyl]benzene hydrochloride (Compound No. 44)

To a suspension of 1.81 g (5.0 mmol) of the compound obtained in Referential Example 15 in dimethyl sulfoxide (10 ml) was added 1.05 g (6.5 mmol) of N,N'-carbonyldiimidazole. The resulting mixture was stirred at 50° C. for 30 minutes. To the resulting solution was added 2.63 g (6.0 mmol) of the compound obtained in Referential Example 5, followed by stirring at room temperature for 2 hours. The reaction mixture was purified by chromatography on a silica gel column. From the fraction eluted from chloroform-methanol (90:10), 1.24 g (36.9%) of the title compound was obtained. The physical properties of the resulting compound are as follows:

$^1$H-NMR(DMSO-d$_6$-D$_2$O) δ: 3.20(2H,brs), 3.38(2H,brs), 3.58(2H,brs), 4.40(2H,brs), 7.58–7.70(3H,m), 7.90(1H,d,J= 7.6 Hz), 8.01–8.15(2H,m), 8.62–8.72(3H,m), 8.85(1H,d,J= 7.6 Hz), 8.98(2H,s), 9.35(1H,s), 9.54(1H,s).

IR(KBr)cm$^{-1}$: 1713, 1672, 1600, 1540, 1421, 1339

Example 40

Synthesis of 1-(3-nitro-1,8-naphthalimido)-3-[N-[2-[[3-(3-nitro-1,8-naphthalimido)propyl]amino]ethyl] carbamoyl]benzene hydrochloride (A) and 1-(3-nitro-1,8-naphthalimido)-3-[N-[3-[[2-(3-nitro-1,8-naphthalimido)ethyl]amino]propyl]carbamoyl] benzene hydrochloride (B) (Compound No. 45)

To a suspension of 350 mg (0.66 mmol) of the compound obtained in Referential Example 16 in N,N-dimethylformamide (5 ml) were added 0.46 ml (3.3 mmol) of triethylamine and 159 mg (0.66 mmol) of 3-nitro-1,8-naphthalic anhydride and the resulting mixture was stirred at 100° C. for 1 hour. After cooling to room temperature, the reaction mixture was purified by chromatography on a silica gel column. From the fraction eluted from chloroform-methanol (90:10), 1-(3-nitro-1,8-naphthalimido)-3-[N-[2-[[3-(3-nitro-1,8-naphthalimido)propyl]amino]ethyl] carbamoyl]benzene and 1-(3-nitro-1,8-naphthalimido)-3-[N-[3-[[2-(3-nitro-1,8-naphthalimido)ethyl]amino]propyl] carbamoyl]benzene were obtained, separately. The compounds thus obtained were treated with 6N hydrochloric acid (0.5 ml) in methanol, followed by precipitation with diethyl ether, whereby their hydrochlorides were obtained in amounts of 90 mg (19.0%) and 100 mg (21.1%), respectively. The physical properties of the compounds thus obtained are as follows:

(A) $^1$H-NMR(DMSO-d$_6$-D$_2$O) δ: 2.02–2.10(2H,m), 3.07–3.14(4H,m), 3.58–3.61(2H,m), 4.12–4.16(2H,m), 7.60–7.69(2H,m), 7.88–8.00(2H,m), 7.91(1H,s), 7.99–8.10 (3H,m), 8.64–8.93(6H,m), 9.44(1H,s), 9.50(1H,s).

IR(KBr)cm$^{-1}$: 1711, 1669, 1597, 1540, 1422, 1339

(B) $^1$H-NMR (DMSO-d$_6$-D$_2$O) δ: 1.85–1.88(2H,m), 3.03–3.07(2H,m), 3.32–3.37(4H,m), 4.37–4.40(2H,m), 7.58–7.66(2H,m), 7.82(1H,s), 7.92(1H,d,J=7.8 Hz), 8.02–8.10(2H,m), 8.68(2H,d,J=7.3 Hz), 8.76(1H,d,J=8.3 Hz), 8.81(1H,d,J=8.3 Hz), 8.94(2H,dd,J=3.2,3.6 Hz), 9.45 (1H,s), 9.50(1H,s).

IR(KBr)cm$^{-1}$: 1712, 1670, 1597, 1539, 1422, 1340

Example 41

Synthesis of 1-[N-(3-dimethylaminopropyl) carbamoyl]-3-(3-nitro-1,8-naphthalimido)-5-[N-[2-[[2-(3-nitro-1,8-naphthalimido)ethyl]amino]ethyl] carbamoyl]benzene hydrochloride (Compound No. 47)

To a suspension of 406 mg (1.0 mmol) of 5-(3-nitro-1,8-naphthalimido)isophthalic acid, which had been synthesized in a similar manner to Referential Example 1, in N,N-dimethylformamide (2 ml) was added 324 mg (2.0 mmol) of N,N'-carbonyldiimidazole. The resulting mixture was stirred at 50° C. for 30 minutes. At room temperature, 102 mg (1.0 mmol) of diethylaminoethylamine was added to the resulting solution, followed by stirring for 15 minutes. The resulting solution was added to a suspension of 482 mg (1.2 mmol) of the compound obtained in Referential Example 5 and 0.7 ml (5.0 mmol) of triethylamine in N,N-dimethylformamide (3 ml), followed by stirring at room temperature for 30 minutes. The excess triethylamine was distilled off under reduced pressure. To the residue was added 3N hydrochloric acid (6 ml) and the mixture was purified by reversed phase column chromatography (CHP-20P/mobile phase; water:acetonitrile=85:15). The eluate containing the target compound was concentrated, followed by lyophilization, whereby 175 mg (20.0%) of the title compound was obtained. The physical properties of the resulting compound are as follows:

$^1$H-NMR(DMSO-d$_6$-D$_2$O) δ: 2.76(6H,s), 3.15–3.22(4H, m), 3.32–3.36(2H,m), 3.60–3.64(4H,m), 4.38–4.42(2H,m), 7.95–8.05(3H,m), 8.14(1H,dd,J=7.6,8.1 Hz), 8.48(1H,s), 8.67–8.73(3H,m), 8.87(1H,d,J=8.3 Hz), 8.99(2H,dd,J=2.2, 8.5 Hz), 9.38(1H,d,J=2.2 Hz), 9.56(1H,d,J=2.2 Hz).

IR(KBr)cm$^{-1}$: 1713, 1669, 1598, 1540, 1421, 1368

Example 42

Synthesis of 1-[N-(2-dimethylaminoethyl) carbamoyl]-3-(3-nitro-1,8-naphthalimido)-5-[N-[2-[[2-(3-nitro-1,8-naphthalimido)ethyl]amino]ethyl] carbamoyl]benzene hydrochloride (Compound No. 48)

In accordance with the process as described above in Example 41, 50 mg (4.7%) of the title compound was obtained from 500 mg (1.23 mmol) of the compound obtained in Referential Example 1 and 494 mg (1.23 mmol) of the compound obtained in Referential Example 3. The physical properties of the resulting compound are as follows:

$^1$H-NMR(DMSO-d$_6$-D$_2$O) δ: 1.85–1.95(2H,m), 2.72(6H, m), 3.07–3.14(2H,m), 3.21–3.30(2H,m), 3.59–3.67(2H,m), 4.37–4.44(2H,m), 7.98–8.13(4H,m), 8.59–8.96(7H,m), 9.44 (1H,d,J=2.4 Hz), 9.56(1H,d,J=2.2 Hz).

IR(KBr)cm$^{-1}$: 1713, 1669, 1600, 1541, 1421, 1343

Example 43

Synthesis of 1-methylcarbamoyl-3-(3-nitro-1,8-naphthalimido)-5-[N-[2-[[2-(3-nitro-1,8-naphthalimido)ethyl]amino]ethyl]carbamoyl] benzene hydrochloride (Compound No. 49)

To a suspension of 231 mg (0.40 mmol) of the compound obtained in Referential Example 16 in N,N-dimethylformamide (4 ml) were added 0.5 ml of triethylamine and 97.3 mg (0.40 mmol) of 3-nitro-1,8-naphthalic anhydride, followed by stirring at 60° C. for 30 minutes. The reaction mixture was purified by chromatography on a silica gel column. From the fraction eluted from chloroform-methanol-aqueous ammonia (90:9.7:0.3), 92 mg (30.0%) of the title compound was obtained. The physical-properties of the resulting compound are as follows:

$^1$H-NMR(DMSO-d$_6$-D$_2$O) δ: 2.76 and 2.77(total 3H, each s), 3.18(2H,t,J=5.6 Hz), 3.35(2H,t,J=5.5 Hz), 3.57(2H,t,J= 6.0 Hz), 4.37(2H,t,J=5.6 Hz), 7.85–8.12(4H,m), 8.38(1H, brs), 8.58–8.97(7H,m), 9.32(1H,d,J=2.2 Hz), 9.51(1H,d,J= 2.2 Hz).

IR(KBr)cm$^{-1}$: 1713, 1671, 1598, 1541, 1422, 1341

Example 44

Synthesis of 1-methylcarbamoyl-3-(1,8-naphthalimido)-5-[N-[2-[[2-(3-nitro-1,8-naphthalimido)ethyl]amino]ethyl]carbamoyl] benzene hydrochloride (Compound No. 50)

In accordance with the process as described above in Example 43, 92 mg (30.0%) of the title compound was obtained from 231 mg (0.40 mmol) of the compound obtained in Referential Example 17 and 79.3 mg (0.40 mmol) of 1,8-naphthalic anhydride. The reaction temperature was however changed to 100° C. The physical properties of the resulting compound are as follows:

$^1$H-NMR(DMSO-d$_6$-D$_2$O) δ: 2.78 and 2.79(total 3H, each s), 3.20(2H,t,J=5.7 Hz), 3.35(2H,t,J=5.4 Hz), 3.54–3.62(2H, m), 4.37(2H,t,J=5.5 Hz), 7.82(2H,t,J=7.7 Hz), 7.95(1H,t,J= 1.4 Hz), 8.02(1H,t,J=1.4 Hz), 8.38–8.50(5H,m), 8.70(1H,d, J=7.3 Hz), 8.84(1H,d,J=8.5 Hz), 8.97(1H,d,J=2.4 Hz), 9.54 (1H,d,J=2.2 Hz).

IR(KBr)cm$^{-1}$: 1714, 1701, 1662, 1593, 1542, 1419, 1343

Example 45

Synthesis of 1-(3-nitro-1,8-naphthalimido)-3-[N-[2-[[2-(3-nitro-1,8-naphthalimido)ethyl]amino]ethyl] carbamoyl]-5-[N-(2-pyrrolidinoethyl)carbamoyl] benzene hydrochloride (Compound No. 52)

In accordance with the process as described above in Example 43, 92 mg (30.0%) of the title compound was obtained from 231 mg (0.40 mmol) of the compound obtained in Referential Example 18 and 79.3 mg (0.40 mmol) of 3-nitro-1,8-naphthalic anhydride. The physical properties of the resulting compound are as follows:

$^1$H-NMR(DMSO-d$_6$-D$_2$O) δ: 1.80–2.10(4H,m), 3.00–3.70(14H,m), 4.40–4.45(2H,m), 8.00–8.20(4H,m), 8.60–8.75(4H,m), 8.88(1H,d,J=8.5 Hz), 8.95–9.05(2H,m), 9.44(1H,s), 9.58(1H,s).

IR(KBr)cm$^{-1}$: 1713, 1670, 1598, 1541, 1343

Example 46

Synthesis of 1-(3-nitro-1,8-naphthalimido)-3-[N-[2-[[2-(3-nitro-1,8-naphthalimido)ethyl]amino]ethyl] carbamoyl]-5-[N-(2-piperidinoethyl)carbamoyl] benzene hydrochloride (Compound No. 53)

In accordance with the process as described above in Example 43, 650 mg (72.2%) of the title compound was obtained from 711 mg (1.0 mmol) of the compound obtained in Referential Example 19 and 243 mg (1.0 mmol) of 3-nitro-1,8-naphthalic anhydride. The physical properties of the resulting compound are as follows:

$^1$H-NMR(DMSO-d$_6$-D$_2$O) δ: 1.30–1.50(2H,m), 1.60–1.90(6H,m), 2.85–3.00(2H,m), 3.20–3.30(4H,m), 3.35–3.45(2H,m), 3.50–3.70(4H,m), 4.40–4.48(2H,m), 7.94 (1H,brs), 8.00–8.17(3H,m), 8.50(1H,brs), 8.65–8.75(3H,m), 8.87(1H,d,J=8.1 Hz), 8.95–9.02(2H,m), 9.37(1H,brs), 9.56 (1H,s).

IR(KBr)cm$^{-1}$: 1713, 1670, 1598, 1541, 1422, 1343

Example 47

Synthesis of 1-[N-[2-[[2-(1,8-naphthalimido)ethyl] amino]ethyl]carbamoyl]-3-(3-nitro-1,8-naphthalimido)-5-[N-(2-piperidinoethyl)carbamoyl] benzene hydrochloride (Compound No. 54)

In accordance with the process as described above in Example 44, 600 mg (70.2%) of the title compound was obtained from 711 mg (1.0 mmol) of the compound obtained in Referential Example 19 and 198 mg (1.0 mmol) of 1,8-naphthalic anhydride. The physical properties of the resulting compound are as follows:

$^1$H-NMR(DMSO-d$_6$-D$_2$O) δ: 1.35–1.75(4H,m), 1.80–1.90(2H,m), 2.85–3.00(2H,m), 3.20–3.30(4H,m), 3.35–3.45(2H,m), 3.50–3.75(6H,m), 4.37–4.45(2H,m), 7.81 (1H,dd,J=7.6,8.1 Hz), 7.92(1H,s), 8.07(1H,s), 8.14(1H,dd, J=7.6,8.3 Hz), 8.33–8.50(5H,m), 8.74–9.03(3H,m), 9.53 (1H,s).

IR(KBr)cm$^{-1}$: 1714, 1700, 1662, 1593, 1541, 1344

Example 48

Synthesis of 1-morpholinocarbonyl-3-(3-nitro-1,8-naphthalimido)-5-[N-[2-[[2-(3-nitro-1,8-naphthalimido)ethyl]amino]ethyl]carbamoyl] benzene hydrochloride (Compound No. 55)

In accordance with the process as described above in Example 43, 125 mg (30.4%) of the title compound was obtained from 317 mg (0.50 mmol) of the compound obtained in Referential Example 20 and 122 mg (0.50 mmol) of 3-nitro-1,8-naphthalic anhydride. The physical properties of the resulting compound are as follows:

$^1$H-NMR(DMSO-d$_6$-D$_2$O) δ: 3.14–3.21(2H,m), 3.30–3.42(4H,m), 4.34–4.42(2H,m), 7.68(1H,t,J=1.7 Hz), 7.84(1H,t,J=1.8 Hz), 7.96(1H,t,J=1.5 Hz), 8.01(1H,t,J=7.8 Hz), 8.10(1H,t,J=7.8 Hz), 8.65–8.70(3H,m), 8.82(1H,d,J= 8.3 Hz), 8.95(2H,d,J=2.4 Hz), 9.36(1H,d,J=2.2 Hz), 9.52 (1H,d,J=2.2 Hz).

IR(KBr)cm$^{-1}$: 1714, 1673, 1598, 1540, 1425, 1341

Example 49

Synthesis of 1-(4-methylpiperazino)carbonyl-3-(3-nitro-1,8-naphthalimido)-5-[N-[2-[[2-(3-nitro-1,8-naphthalimido)ethyl]amino]ethyl]carbamoyl]benzene hydrochloride (Compound No. 57)

In accordance with the process as described above in Example 43, 210 mg (24.1%) of the title compound was obtained from 683 mg (1.0 mmol) of the compound obtained in Referential Example 19 and 243 mg (1.0 mmol) of 3-nitro-1,8-naphthalic anhydride. The physical properties of the resulting compound are as follows:

$^1$H-NMR(DMSO-d$_6$-D$_2$O) δ: 2.68–2.76(3H,brs), 2.72 (6H,m), 3.07–3.14(2H,m), 3.21–3.30(2H,m), 3.59–3.67(2H, m), 4.37–4.44(2H,m), 7.98–8.13(4H,m), 8.59–8.96(7H,m), 9.44(1H,d,J=2.4 Hz), 9.56(1H,d,J=2.2 Hz).

IR(KBr)cm$^{-1}$: 1713, 1669, 1598, 1540, 1421, 1368

Example 50

Synthesis of 1-(4-methylpiperazino)carbonyl-3-(1,8-naphthalimido)-5-[N-[2-[[2-(3-nitro-1,8-naphthalimido) ethyl]amino]ethyl]carbamoyl]benzene hydrochloride (Compound No. 58)

In accordance with the process as described above in Example 43, 211 mg (24.3%) of the title compound was obtained from 670 mg (1.05 mmol) of the compound obtained in Referential Example 22 and 243 mg (1.0 mmol) of 3-nitro-1,8-naphthalic anhydride. The physical properties of the resulting compound are as follows:

$^1$H-NMR(DMSO-d$_6$-D$_2$O) δ: 2.75(3H,brs), 3.15–3.22 (2H,m), 3.32–3.40(2H,m), 4.36–4.42(2H,m), 7.68–8.05(6H, m), 8.49–8.68(6H,m), 8.95(1H,brs), 9.34(1H,brs).

IR(KBr)cm$^{-1}$: 1709, 1667, 1596, 1541, 1430, 1346

Example 51

Synthesis of 1-(4-methylpiperazino)carbonyl-3-(1,8-naphthalimido)-5-[N-[2-[[2-(1,8-naphthalimido)ethyl]amino]ethyl]carbamoyl]benzene hydrochloride (Compound No. 59)

In accordance with the process as described above in Example 44, 775 mg (60.1%) of the title compound was obtained from 1053 mg (1.65 mmol) of the compound obtained in Referential Example 22 and 297 mg (1.50 mmol) of 1,8-naphthalic anhydride. The physical properties of the resulting compound are as follows:

$^1$H-NMR(DMSO-d$_6$-D$_2$O) δ: 2.77(3H,brs), 3.15–3.23 (2H,m), 3.31–3.39(2H,m), 3.53–3.61(2H,m), 4.33–4.41(2H, m), 7.73(1H,brs), 7.80–7.96(5H,m), 8.09(1H,brs), 8.37–8.57(8H,m).

IR(KBr)cm$^{-1}$: 1704, 1663, 1590, 1438, 1353, 1241

Example 52

Synthesis of 1-(4-chloro-1,8-naphthalimido)-3-(4-methylpiperazino)carbonyl-5-[N-[2-[[2-(3-nitro-1,8-naphthalimido)ethyl]amino]ethyl]carbamoyl]benzene hydrochloride (Compound No. 60)

In accordance with the process as described above in Example 43, 517 mg (54.6%) of the title compound was obtained from 751 mg (1.10 mmol) of the compound obtained in Referential Example 21 and 233 mg (1.0 mmol) of 4-chloro-1,8-naphthalic anhydride. The physical properties of the resulting compound are as follows:

$^1$H-NMR(DMSO-d$_6$-D$_2$O) δ: 2.77(3H,brs), 3.15–3.23 (2H,m), 3.31–3.39(2H,m), 3.56–3.64(2H,m), 4.31–4.39(2H, m), 7.74(1H,brs), 7.91–8.13(5H,m), 8.41(1H,d,J=7.8 Hz), 8.09(1H,brs), 8.55(2H,t,J=7.4 Hz), 8.70(1H,d,J=7.3 Hz), 8.83(1H,d,J=8.3 Hz), 8.97(1H,d,J=2.0 Hz), 9.52(1H,d,J=2.2 Hz).

IR(KBr)cm$^{-1}$: 1710, 1667, 1595, 1541, 1423, 1344

Example 53

Synthesis of 1-(4-ethylpiperazino)carbonyl-3-[N-[2-[[2-(1,8-naphthalimido)ethyl]amino]ethyl]carbamoyl]-5-(3-nitro-1,8-naphthalimido)benzene hydrochloride (Compound No. 62)

In accordance with the process as described above in Example 44, 250 mg (41.3%) of the title compound was obtained from 500 mg (0.72 mmol) of the compound obtained in Referential Example 23 and 142 mg (0.72 mmol) of 1,8-naphthalic anhydride. The physical properties of the resulting compound are as follows:

$^1$H-NMR(DMSO-d$_6$-D$_2$O) δ: 1.17–1.26(3H,m), 3.05–3.25(10H,m), 3.35–3.40(2H,m), 3.55–3.70(4H,m), 4.35–4.45(2H,m), 7.77(1H,s), 7.82–7.92(3H,m), 8.07(1H,s), 8.12–8.16(1H,m), 8.39(1H,d,J=8.1 Hz), 8.52(1H,d,J=7.3 Hz), 8.74(1H,d,J=7.3 Hz), 8.86(1H,d,J=8.1 Hz), 9.02(1H,s), 9.55(1H,s).

IR(KBr)cm$^{-1}$: 1711, 1662, 1594, 1541, 1424, 1369, 1342

Example 54

Synthesis of 1-(4-chloro-1,8-naphthalimido)-3-(4-ethylpiperazino)carbonyl-5-[N-[2-[[2-(3-nitro-1,8-naphthalimido)ethyl]amino]ethyl]carbamoyl]benzene hydrochloride (Compound No. 63)

In accordance with the process as described above in Example 43, 290 mg (46.0%) of the title compound was obtained from 500 mg (0.72 mmol) of the compound obtained in Referential Example 23 and 167 mg (0.72 mmol) of 4-chloro-1,8-naphthalic anhydride. The physical properties of the resulting compound are as follows:

NMR(DMSO-d$_6$-D$_2$O) δ: 1.17–1.27(3H,m), 3.05–3.15 (8H,m), 3.20–3.25(2H,m), 3.35–3.40(2H,m), 3.45–3.65(4H, m), 4.35–4.45(2H,m), 7.78(1H,s), 7.95–8.17(4H,m), 8.46 (1H,d,J=7.8 Hz), 8.59(2H,dd,J=7.6,8.8 Hz), 8.74(1H,d,J= 7.1 Hz), 8.87(1H,d,J=8.5 Hz), 9.02(2H,s), 9.56(1H,s).

IR(KBr)cm$^{-1}$: 1709, 1668, 1595, 1541, 1424, 1369, 1344

Example 55

Synthesis of 1-(3-nitro-1,8-naphthalimido)-3-[N-[2-[[2-(3-nitro-1,8-naphthalimido)ethyl]amino]ethyl]carbamoyl]-5-(4-piperidinopiperidino)carbonylbenzene hydrochloride (Compound No. 64)

In accordance with the process as described above in Example 43, 890 mg (94.7%) of the title compound was obtained from 750 mg (1.0 mmol) of the compound obtained in Referential Example 24 and 243 mg (1.0 mmol) of 3-nitro-1,8-naphthalic anhydride. The physical properties of the resulting compound are as follows:

$^1$H-NMR(DMSO-d$_6$-D$_2$O) δ: 1.60–2.20(8H,m), 2.80–3.00(2H,m), 3.20–3.30(2H,m), 3.35–3.50(10H,m), 3.55–3.65(2H,m), 4.40–4.50(2H,m), 4.65(1H,brs), 7.69(1H, s), 7.78(1H,s), 7.95–8.20(3H,m), 8.60–8.75(3H,m), 8.85 (1H,d,J=7.3 Hz), 8.98–9.03(2H,m), 9.29(1H,s), 9.54(1H,s).

IR(KBr)cm$^{-1}$: 1713, 1671, 1599, 1423, 1343

Example 56

Synthesis of 1-(4-methylpiperazino)carbonyl-3-(3-nitro-1,8-naphthalimido)-5-[N-[3-[[2-(3-nitro-1,8-naphthalimido)ethyl]amino]propyl]carbamoyl] benzene hydrochloride (A) and 1-(4-methylpiperazino)carbonyl-3-(3-nitro-1,8-naphthalimido)-5-[N-[2-[[3-(3-nitro-1,8-naphthalimido)propyl]amino]ethyl]carbamoyl] benzene hydrochloride (B) (Compound No. 65)

To a suspension of 1530 mg (2.2 mmol) of the compound obtained in Referential Example 25 in N,N-dimethylformamide (15 ml) were added 1.12 ml (8.0 mmol) of triethylamine and 486 mg (2.0 mmol) of 3-nitro-1,8-naphthalic anhydride, followed by stirring at 80° C. for 4 hours. After cooling to room temperature, the reaction mixture was purified by chromatography on a silica gel column. From the fraction eluted from chloroform-methanol (90:10), 1-(4-methylpiperazino)carbonyl-3-(3-nitro-1,8-naphthalimido)-5-[N-[3-[[2-(3-nitro-1,8-naphthalimido)ethyl]amino]propyl]carbamoyl]benzene and 1-(4-methylpiperazino)carbonyl-3-(3-nitro-1,8-naphthalimido)-5-[N-[2-[[3-(3-nitro-1,8-naphthalimido)propyl]amino]ethyl]carbamoyl]benzene were obtained, separately. The resulting compounds were treated with 6N hydrochloric acid (1 ml) in methanol (5 ml), followed by precipitation from diethyl ether, whereby 690 mg (35.4%) and 160 mg (8.2%) were obtained, respectively as a hydrochloride. The physical properties of the resulting compounds are as follows:

(A) $^1$H-NMR(DMSO-d$_6$-D$_2$O) δ: 1.82–1.92(2H,m), 2.82 (3H,.s), 3.05–3.10(2H,m), 3.15–3.20(8H,m), 3.30–3.40(4H m), 4.35–4.45(2H,m), 7.75(1H,s), 7.97(1H,s), 8.00–8.12 (3H,m), 8.55–8.85(4H,m), 8.90–9.00(2H,m), 9.43(1H,s), 9.50(1H,s).

IR(KBr)cm$^{-1}$: 1712, 1671, 1598, 1540, 1423, 1342

(B) $^1$H-NMR(DMSO-d$_6$-D$_2$O) δ: 2.00–2.10(2H,m), 2.82 (3H,s), 3.05–3.20(12H,m), 3.30–3.45(2H,m), 4.10–4.20 (2H,m), 7.77(1H,s), 8.03–8.15(4H,m), 8.65–8.72(2H,m), 8.77(1H,d,J=8.3 Hz), 8.84(1H,d,J=8.5 Hz), 8.95–9.02(2H, m), 9.46(1H,s), 9.54(1H,s).

The results of the pharmacological test on the anti-tumor effects of the invention compounds will be shown below in order to describe the usefulness of the compounds. Test 1 Cytotoxicity against KB cells After KB cells in the logarithmic growth phase were dispersed by treating with a trypsin/EDTA solution (0.25% trypsin, 2% EDTA in PBS), the trypsin/EDTA solution was removed by centrifugation. The residue was re-suspended in an MEM medium containing 10% fetal bovine serum. Then, an equivalent amount of a 0.2% trypan blue solution was added to a portion of the cell suspension, followed by mixing. The number of living cells which had not been dyed with the trypan blue was counted by a hemocytometer and the suspension was diluted and adjusted with the above-described culture medium to give a cell concentration of 1×10$^4$ cells/ml. Each well of a 96-well plate was inoculated with a 100-μl portion of the resulting suspension, in other words, was inoculated to give a concentration of 1×10$^3$ cells/well.

To the cells cultured in a CO$_2$ incubator for 24 hours after the inoculation was added 100 μl/well of a medicament solution, followed by culturing for 72 hours. To a control was added 100 μl of an MEM medium.

The cytotoxicity of the medicament was determined from a change in the number of the cells by using the crystal violet dying method.

Described specifically, 25% glutaraldehyde was added to the plate to give a concentration of 25 μl/well and the cells were fixed for about 15 minutes. After washing the plate with water, 100 μl/well of a 0.05% crystal violet solution dissolved in 20% methanol was added to dye the cells therewith for about 15 minutes. The plate was washed to remove the unbound crystal violet, followed by the addition of 100 μl/well of 0.05M NaH$_2$PO$_4$/ethanol (1:1 v/v), whereby the crystal violet bound to the cellular protein was extracted. The absorbance at 550 nm was measured by Model 3550 Microplate reader (BIO-RAD).

From the absorbance of each of medicament-treatment groups relative to the average absorbance of a medicament-treatment-free group which was set at 100, the concentration (IC$_{50}$) inducing 50% proliferation inhibition was calculated. The results are shown in Table 15.

TABLE 15

| Compound | Cytotoxicity [IC$_{50}$ (μM)] |
| --- | --- |
| Compound of Example 1 | 0.059 |
| Compound of Example 2 | 0.0061 |
| Compound of Example 3 | 2.6 |
| Compound of Example 4 | 0.048 |
| Compound of Example 6 | 0.064 |
| Compound of Example 7 | 4.1 |
| Compound of Example 8 | 0.050 |
| Compound of Example 9 | 0.023 |
| Compound of Example 10 | 0.023 |
| Compound of Example 11 | 0.14 |
| Compound of Example 13 | 1.6 |
| Compound of Example 14 | 1.3 |
| Compound of Example 15 | 0.21 |
| Compound of Example 16 | 6.6 |
| Compound of Example 17 | 0.28 |
| Compound of Example 33 | 7.1 |
| Compound of Example 34 | 4.7 |
| Compound of Example 38 | 6.9 |
| Compound of Example 39 | 0.0053 |
| Compound of Example 40 (A) | 0.003 |
| Compound of Example 40 (B) | 0.00023 |
| Compound of Example 41 | 3.1 |
| Compound of Example 42 | 0.15 |
| Compound of Example 43 | 0.025 |
| Compound of Example 44 | 0.015 |
| Compound of Example 45 | 0.066 |
| Compound of Example 46 | 0.053 |
| Compound of Example 47 | 0.0035 |
| Compound of Example 48 | 0.052 |
| Compound of Example 49 | 0.035 |
| Compound of Example 50 | 0.022 |
| Compound of Example 51 | 0.025 |
| Compound of Example 52 | 0.023 |
| Compound of Example 53 | 0.013 |
| Compound of Example 54 | 0.006 |
| Compound of Example 55 | 0.11 |
| Compound of Example 56 (A) | 0.039 |
| Compound of Example 56 (B) | 0.12 |

From Table 15, it was confirmed that the compounds according to the present invention exhibit excellent cytotoxicity against KB cells at a markedly low concentration. Capability of Exploitation in Industry Owing to high affinity with DNA and base selectivity, naphthalimidobenzamide derivatives and salts thereof according to the present invention each has inhibitory action against enzymes acting on DNA and binding of a transcription-related protein to DNA. Accordingly, the compounds according to the present invention are useful as preventives or remedies for various diseases typified by tumor.

What is claimed is:

1. A naphthalimidobenzamide compound represented by the following formula (1):

(I)

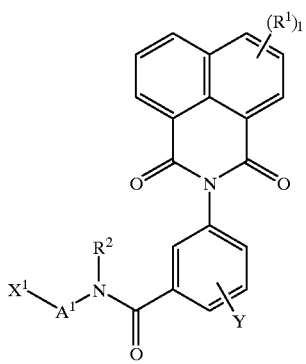

wherein,
- $R^1$ represents a hydrogen atom, a nitro group, a hydroxyl group, an amino group, a halogen atom, a cyano group, a carboxyl group, —$CONH_2$, —$NHCONH_2$, a $C_{1-6}$ alkyl group, a trihalogenoalkyl group, a $C_{1-6}$ alkoxy group, a $C_{1-6}$ alkylamino group, a di($C_{1-6}$ alkyl)amino group, a $C_{1-6}$ acyl group, a $C_{1-6}$ alkylcarbamoyl group, a di($C_{1-6}$ alkyl)carbamoyl group, a $C_{1-6}$ acylamino group, a $C_{1-6}$ alkylureyl group or a $C_{1-6}$ alkoxycarbonylamino group;
- $R^2$ represents a hydrogen atom or an alkyl group;
- l stands for an integer of 1 to 3;
- $A^1$ represents a linear or branched alkylene group which may be interrupted by —$N(R^3)$— ($R^3$ representing a hydrogen atom or an alkyl group), —O—, —S—, —C(=O)NH—, —NHC(=O)—, —S(=O)— or —$S(=O)_2$—,
- $X^1$ represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group; and
- Y represents a hydrogen atom or —C(=O)N($R^4$)—$A^2$—$X^2$ ($R^4$ representing a hydrogen atom or an alkyl group and $A^2$ representing a linear or branched alkylene group which may be interrupted by —$N(R^5)$— ($R^5$ representing a hydrogen atom or an alkyl group), —O—, —S—, —C(=O)NH—, —NHC(=O)—, —S(=O)— or —$S(=O)_2$—, $X^2$ representing a hydrogen atom, an aryl group, a heterocyclic group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, or $R^4$, $A^2$ and $X^2$ may form, together with a nitrogen atom adjacent thereto, a nitrogen-containing heterocyclic ring;

or a pharmaceutically acceptable salt thereof; and
when an aryl ring exists in the group represented by $X^1$, the aryl ring is a monocyclic to tetracyclic aryl group having 6 to 18 carbon atoms, and when a heteroaryl ring exists in the group represented by $X^1$, the heteroaryl ring is a monocyclic to tetracyclic heteroaryl group having 1 or 2 hetero atoms selected from the group consisting of nitrogen, oxygen and sulfur atoms and 2 to 17 carbon atoms, in which said aryl ring and said heteroaryl ring optionally have a substituent (I) selected from the group consisting of halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heteroaryl groups; or a substituent (II) selected from the group consisting of monocyclic nitrogen-containing heteroarylcarbamoyl groups, monocyclic nitrogen-containing heteroarylcarbonylamino groups, monocyclic nitrogen-containing heteroarylcarbamoyl-monocyclic nitrogen-containing heteroarylcarbamoyl groups and monocyclic nitrogen-containing heteroarylcarbonylamino-monocyclic nitrogen-containing heteroarylcarbonylamino groups, each of which is further substituted by any one of the above-exemplified substituents (I); and
when an aryl ring exists in the group represented by $X^2$, the aryl ring is a monocyclic to tetracyclic aryl group having 6 to 18 carbon atoms, and when a heterocyclic group exists in the group represented by $X^2$, the heterocyclic group is a monocyclic to tetracyclic, saturated or unsaturated heterocyclic group having a hetero atom selected from nitrogen, oxygen and sulfur atoms and 2 to 17 carbon atoms, in which said aryl ring and heterocyclic group optionally have a substituent (III) selected from halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl) carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heterocyclic groups; or a substituent (IV) selected from monocyclic nitrogen-containing heterocyclic carbamoyl groups, monocyclic nitrogen-containing heterocyclic carbonylamino groups, monocyclic nitrogen-containing heterocyclic carbamoyl-monocyclic nitrogen-containing heterocyclic carbamoyl groups, monocyclic nitrogen-containing heterocyclic carbonylamino-monocyclic nitrogen-containing heterocyclic carbonylamino groups, each of which is further substituted by any one of the above-exemplified substituents (III).

2. A naphthalimidobenzamide compound or pharmaceutically acceptable salt thereof according to claim 1, wherein:
- $R^1$ represents a hydrogen atom, a nitro group, an amino group, a $C_{1-6}$ alkoxy group or a halogen atom,
- $R^2$ represents a hydrogen atom or a $C_{1-3}$ alkyl group,
- l stands for 1,
- $A^1$ represents a linear or branched $C_{1-10}$ alkylene group which may be interrupted by NH—, —O— or —$S(=O)_2$—,
- $X^1$ represents an aryl or heteroaryl group, an aryldicarbonylimino or heteroaryldicarbonylimino group, an arylcarbonyl amino or heteroarylcarbonylamino group or an arylcarbamoyl or heteroarylcarbamoyl group (wherein the aryl ring or heteroaryl ring is as defined in claim 1),
- Y represents a hydrogen atom or —C(=O)N($R^4$)—$A^2$—$X^2$ ($R^4$ representing a hydrogen atom or a $C_{1-3}$ alkyl group and $A^2$ representing a linear or branched $C_{1-10}$ alkylene group which may be interrupted by —NH—, —N($CH_3$)—, —O— or —$S(=O)_2$—, $X^2$ representing a hydrogen atom, an aryl group, an aryldicarbonylimino or heteroaryldicarbonylimino group, an arylcarbonylamino or heteroarylcarbonylamino group, or an arylcarbamoyl or heteroarylcarbamoyl group (wherein the aryl ring or heterocyclic group is as defined in claim 1), or R⁴, A² and X² may form, together with a nitrogen atom adjacent thereto, a nitrogen-containing heterocyclic ring (wherein the heterocyclic ring is as defined in claim 1).

3. A pharmaceutical composition comprising a naphthalimidobenzamide compound or pharmaceutically acceptable salt thereof as claimed in any one of claims 1 to 2 and a pharmaceutically acceptable carrier.

4. A pharmaceutical composition according to claim 3, which is a remedy for a malignant tumor of either skin cancer, pancreatic cancer, breast cancer, or gastric cancer.

5. A method for treating a malignant tumor, which comprises administering a pharmacologically effective amount of a naphthalimidobenzamide compound or pharmaceutically acceptable salt thereof as claimed in any one of claims 1 to 2 to a patient in need thereof, wherein the tumor is either skin cancer, pancreatic cancer, breast cancer, or gastric cancer.

6. A process for preparing a compound represented by the following formula (1-a):

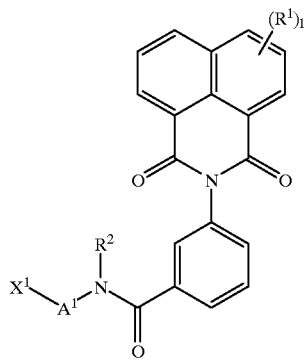

(1-a)

wherein,

R¹ represents a hydrogen atom, a nitro group, a hydroxyl group, an amino group, a halogen atom, a cyano group, a carboxyl group, —CONH₂, —NHCONH₂, a $C_{1-6}$ alkyl group, a trihalogenoalkyl group, a $C_{1-6}$ alkoxy group, a $C_{1-6}$ alkylamino group, a di($C_{1-6}$ alkyl)amino group, a $C_{1-6}$ acyl group, a $C_{1-6}$ alkylcarbamoyl group, a di($C_{1-6}$ alkyl(carbamoyl group, a $C_{1-6}$ acylamino group, a $C_{1-6}$ alkylureyl group or a $C_{1-6}$ alkoxycarbonylamino group;

R² represents a hydrogen atom or an alkyl group;

l stands for an integer of 1 to 3;

A¹ represents a linear or branched alkylene group which may be interrupted by —N(R³)— (R³ representing a hydrogen atom or an alkyl group), —O—, —S—, —C(=O)NH—, —NHC(=O)—, —S(=O)—, or —S(=O)₂—, and X¹ represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, provided that when an aryl ring exists in the group represented by X¹, the aryl ring is a monocyclic to tetracyclic aryl group having 6 to 18 carbon atoms, and when a heteroaryl ring exists in the group represented by X¹, the heteroaryl ring is a monocyclic to tetracyclic heteroaryl group having 1 or 2 hetero atoms selected from the group consisting of nitrogen, oxygen and sulfur atoms and 2 to 17 carbon atoms, in which said aryl ring and said heteroaryl ring optionally have a substituent (I) selected from the group consisting of halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heteroaryl groups; or a substituent (II) selected from the group consisting of monocyclic nitrogen-containing heteroarylcarbamoyl groups, monocyclic nitrogen-containing heteroarylcarbonylamino groups, monocyclic nitrogen-containing heteroarylcarbamoyl-monocyclic nitrogen-containing heteroarylcarbamoyl groups and monocyclic nitrogen-containing heteroarylcarbonylamino-monocyclic nitrogen-containing heteroarylcarbonylamino groups, each of which is further substituted by any one of the above-exemplified substituents (I), the process comprising condensing a compound of the following formula (5):

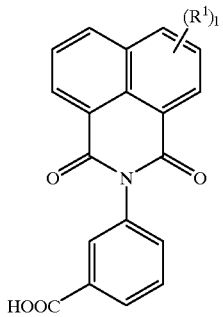

(5)

wherein,

R¹ and l have the same meaning as defined above, with a compound represented by the following formula (6):

(6)

wherein,

R², A¹ and X¹ have the same meanings as defined above.

7. A process for preparing a compound represented by the following formula (1-a):

(1-a)

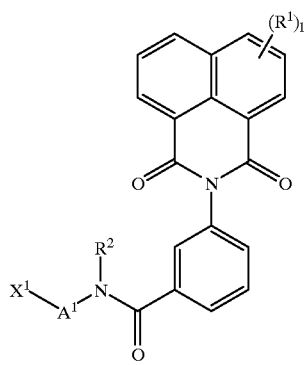

wherein,
R¹ represents a hydrogen atom, a nitro group, a hydroxyl group, an amino group, a halogen atom, a cyano group, a carboxyl group, —CONH₂, —NHCONH₂, a $C_{1-6}$ alkyl group, a trihalogenoalkyl group, a $C_{1-6}$ alkoxy group, a $C_{1-6}$ alkylamino group, a di($C_{1-6}$ alkyl)amino group, a $C_{1-6}$ acyl group, a $C_{1-6}$ alkylcarbamoyl group, a di($C_{1-6}$ alkyl)carbamoyl group, a $C_{1-6}$ acylamino group, a $C_{1-6}$ alkylureyl group or a $C_{1-6}$ alkoxycarbonylamino group;

R² represents a hydrogen atom or an alkyl group;

l stands for an integer of 1 to 3;

A¹ represents a linear or branched alkylene group which may be interrupted by —N(R³)— (R³ representing a hydrogen atom or an alkyl group), —O—, —S—, —C(=O)NH—, —NHC(=O)—, —S(=O)— or —S(=O)₂—, and X¹ represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, provided that when an aryl ring exists in the group represented by X¹, the aryl ring is a monocyclic to tetracyclic aryl group having 6 to 18 carbon atoms, and when a heteroaryl ring exists in the group represented by X¹, the heteroaryl ring is a monocyclic to tetracyclic heteroaryl group having 1 or 2 hetero atoms selected from the group consisting of nitrogen, oxygen and sulfur atoms and 2 to 17 carbon atoms, in which said aryl ring and said heteroaryl ring optionally have a substituent (I) selected from the group consisting of halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl) amino-$C_{1-6}$ alkylcarbamoyl groups and monocyclic nitrogen-containing heteroaryl groups; or a substituent (II) selected from the group consisting of monocyclic nitrogen-containing heteroarylcarbamoyl groups, monocyclic nitrogen-containing heteroarylcarbonylamino groups, monocyclic nitrogen-containing heteroarylcarbamoyl-monocyclic nitrogen-containing heteroarylcarbamoyl groups and monocyclic nitrogen-containing heteroarylcarbonylamino-monocyclic nitrogen-containing heteroarylcarbonylamino groups, each of which is further substituted by any one of the above-exemplified substituents (I), the process comprising condensing a compound of the following formula (5):

(5)

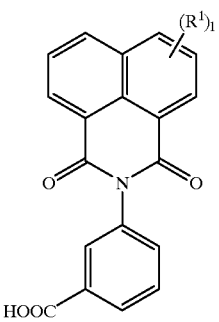

wherein,

R¹ and l have the same meaning as defined above, with a compound represented by the following formula (8):

(8)

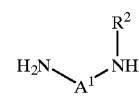

wherein

R² and A¹ have the same meanings as defined above, to obtain a compound represented by the following formula (7):

(7)

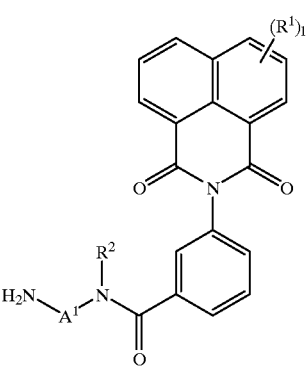

wherein,

R¹, R², l and A¹ have the same meanings as defined above, and then reacting the resulting compound (7) with a carboxylic acid or a dicarboxylic anhydride represented by the following formula (9) or (10):

Z¹—COOH (9)

or

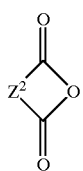
(10)

wherein, $Z^1$ represents a group forming $X^1$ as $NHCOZ^1$ and $Z^2$ represents a group forming $X^1$ as

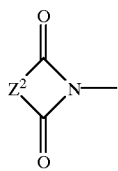

and $X^1$ has the same meaning as defined above.

8. A process for preparing a compound represented by the following formula (1-b):

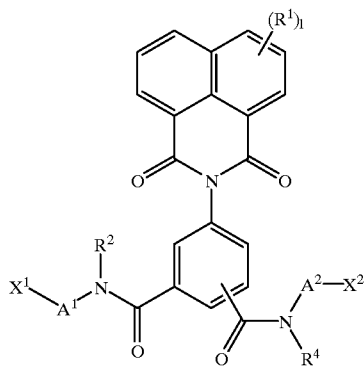
(1-b)

wherein, $R^1$ represents a hydrogen atom, a nitro group, a hydroxyl group, an amino group, a halogen atom, a cyano group, a carboxyl group, —$CONH_2$, —$NHCONH_2$, a $C_{1-6}$ alkyl group, a trihalogenoalkyl group, a $C_{1-6}$ alkoxy group, a $C_{1-6}$ alkylamino group, a di($C_{1-6}$ alkyl)amino group, a $C_{1-6}$ acyl group, a $C_{1-6}$ alkylcarbamoyl group, a di($C_{1-6}$ alkyl)carbamoyl group, a $C_{1-6}$ acylamino group, a $C_{1-6}$ alkylureyl group or a $C_{1-6}$ alkoxycarbonylamino group;

$R^2$ and $R^4$ are the same and each represents a hydrogen atom or an alkyl group;

l stands for an integer of 1 to 3;

$X^1$ and $X^2$ are the same and each represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, $A^1$ and $A^2$ are the same and each represents a linear or branched alkylene group which may be interrupted by —$N(R^3)$— ($R^3$ representing a hydrogen atom or an alkyl group), —O—, —S—, —C(=O)NH—, —NHC(=O)—, —S(=O)— or —S(=O)_2$—, provided that when an aryl ring exists in the group represented by $X^1$, the aryl ring is a monocyclic to tetracyclic aryl group having 6 to 18 carbon atoms, and when a heteroaryl ring exists in the group represented by $X^1$, the heteroaryl ring is a monocyclic to tetracyclic heteroaryl group having 1 or 2 hetero atoms selected from the group consisting of nitrogen, oxygen and sulfur atoms and 2 to 17 carbon atoms, in which said aryl ring and said heteroaryl ring optionally have a substituent (I) selected from the group consisting of halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heteroaryl groups; or a substituent (II) selected from the group consisting of monocyclic nitrogen-containing heteroarylcarbamoyl groups, monocyclic nitrogen-containing heteroarylcarbonylamino groups, monocyclic nitrogen-containing heteroarylcarbamoyl-monocyclic nitrogen-containing heteroarylcarbamoyl groups and monocyclic nitrogen-containing heteroarylcarbonylamino-monocyclic nitrogen-containing heteroarylcarbonylamino groups, each of which is further substituted by any one of the above-exemplified substituents (I), and when an aryl ring exists in the group represented by $X^2$, the aryl ring is a monocyclic to tetracyclic aryl group having 6 to 18 carbon atoms, and when a heterocyclic group exists in the group represented by $X^2$, the heterocyclic group is a monocyclic to tetracyclic, saturated or unsaturated heterocyclic group having a hetero atom selected from nitrogen, oxygen and sulfur atoms and 2 to 17 carbon atoms, in which said aryl ring and heterocyclic group optionally have a substituent (III) selected from halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heterocyclic groups; or a substituent (IV) selected from monocyclic nitrogen-containing heterocyclic carbamoyl groups, monocyclic nitrogen-containing heterocyclic carbonylamino groups, monocyclic nitrogen-containing heterocyclic carbamoyl-monocyclic nitrogen-containing heterocyclic carbamoyl groups, monocyclic nitrogen-containing heterocyclic carbonylamino-monocyclic nitrogen-containing heterocyclic carbonylamino groups, each of which is further substituted by any one of the above-exemplified substituents (III), the process comprising condensing a compound represented by the following formula (12):

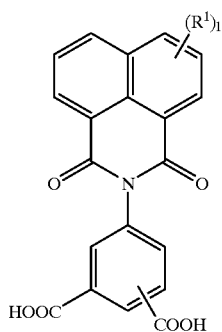

wherein,

R¹ and l have the same meaning as defined above, with a compound represented by the formula (6) or (13):

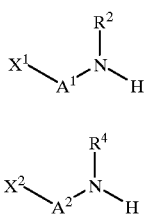

wherein,

X¹, X², A¹, A², R², and R⁴ have the same meanings as defined above.

9. A process for preparing a compound represented by the following formula (1-b):

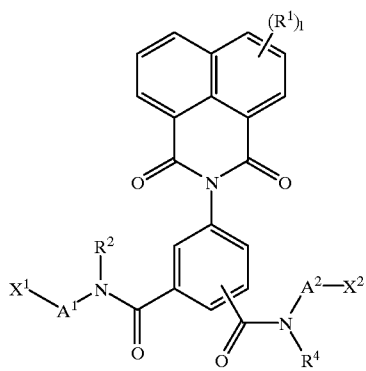

wherein,

R¹ represents a hydrogen atom, a nitro group, a hydroxyl group, an amino group, a halogen atom, a cyano group, a carboxyl group, —CONH₂, —NHCONH₂, a $C_{1-6}$ alkyl group, a trihalogenoalkyl group, a $C_{1-6}$ alkoxy group, a $C_{1-6}$ alkylamino group, a di($C_{1-6}$ alkyl)amino group, a $C_{1-6}$ acyl group, a $C_{1-6}$ alkylcarbamoyl group, a di($C_{1-6}$ alkyl)carbamoyl group, a $C_{1-6}$ acylamino group, a $C_{1-6}$ alkylureyl group or a $C_{1-6}$ alkoxycarbonylamino group;

R² and R⁴ are the same and each represents a hydrogen atom or an alkyl group;

l stands for an integer of 1 to 3;

X¹ and X² are the same and each represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, and A¹ and A² are the same and each represents a linear or branched alkylene group which may be interrupted by —N(R³)— (R³ representing a hydrogen atom or an alkyl group), —O—, —S—, —C(=O)NH—, —NHC(=O)—, —S(=O)— or —S(=O)₂—, provided that when an aryl ring exists in the group represented by X¹ the aryl ring is a monocyclic to tetracyclic aryl group having 6 to 18 carbon atoms, and when a heteroaryl ring exists in the group represented by X¹, the heteroaryl ring is a monocyclic to tetracyclic heteroaryl group having 1 or 2 hetero atoms selected from the group consisting of nitrogen, oxygen and sulfur atoms and 2 to 17 carbon atoms, in which said aryl ring and said heteroaryl ring optionally have a substituent (I) selected from the group consisting of halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heteroaryl groups; or a substituent (II) selected from the group consisting of monocyclic nitrogen-containing heteroarylcarbamoyl groups, monocyclic nitrogen-containing heteroarylcarbonylamino groups, monocyclic nitrogen-containing heteroarylcarbamoyl-monocyclic nitrogen-containing heteroarylcarbamoyl groups and monocyclic nitrogen-containing heteroarylcarbonylamino-monocyclic nitrogen-containing heteroarylcarbonylamino groups, each of which is further substituted by any one of the above-exemplified substituents (I), and when an aryl ring exists in the group represented by X², the aryl ring is a monocyclic to tetracyclic aryl group having 6 to 18 carbon atoms, and when a heterocyclic group exists in the group represented by X², the heterocyclic group is a monocyclic to tetracyclic, saturated or unsaturated heterocyclic group having a hetero atom selected from nitrogen, oxygen and sulfur atoms and 2 to 17 carbon atoms, in which said aryl ring and heterocyclic group optionally have a substituent (III) selected from halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heterocyclic groups; or a substituent (IV) selected from monocyclic nitrogen-containing heterocyclic carbamoyl groups, monocyclic nitrogen-containing heterocyclic carbonylamino groups, monocyclic nitrogen-containing heterocyclic carbamoyl-monocyclic nitrogen-containing heterocyclic carbamoyl groups, monocyclic nitrogen-containing heterocyclic carbonylamino-monocyclic nitrogen-containing heterocyclic carbonylamino groups, each of which is further substituted by any one of the above-exemplified substituents (III), the process comprising condensing a compound represented by the following formula (12):

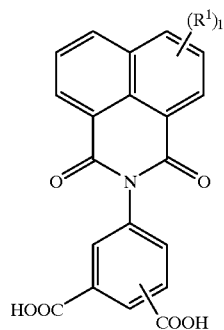

(12)

wherein, $R^1$ and l have the same meaning as defined above, with a compound represented by the formula (8) or (14):

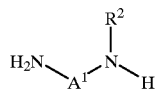

(8)

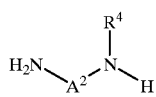

(14)

wherein, $A^1$, $A^2$, $R^2$, and $R^4$ have the same meanings as defined above, to obtain a compound represented by the following formula (15):

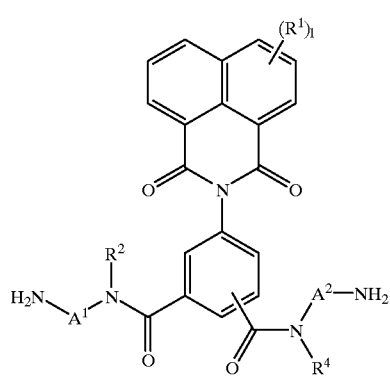

(15)

wherein, $R^1$, $R^2$, $R^4$, l, $A^1$, and $A^2$ have the same meanings as defined above, and then reacting the resulting compound (15) with a carboxylic acid or a dicarboxylic anhydride represented by the following formula (9) or (10):

$Z^1$—COOH (9)

or

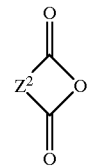

(10)

wherein, $Z^1$ represents a group forming $X^1$ as NHCOZ$^1$ and $Z^2$ represents a group forming $X^1$ as

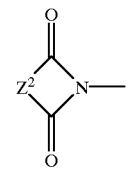

and $X^1$ has the same meaning as defined above.

10. A process for preparing a compound represented by the following formula (1-c):

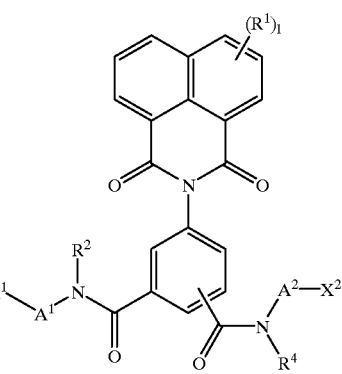

(1-c)

wherein, $R^1$ represents a hydrogen atom, a nitro group, a hydroxyl group, an amino group, a halogen atom, a cyano group, a carboxyl group, —CONH$_2$, —NHCONH$_2$, a C$_{1-6}$ alkyl group, a trihalogenoalkyl group, a C$_{1-6}$ alkoxy group, a C$_{1-6}$ alkylamino group, a di(C$_{1-6}$ alkyl)amino group, a C$_{1-6}$ acyl group, a C$_{1-6}$ alkylcarbamoyl group, a di(C$_{1-6}$ alkyl)carbamoyl group, a C$_{1-6}$ acylamino group, a C$_{1-6}$ alkylureyl group or a C$_{1-6}$ alkoxycarbonylamino group;

$R^2$ and $R^4$ are the same and each represents a hydrogen atom or an alkyl group;

l stands for an integer of 1 to 3;

$X^1$ represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, $X^2$ represents a hydrogen atom, an aryl group, a heterocyclic group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, or $R^4$, $A^2$ and $X^2$ may, together with a nitrogen atom adjacent thereto, form a nitrogen-containing heterocyclic group;

$A^1$ represents a linear or branched alkylene group which may be interrupted by —N($R^3$)— ($R^3$ representing a hydrogen atom or an alkyl group), —O—, —S—, —C(=O)NH—, —NHC(=O)—, —S(=O)— or —S(=O)$_2$—, and $A^2$ represents a linear or branched alkylene group which may be interrupted by —N($R^5$)— ($R^5$ representing a hydrogen atom or an alkyl group), —O—, —S—, —C(=O)NH—, —NHC(=O)—, —S(=O)— or —S(=O)$_2$—, provided that when an aryl ring exists in the group represented by $X^1$, the aryl ring is a monocyclic to tetracyclic aryl group having 6 to 18 carbon atoms, and when a heteroaryl ring exists in the group represented by $X^1$, the heteroaryl ring is a monocyclic to tetracyclic heteroaryl group having 1 or 2 hetero atoms selected from the group consisting of nitrogen, oxygen and sulfur atoms and 2 to 17 carbon atoms, in which said aryl ring and said heteroaryl ring optionally have a substituent (I) selected from the group consisting of halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl) amino-$C_{1-6}$ alkylcarbamoyl groups and monocyclic nitrogen-containing heteroaryl groups; or a substituent (II) selected from the group consisting of monocyclic nitrogen-containing heteroarylcarbamoyl groups, monocyclic nitrogen-containing heteroarylcarbonylamino groups, monocyclic nitrogen-containing heteroarylcarbamoyl-monocyclic nitrogen-containing heteroarylcarbamoyl groups and monocyclic nitrogen-containing heteroarylcarbonylamino-monocyclic nitrogen-containing heteroarylcarbonylamino groups, each of which is further substituted by any one of the above-exemplified substituents (I), and when an aryl ring exists in the group represented by $X^2$, the aryl ring is a monocyclic to tetracyclic aryl group having 6 to 8 carbon atoms, and when a heterocyclic group exists in the group represented by $X^2$, the heterocyclic group is a monocyclic to tetracyclic, saturated or unsaturated heterocyclic group having a hetero atom selected from nitrogen, oxygen and sulfur atoms and 2 to 17 carbon atoms, in which said aryl ring and heterocyclic group optionally have a substituent (III) selected from halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl) carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heterocyclic groups; or a substituent (IV) selected from monocyclic nitrogen-containing heterocyclic carbamoyl groups, monocyclic nitrogen-containing heterocyclic carbonylamino groups, monocyclic nitrogen-containing heterocyclic carbamoyl-monocyclic nitrogen-containing heterocyclic carbamoyl groups, monocyclic nitrogen-containing heterocyclic carbonylamino-monocyclic nitrogen-containing heterocyclic carbonylamino groups, each of which is further substituted by any one of the above-exemplified substituents (III), the process comprising reacting a compound represented by the following formula (16):

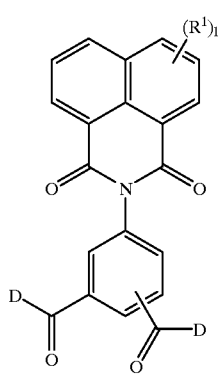

(16)

wherein, $R^1$ and l have the same meaning as defined above and —C(=O)—D means an activated carboxylic acid residue, with a compound represented by the following formula (6):

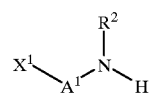

(6)

wherein, $R^2$, $A^1$ and $X^1$ have the same meanings as defined above, and then reacting the resulting compound represented by the following formula (13):

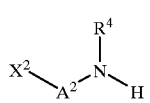

(13)

wherein, $R^4$, $A^2$ and $X^2$ have the same meanings as defined above.

11. A process for preparing a compound represented by the following formula (1-c):

(1-c)

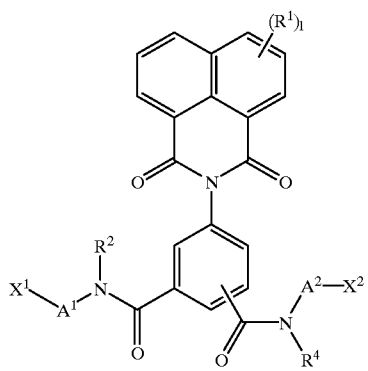

wherein,

- $R^1$ represents a hydrogen atom, a nitro group, a hydroxyl group, an amino group, a halogen atom, a cyano group, a carboxyl group, —CONH$_2$, —NHCONH$_2$, a $C_{1-6}$ alkyl group, a trihalogenoalkyl group, a $C_{1-6}$ alkoxy group, a $C_{1-6}$ alkylamino group, a di($C_{1-6}$ alkyl)amino group, a $C_{1-6}$ acyl group, a $C_{1-6}$ alkylcarbamoyl group, a di($C_{1-6}$ alkyl)carbamoyl group, a $C_{1-6}$ acylamino group, a $C_{1-6}$ alkylureyl group or a $C_{1-6}$ alkoxycarbonylamino group;
- $R^2$ and $R^4$ are the same and each represents a hydrogen atom or an alkyl group;
- l stands for an integer of 1 to 3;
- $X^1$ represents an aryl or heteroaryl group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group,
- $X^2$ represents a hydrogen atom, an aryl group, a heterocyclic group, an aryldicarbonylimino or heteroaryldicarbonylimino group, an arylamino or heteroarylamino group, an arylcarbonylamino or heteroarylcarbonylamino group, an arylcarbamoyl or heteroarylcarbamoyl group, an aryloxy or heteroaryloxy group, an arylthio or heteroarylthio group, an arylsulfinyl or heteroarylsulfinyl group, or an arylsulfonyl or heteroarylsulfonyl group, or $R^4$, $A^2$ and $X^2$ may, together with a nitrogen atom adjacent thereto, form a nitrogen-containing heterocyclic group;
- $A^1$ represents a linear or branched alkylene group which may be interrupted by —N($R^3$)— ($R^3$ representing a hydrogen atom or an alkyl group), —O—, —S—, —C(=O)NH—, —NHC(=O)—, —S(=O)— or —S(=O)$_2$—, and
- $A^2$ represents a linear or branched alkylene group which may be interrupted by —N($R^5$)— ($R^5$ representing a hydrogen atom or an alkyl group), —O—, —S—, —C(=O)NH—, —NHC(=O)—, —S(=O)— or —S(=O)$_2$—, provided that when an aryl ring exists in the group represented by $X^1$, the aryl ring is a monocyclic to tetracyclic aryl group having 6 to 18 carbon atoms, and when a heteroaryl ring exists in the group represented by $X^1$, the heteroaryl ring is a monocyclic to tetracyclic heteroaryl group having 1 or 2 hetero atoms selected from the group consisting of nitrogen, oxygen and sulfur atoms and 2 to 17 carbon atoms, in which said aryl ring and said heteroaryl ring optionally have a substituent (I) selected from the group consisting of halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl)carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heteroaryl groups; or a substituent (II) selected from the group consisting of monocyclic nitrogen-containing heteroarylcarbamoyl groups, monocyclic nitrogen-containing heteroarylcarbonylamino groups, monocyclic nitrogen-containing heteroarylcarbamoyl-monocyclic nitrogen-containing heteroarylcarbamoyl groups and monocyclic nitrogen-containing heteroarylcarbonylamino-monocyclic nitrogen-containing heteroarylcarbonylamino groups, each of which is further substituted by any one of the above-exemplified substituents (I), and when an aryl ring exists in the group represented by $X^2$, the aryl ring is a monocyclic to tetracyclic aryl group having 6 to 18 carbon atoms, and when a heterocyclic group exists in the group represented by $X^2$, the heterocyclic group is a monocyclic to tetracyclic, saturated or unsaturated heterocyclic group having a hetero atom selected from nitrogen, oxygen and sulfur atoms and 2 to 17 carbon atoms, in which said aryl ring and heterocyclic group optionally have a substituent (III) selected from halogen atoms, a nitro group, a hydroxyl group, an amino group, $C_{1-6}$ alkyl groups, $C_{1-6}$ alkylamino groups, di($C_{1-6}$ alkyl)amino groups, $C_{1-6}$ acylamino groups, $C_{1-6}$ alkylcarbamoyl groups, di($C_{1-6}$ alkyl) carbamoyl groups, $C_{1-6}$ alkylamino-$C_{1-6}$ alkylcarbamoyl groups, di($C_{1-6}$ alkyl)amino-$C_{1-6}$ alkylcarbamoyl groups and monocyclic nitrogen-containing heterocyclic groups; or a substituent (IV) selected from monocyclic nitrogen-containing heterocyclic carbamoyl groups, monocyclic nitrogen-containing heterocyclic carbonylamino groups, monocyclic nitrogen-containing heterocyclic carbamoyl-monocyclic nitrogen-containing heterocyclic carbamoyl groups, monocyclic nitrogen-containing heterocyclic carbonylamino-monocyclic nitrogen-containing heterocyclic carbonylamino groups, each of which is further substituted by any one of the above-exemplified substituents (III), the process comprising reacting a compound represented by the following formula (16):

(16)

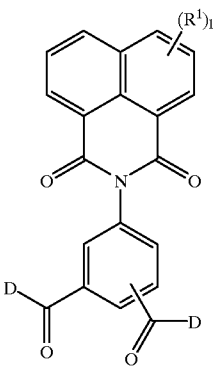

wherein,

- $R^1$ and l have the same meaning as defined above and —C(=O)—D means an activated carboxylic acid residue, with a compound represented by the following formula (13):

(13)

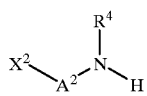

wherein, $R^4$, $A^2$ and $X^2$ have the same meanings as defined above, and then reacting the resulting compound with a compound represented by the following formula (8):

(8)

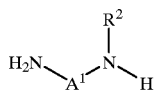

wherein, $R^2$ and $A^1$ have the same meanings as defined above, to obtain a compound represented by the following formula (17):

(17)

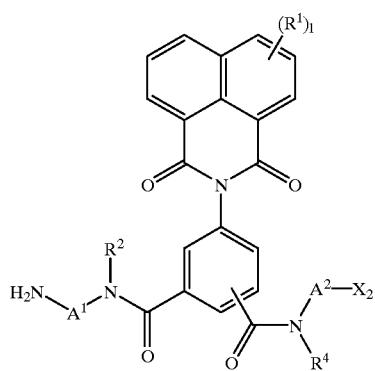

wherein, $R^1$, $R^2$, $R^4$, 1, $A^1$, $A^2$, and $X^2$ have the same meanings as defined above, and then reacting the resulting compound (17) with a carboxylic acid or a dicarboxylic anhydride represented by the following formula (9) or (10):

$Z^1$—COOH  (9)

or (10)

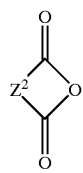

wherein, $Z^1$ represents a group forming $X^1$ as NHCOZ$^1$ and $Z^2$ represents a group forming $X^1$ as

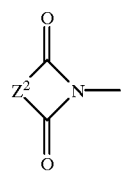

and $X^1$ has the same meaning as defined above.

12. A naphthalimidobenzamide compound according to claim 1, which is selected from the group consisting of 1,3-bis{N-{2-{{2-(1,8-naphthalimido) ethyl}amino}ethyl}carbamoyl}-5-(1,8-naphthalimido) benzene, 1-3-bis{N-{2-{{2-(3-nitro-1,8-naphthalimido) ethyl}amino}ethyl}carbamoyl}-5-(1,8-naphthalimido) benzene, 1,3-bis{N-{2-{{2-(3-nitro-1,8-naphthalimido) ethyl}}amino}ethyl}carbamoyl}-5-(3-nitro-1,8-naphthalimido)benzene, 1,3-bis{N-{2-{{2-(1,8-naphthalimido)ethyl}amino}ethyl}carbamoyl}-5-(3-nitro-1,8-naphthalimido)benzene, 1,3-bis{N-{2-{{2-(4-chloro-1,8-naphthalimido)ethyl}amino}ethyl}carbamoyl}-5-(3-nitro-1,8-naphthalimido)benzene, 1,3-bis{N-{3-{{3-(3-nitro-1,8-naphthalimido) propyl}amino}propyl}carbamoyl}-5-(3-nitro-1,8-naphthalimido)benzene, 1,3-bis{N-{2-{{2-(quinoline-3-carbonylamino)ethyl}amino}ethyl}carbamoyl}-5-(3-nitro-1,8-naphthalimido)benzene, 1,3-bis{N-{3-{N-{2-{N-{2-{N-(3-dimethylaminopropyl)carbamoyl}-1-methylpyrrol-4-yl}carbamoyl}-1-methylpyrrol-4-yl}carbamoyl}propyl}carbamoyl}-5-(3-nitro-1,8-naphthalimido)benzene,1,3-bis{N-{4-{N-{2-{N-{2-{N-(3-dimethylaminopropyl)carbamoyl}-1-methylpyrrol-4-yl}carbamoyl}-1-methylpyrrol-4-yl}carbamoyl}butyl}carbamoyl}-5-(3-nitro-1,8-naphthalimido)benzene,1,3-bis{N-{2-{{2-{4-(4-formamido-1-methylpyrrole-2-carbonylamino)-1-methylpyrrole-2-carbonylamino}ethyl}amino}ethyl}carbamoyl}-5-(3-nitro-1,8-naphthalimido)benzene,1-{N-{3-{N-{2-{N-{2-{N-(3-dimethylaminopropyl)carbamoyl}-1-methylpyrrol-4-yl}carbamoyl}-1-methylpyrrol-4-yl}carbamoyl}propyl}carbamoyl}-3-(3-nitro-1,8-naphthalimido)-5-{N-{2-{{2-(3-nitro-1,8-naphthalimido)ethyl}amino}ethyl}carbamoyl}benzene,1-{N-{3-{N-{2-{N-{2-{N-methylcarbamoyl}-1-methylpyrrol-4-yl}carbamoyl}-1-methylpyrrol-4-yl}carbamoyl}propyl}carbamoyl}-3-(3-nitro)-1,8-naphthalimido)-5-{N-{2-{{2-(3-nitro-1,8-naphthalimido)ethyl}amino}ethyl}carbamoyl}benzene,1-{N-{2-{{2-{4-(4-formamido-1-methylpyrrole-2-carboxyamido)-1-methylpyrrole-2-carboxamido}ethyl}amino}ethyl}carbamoyl}-3-(3-nitro-1,8-naphthalimido)-5-{N-{2-{{2-(3-nitro-1,8-naphthalimido)ethyl}amino}ethyl}carbamoyl}benzene,1-(3-nitro-1,8-naphthalimido)-3-{N-{2-{{2-(3-nitro-1,8-naphthalimido)ethyl}amino}ethyl}carbamoyl}benzene,1-(3-nitro-1,8-naphthalimido)-3-{N-{2-{{3-(3-nitro-1,8-naphthalimido)propyl}amino}ethyl}carbamoyl}benzene,d 1(3nitro-1,8-naphthalimido)-3-{N-{3-{{2-(3-nitro1,8-naphthalimido)ethyl}amnio}prophy}carbamoyl}benzene,1-{N-(3-dimethylaminopropyl)carbamoyl}-3-(3-nitro-1,8-naphthalimido)-5-{N-{2-{{2-(3-nitro-1,8-naphthalimido)ethyl}amino}ethyl}carbamoyl}benzene,1-(3-nitro-1,8-naphthalimido)-3-{N-{2-{{2-(3-nitro-1,8-naphthalimido)ethyl}amino}ethyl}carbamoyl}-5-{N-(2-pyrrolidinoethyl)carbamoyl}benzene,1-(3-nitro-1,8-naphthalimido)-3-{N-

{2-{{2-(3-nitro-1,8-naphthalimido)ethyl}amino}ethyl}carbamoyl}-5-{N-(2-piperidinoethyl)carbamoyl}benzene,1-{N-{2-{{2-(1,8-naphthalimido)ethyl}amino}ethyl}carbamoyl}-3-(3-nitro-1,8-naphthalimido)-5-{N-(2-piperidinoethyl)carbamoyl}benzene,1-(4-methylpiperazino)carbonyl-3-(1,8-naphthalimido)-5-{N-{2-{{2-(3-nitro-1,8-naphthalimido)ethyl}amino}ethyl}carbamoyl}benzene,1-(4-ethylpiperazino)carbonyl-3-{N-{2-{{2-(1,8-naphthalimido)ethyl}amino}ethyl}carbamoyl}-5-(3-nitro-1,8-naphthalimido)benzene and 1-(3-nitro-1,8-naphthalimido)-3-{N-{2-{{2-(3-nitro-1,8-naphtlhalimido)ethyl}amino}ethyl}carbamoyl}-5-(4-piperidinopiperidino)carbonylbenzene, or a pharmaceutically acceptable salt thereof.

\* \* \* \* \*